United States Patent

Baker et al.

[11] Patent Number: 6,083,980
[45] Date of Patent: Jul. 4, 2000

[54] FURANYL, TETRACYCLIC TRITERPENE DERIVATIVES WITH IMMUNOSUPPRESSANT ACTIVITY

[75] Inventors: Robert K. Baker, Cranford; Jianming Bao, Scotch Plains; Frank Kayser, Hoboken; Shouwu Miao, Edison; William H. Parsons, Belle Mead; Kathleen M. Rupprecht, Cranford, all of N.J.

[73] Assignee: Merck & Co., Inc., Rahway, N.J.

[21] Appl. No.: 09/164,313

[22] Filed: Oct. 1, 1998

Related U.S. Application Data

[60] Provisional application No. 60/063,112, Oct. 17, 1997.

[51] Int. Cl.⁷ .................. A61K 31/34; C07D 307/77; C07D 307/93
[52] U.S. Cl. .................. 514/468; 549/298; 549/457
[58] Field of Search .................. 549/298, 457; 514/468

[56] References Cited

U.S. PATENT DOCUMENTS

| | | |
|---|---|---|
| 3,483,191 | 12/1969 | Krakower et al. . |
| 4,453,967 | 6/1984 | Mori . |
| 5,599,950 | 2/1997 | Teng . |
| 5,631,282 | 5/1997 | Goetz . |
| 5,679,705 | 10/1997 | Baker et al. . |
| 5,696,156 | 12/1997 | Baker et al. . |
| 5,874,594 | 2/1999 | Baker et al. .......... 549/456 |

FOREIGN PATENT DOCUMENTS

| | | |
|---|---|---|
| WO 96/40688 | 12/1996 | WIPO . |
| WO 97/16068 | 5/1997 | WIPO . |
| WO 97/16182 | 5/1997 | WIPO . |
| WO 97/16437 | 5/1997 | WIPO . |
| WO 97/16438 | 5/1997 | WIPO . |
| WO 98/16532 | 4/1998 | WIPO . |

OTHER PUBLICATIONS

Abreu, et al., "A Nor–Triterpenoid From *Lophanthera Lactescens*", Phytochemistry, vol. 29(7), pp. 2257–2261, 1990.

Sabata, et al., "Tetranortriterpenoids and Related Substances. Part 19.1 Revised Structures of Atalantolide and Atalantin, Limonoids from the Root Bark of *Atalantia Monophylla* Correa (Rutaceae)", J. Chem. Soc. Perkin I, pp. 1876–1877, 1977.

*Primary Examiner*—Deborah C. Lambkin
*Attorney, Agent, or Firm*—J. A. Garcia-Rivas; Mark R. Daniel

[57] ABSTRACT

The compounds of Formula I

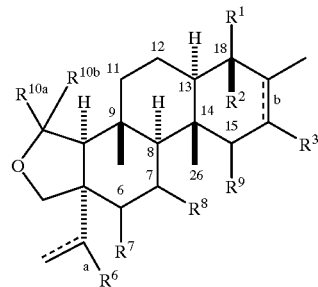

are useful as immunosuppressive agents.

11 Claims, No Drawings

FURANYL, TETRACYCLIC TRITERPENE DERIVATIVES WITH IMMUNOSUPPRESSANT ACTIVITY

Provisional Application No. 60/063,112 filed Oct. 17, 1997.

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves ophthalmopathy and asthma.

Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Anti-inflammatory agents such as NSAID's act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A (CsA), which was approved by the U.S. FDA in 1983 is currently the leading drug used to prevent rejection of transplanted organs. In 1993, FK-506 (Prograf) was approved by the U.S. FDA for the prevention of rejection in liver transplantation. CsA and FK-506 act by inhibiting the body's immune system from mobilizing its vast arsenal of natural protecting agents to reject the transplant's foreign protein. In 1994, CsA was approved by the U.S. FDA for the treatment of severe psoriasis and has been approved by European regulatory agencies for the treatment of atopic dermatitis. Though they are effective in fighting transplant rejection, CsA and FK-506 are known to cause several undesirable side effects including nephrotoxicity, neurotoxicity, and gastrointestinal discomfort.

Newer, safer drugs exhibiting less side effects are constantly being searched for in the field.

Four active components of *Spachea correa* were recently identified which inhibit thymidine uptake of T cells.

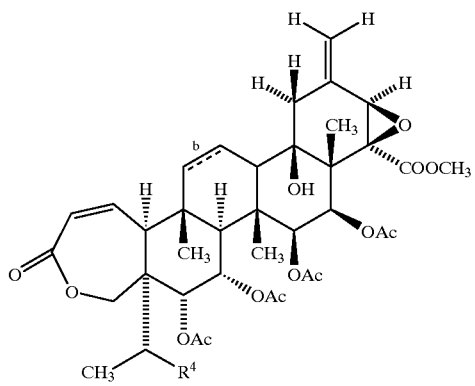

Formula 1(a) b is a single bond and $R^4$ is OAc
Formula 1(b) b is a double bond and $R^4$ is OAc
Formula 1(c) b is a single bond and $R^4$ is OH
Formula 1(d) b is a double bond and $R^4$ is OH These compounds are useful as immunosuppressive agents in animals, including man. The present invention describes newly developed immunosuppressive compounds derived from the compounds described in Formulae 1(a) through 1(d) and which have the relative stereochemistry depicted above.

SUMMARY OF THE INVENTION

This invention relates to a class of triterpene derivatives of the general structural Formula I

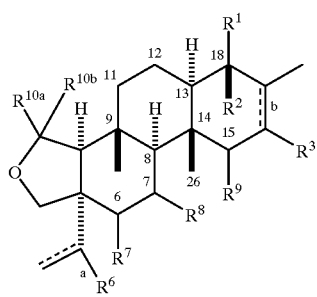

I are useful as immunosuppressives.

As an immunosuppressive, the compounds of this invention are useful in the treatment of autoimmune diseases, the prevention of rejection of foreign organ transplants and/or related afflictions, diseases and illnesses. Also within the scope of this invention are pharmaceutical formulations comprising a compound of Formula I and a pharmaceutical carrier, as well as, pharmaceutical formulations comprising a compound of Formula I, and one or more immunosuppressive compounds and a pharmaceutical carrier.

DETAILED DESCRIPTION OF THE INVENTION

A. Scope of the Invention

The present invention is related to compounds of Formula I, including but not limited to those specified in the examples, which are useful in a mammalian subject for the treatment and prevention of the resistance by transplantation of organs or tissue, graft-versus-host diseases brought about by medulla ossium transplantation; rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenic microorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; pollen allergies, reversible obstructive airway disease, bronchial asthma, allergic asthma, intrinsic asthma, extrinsic asthma and dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases, Coeliac diseases, proctitis, eosinophilic gastroenteritis, mastocytosis, Crohn's disease, ulcerative colitis, migraine, rhinitis, eczema, interstitial nephritis, Good-pasture's syndrome, hemolyticuremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth; muscular dystrophy; Pyoderma and Sezary's syndrome, Addison's disease, ischemia-reperfusion injury of organs which occurs upon preservation, transplantation or ischemic disease, for example, thrombosis and cardiac infraction, endotoxin-shock, pseudomembranous colitis, colitis caused by drug or radiation, ischemic acute renal insufficiency, chronic renal insufficiency, toxinosis caused by lung-oxygen or drug, for example, paracort and bleomycins, lung cancer, pulmonary emphysema, cataracta, siderosis, retinitis, pigmentosa, senile macular degeneration, vitreal scarring, corneal alkali burn; dermatitis erythema multiforme, linear IgA ballous dermatitis and cement dermatitis, gingivitis, periodontitis, sepsis, pancreatitis, diseases caused by environmental pollution, aging, carcinogenis, metastasis of carcinoma and hypobaropathy; disease caused by histamine or leukotriene-$C_4$ release; Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmention of chemotherapeutic effect, preventing or treating activity of cytomegalovirus infection, HCMV infection, and antiinflammatory activity; and treatment of immunodepression or a disorder involving immunodepression, including AIDS, cancer, senile dementia, trauma, chronic bacterial infection, and certain central nervous system disorders.

More particularly, this invention relates to compounds of the general structural Formula I:

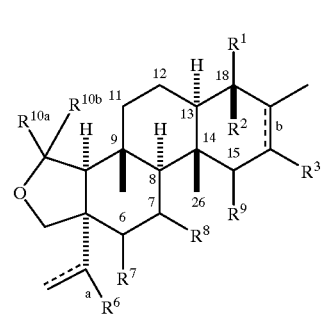

I or a pharmaceutically acceptable salt, crystal form, or hydrate, wherein:

a and b are independently a single bond or a double bond, and represented by ----- in the structure above;

n is: 0, 1 or 2;

r is: 0 or 1;

s is: 0 or 1;

$R^1$ and $R^{10a}$ are independently:
(1) H,
(2) =O, when $R^2$ is absent or $R^{10b}$ is absent respectively,
(3) $(C_1-C_{10})$-alkyl, wherein alkyl is unsubstituted or substituted with one or two substituents selected from the group consisting of:
  (a) halo, wherein halo is fluoro, chloro, bromo, or iodo,
  (b) hydroxy,
  (c) oxo,
  (d) $(C_1-C_6)$-alkyloxy,
  (e) $(C_1-C_6)$-S(O)$_n$—,
  (f) aryl-$(C_1-C_6)$-alkyloxy,
  (g) cyano,
  (h) nitro,
  (i) vinyl,
  (d) $NR^4R^5$,
  (k) $NR^4COC_1-C_6$-alkyl,
  (l) CHO,
  (m) $CO_2H$,
  (n) $COC_1-C_6$-alkyl,
  (o) $CO_2C_1-C_6$-alkyl,
  (p) $CONR^4R^5$,
  (q) aryl, wherein aryl is defined as phenyl or naphthyl, unsubstituted or substituted with one, two or three of the substituents selected from the group consisting of:
    (a') halo, as defined above,
    (b') hydroxy,
    (c') $(C_1-C_6)$-alkyl,
    (d') $(C_1-C_4)$-perfluoroalkyl,
    (e') $(C_1-C_6)$-alkenyl,
    (f') $(C_1-C_6)$-alkynyl,
    (g') $(C_1-C_6)$-alkyloxy,
    (h') $(C_1-C_6)$-alkyl-S(O)$_n$—,
    (i') phenyl, (j') phenoxy,
(k') cyano,
(l') nitro,
(m') $CO_2H$,
(n') $COC_1-C_6$-alkyl,
(o') $CO_2C_1-C_6$-alkyl,
(p') $CONR^4R^5$,
(q') $NR^4R^5$,
(r') $NR^4COC_1-C_6$-alkyl,
(s') $(C_1-C_6)$-alkenyloxy, and
(t') benzyloxy;
(r) heteroaryl, wherein heteroaryl is defined as an unsubstituted, monosubstituted, or disubstituted five or six membered aromatic heterocycle containing from 1 to 3 heteroatoms selected from the group consisting of O, N and S and wherein the substituents are selected from the group consisting of:
(a') halo, as defined above,
(b') hydroxy,
(c') $(C_1-C_6)$-alkyl,
(d') $(C_1-C_4)$-perfluoroalkyl,
(e') $(C_1-C_6)$-alkenyl,
(f') $(C_1-C_6)$-alkynyl,
(g') $(C_1-C_6)$-alkyloxy,
(h') $(C_1-C_6)$-alkyl-$S(O)_n$—,
(i') phenyl,
(j') phenoxy,
(k') cyano,
(l') nitro,
(m') $CO_2H$,
(n') $COC_1-C_6$-alkyl,
(o') $CO_2C_1-C_6$-alkyl,
(p') $CONR^4R^5$,
(q') $NR^4R^5$,
(r') $NR^4COC_1-C_6$-alkyl,
(s') fused benzo, and
(t') fused pyridyl group,
(s) heterocyclyl, wherein heterocyclyl is defined as a cyclic, non-aromatic moiety containing from 1 to 3 heteroatoms selected from the group consisting of O, N, and S, said heterocycle being unsubstituted or substituted with one, two or three substituents selected from the group consisting of:
(a') halo, as defined above,
(b') hydroxy,
(c') $(C_1-C_6)$-alkyl,
(d') $(C_1-C_4)$-perfluoroalkyl,
(e') $(C_1-C_6)$-alkenyl,
(f') $(C_1-C_6)$-alkynyl,
(g') $(C_1-C_6)$-alkyloxy,
(h') $(C_1-C_6)$-alkyl-$S(O)_n$—,
(i') phenyl,
(j') phenoxy,
(k') cyano,
(l') nitro,
(m') $CO_2H$,
(n') $COC_1-C_6$-alkyl,
(o') $CO_2C_1-C_6$-alkyl,
(p') $CONR^4R^5$,
(q') $NR^4R^5$,
(r') $NR^4COC_1-C_6$-alkyl, and
(s') oxo,
(t') fused benzo, and
(u') fused pyridyl group;
(4) $(C_2-C_{10})$-alkenyl, wherein alkenyl is unsubstituted or substituted with one or two substituents selected from the group consisting of:
(a) halo, wherein halo is fluoro, chloro, bromo, or iodo,
(b) hydroxy,
(c) oxo,
(d) $(C_1-C_6)$-alkyloxy,
(e) $(C_1-C_6)$-$S(O)_n$—,
(f) phenyl-$(C_1-C_6)$-alkyloxy,
(g) cyano,
(h) nitro,
(i) vinyl,
(j) $NR^4R^5$,
(k) $NR^4COC_1-C_6$-alkyl,
(l) CHO,
(m) $CO_2H$,
(n) $COC_1-C_6$-alkyl,
(o) $CO_2C_1-C_6$-alkyl,
(p) $CONR^4R^5$,
(q) aryl, wherein aryl is as defined above,
(r) heteroaryl, wherein heteroaryl is as defined above, and
(s) heterocycle, wherein the heterocycle is as defined above,
(5) $(C_2-C_{10})$-alkynyl, wherein alkynyl is unsubstituted or substituted with one or two substituents selected from the group consisting of:
(a) halo, wherein halo is fluoro, chloro, bromo, or iodo,
(b) hydroxy,
(c) oxo,
(d) $(C_1-C_6)$-alkyloxy,
(e) $(C_1-C_6)$-$S(O)_n$—,
(f) phenyl-$(C_1-C_6)$-alkyloxy,
(g) cyano,
(h) nitro,
(i) vinyl,
(j) $NR^4R^5$,
(k) $NR^4COC_1-C_6$-alkyl,
(l) CHO,
(m) $CO_2H$,
(n) $COC_1-C_6$-alkyl,
(o) $CO_2C_1-C_6$-alkyl,
(p) $CONR^4R^5$,
(q) aryl, wherein aryl is as defined above,
(r) heteroaryl, wherein heteroaryl is as defined above,
(s) heterocyclyl, wherein heterocyclyl is as defined above, and
(t) $Si(R^4)_3$,
(6) an exo-methylene group, when $R^2$ is absent or $R^{10b}$ is absent respectively; or
(7) aryl, wherein aryl is defined as phenyl or naphthyl, unsubstituted or substituted with one, two or three substituents selected from the group consisting of:
(a') halo, as defined above,
(b') hydroxy,
(c') $(C_1-C_6)$-alkyl,
(d') $(C_1-C_4)$-perfluoroalkyl,
(e') $(C_1-C_6)$-alkenyl,
(f') $(C_1-C_6)$-alkynyl,
(g') $(C_1-C_6)$-alkyloxy,
(h') $(C_1-C_6)$-alkyl-$S(O)_n$—,
(i') phenyl,
(j') phenoxy,
(k') cyano,
(l') nitro,
(m') $CO_2H$,
(n') $COC_1-C_6$-alkyl, (o') $CO_2C_1$–$C_6$-alkyl,
(p') $CONR^4R^5$,
(q') $NR^4R^5$,
(r') $NR^4COC_1$–$C_6$-alkyl,
(s') $(C_1$–$C_6)$-alkenyloxy, and
(t') benzyloxy;

$R^2$ is:
(1) H,
(2) absent when $R^1$ is oxo,
(3) absent when $R^1$ is an exo-methylene group, or
(4) OH, $R^3$ is:
(1) H, or
(2) $(C_1$–$C_{10})$-alkyl, wherein alkyl is unsubstituted or substituted with one or two substituents selected from the group consisting of:
  (a) halo, wherein halo is fluoro, chloro, bromo, iodo,
  (b) hydroxy,
  (c) oxo,
  (d) $(C_1$–$C_6)$-alkyloxy,
  (e) $(C_1$–$C_6)$-$S(O)_n$—,
  (f) aryl-$(C_1$–$C_6)$-alkyloxy,
  (g) cyano,
  (h) nitro,
  (i) vinyl,
  (j) $NR^4R^5$,
  (k) $NR^4COC_1$–$C_6$-alkyl,
  (l) CHO,
  (m) $CO_2H$,
  (n) $COC_1$–$C_6$-alkyl,
  (o) $CO_2C_1$–$C_6$-alkyl,
  (p) $CONR^4R^5$,
  (q) aryl, wherein aryl is defined as phenyl or naphthyl, unsubstituted or substituted with one, two or three of the substituents selected from the group consisting of:
    (a') halo, as defined above,
    (b') hydroxy,
    (c') $(C_1$–$C_6)$-alkyl,
    (d') $(C_1$–$C_4)$-perfluoroalkyl,
    (e') $(C_1$–$C_6)$-alkenyl,
    (f') $(C_1$–$C_6)$-alkynyl,
    (g') $(C_1$–$C_6)$-alkyloxy,
    (h') $(C_1$–$C_6)$-alkyl-$S(O)_n$—,
    (i') phenyl,
    (j') phenoxy,
    (k') cyano,
    (l') nitro,
    (m') $CO_2H$,
    (n') $COC_1$–$C_6$-alkyl,
    (o') $CO_2C_1$–$C_6$-alkyl,
    (p') $CONR^4R^5$,
    (q') $NR^4R^5$, and
    (r') $NR^4COC_1$–$C_6$-alkyl,
  (r) heteroaryl, wherein heteroaryl is defined as an unsubstituted, monosubstituted, or disubstituted five or six membered aromatic heterocycle containing from 1 to 3 heteroatoms selected from the group consisting of O, N and S and wherein the substituents are members selected from the group consisting of:
    (a') halo, as defined above,
    (b') hydroxy,
    (c') $(C_1$–$C_6)$-alkyl,
    (d') $(C_1$–$C_4)$-perfluoroalkyl,
    (e') $(C_1$–$C_6)$-alkenyl,
    (f') $(C_1$–$C_6)$-alkynyl,
    (g') $(C_1$–$C_6)$-alkyloxy,
    (h') $(C_1$–$C_6)$-alkyl-$S(O)_n$—,
    (i') phenyl,
    (j') phenoxy,
    (k') cyano,
    (l') nitro,
    (m') $CO_2H$,
    (n') $COC_1$–$C_6$-alkyl,
    (o') $CO_2C_1$–$C_6$-alkyl,
    (p') $CONR^4R^5$,
    (q') $NR^4R^5$,
    (r') $NR^4COC_1$–$C_6$-alkyl, and
    (s') fused benzo or pyridyl group,
  (s) heterocyclyl, wherein heterocyclyl is defined as a cyclic, non-aromatic moiety containing from 1 to 3 heteroatoms selected from the group consisting of O, N, and S, said heterocycle being unsubstituted or substituted with one, two or three substituents selected from the group consisting of:
    (a') halo, as defined above,
    (b') hydroxy,
    (c') $(C_1$–$C_6)$-alkyl,
    (d') $(C_1$–$C_4)$-perfluoroalkyl,
    (e') $(C_1$–$C_6)$-alkenyl,
    (f') $(C_1$–$C_6)$-alkynyl,
    (g') $(C_1$–$C_6)$-alkyloxy,
    (h') $(C_1$–$C_6)$-alkyl-$S(O)_n$—,
    (i') phenyl,
    (j') phenoxy,
    (k') cyano,
    (l') nitro,
    (m') $CO_2H$,
    (n') $COC_1$–$C_6$-alkyl,
    (o') $CO_2C_1$–$C_6$-alkyl,
    (p') $CONR^4R^5$,
    (q') $NR^4R^5$,
    (r') $NR^4COC_1$–$C_6$-alkyl, and
    (s') oxo,
    (t') fused benzo, and
    (u') fused pyridyl group;
  (t) $Si(R^4)_3$,
(3) $(C_2$–$C_{10})$-alkenyl, wherein alkenyl is unsubstituted or substituted with one or two substituents selected from the group consisting of:
  (a) halo, wherein halo is fluoro, chloro, bromo, or iodo,
  (b) hydroxy,
  (c) oxo,
  (d) $(C_1$–$C_6)$-alkyloxy,
  (e) $(C_1$–$C_6)$-$S(O)_n$—,
  (f) phenyl-$(C_1$–$C_6)$-alkyloxy,
  (g) cyano,
  (h) nitro,
  (i) vinyl,
  (j) $NR^4R^5$,
  (k) $NR^4COC_1$–$C_6$-alkyl,
  (l) CHO,
  (m) $CO_2H$,
  (n) $COC_1$–$C_6$-alkyl,
  (o) $CO_2C_1$–$C_6$-alkyl,
  (p) $CONR^4R^5$,
  (q) aryl, wherein aryl is as defined above,
  (r) heteroaryl, wherein heteroaryl is as defined above, and
  (s) heterocyclyl, wherein heterocyclyl is as defined above;
(4) $(C_2$–$C_{10})$-alkynyl, wherein alkynyl is unsubstituted or substituted with one or two substituents selected from the group consisting of:

(a) halo, wherein halo is fluoro, chloro, bromo, or iodo,
(b) hydroxy,
(c) oxo,
(d) $(C_1-C_6)$-alkyloxy,
(e) $(C_1-C_6)$-S(O)$_n$—,
(f) phenyl-$(C_1-C_6)$-alkyloxy,
(g) cyano,
(h) nitro,
(i) vinyl,
(j) $NR^4R^5$,
(k) $NR^4COC_1-C_6$-alkyl,
(l) CHO,
(m) $CO_2H$,
(n) $COC_1-C_6$-alkyl,
(o) $CO_2C_1-C_6$-alkyl,
(p) $CONR^4R^5$,
(q) aryl, wherein aryl is as defined above,
(r) heteroaryl, wherein heteroaryl is as defined above, and
(s) heterocyclyl, wherein heterocyclyl is as defined above; or
(5) cyano;
$R^4$ and $R^5$ are independently:
(1) hydrogen,
(2) $C_1-C_6$ alkyl, or
(3) aryl, wherein aryl is defined above,
$R^6$ is:
(1) hydrogen,
(2) oxo and a is a single bond,
(3) O[(C=O)O$_r$]$_s$R$^{11}$,
(4) O[(C=O)O$_r$]$_s$aryl, aryl as defined above,
(5) O[(C=O)O$_r$]$_s$heteroaryl, heteroaryl as defined above,
(6) OC(=O)NR$^{11}$R$^{12}$,
(7) NR$^{11}$R$^{12}$, or
(8) absent, when a is a double bond;
$R^7$, $R^8$ and $R^9$ are independently selected from the group consisting of:
(1) hydrogen,
(2) oxo,
(3) O[(C=O)O$_r$]$_s$R$^{11}$,
(4) O[(C=O)O$_r$]$_s$aryl, aryl as defined above,
(5) O[(C=O)O$_r$]$_s$heteroaryl, heteroaryl as defined above,
(6) OC(=O) NR$^{11}$R$^{12}$ and
(7) NR$^{11}$R$^{12}$,
$R^{10b}$ is:
(1) H,
(2) absent when $R^{10a}$ is oxo,
(3) an exo-methylene group, when $R^2$ is absent or $R^{10b}$ is absent respectively, or
(4) OH; and
$R^{11}$ and $R^{12}$ are independently chosen from the group consisting of:
(1) H, and
(2) $(C_1-C_6)$-alkyl, wherein alkyl is unsubstituted or substituted with one, two or three substituents selected from the group consisting of: Br, Cl, F, I, $(C_1-C_6)$-alkoxy, vinyl, cyano, oxo, nitro, hydroxy, CHO, $CO_2H$, $COC_1-C_6$-alkyl, $CO_2C_1-C_6$-alkyl, $CONR^4R^5$, $NR^4R^5$, $NR^4COC_1-C_6$-alkyl, aryl, wherein aryl is defined as phenyl or naphthyl, unsubstituted or substituted with one, two or three substituents selected from the group consisting of: Br, Cl, F, I, $(C_1-C_6)$-alkoxy, phenyl, phenoxy, cyano, oxo, nitro, hydroxy, CHO, $CO_2H$, $COC_1-C_6$-alkyl, $CO_2C_1-C_6$-alkyl, $CONR^4R^5$, $NR^4R^5$, $NR^4COC_1-C_6$-alkyl and any two of adjacent substituents can be joined to form a 5-, 6- or 7-membered fused ring said ring containing 1 or 2 oxygen atoms and the remainder carbon atoms, heteroaryl, wherein heteroaryl is defined as a 5 or 6-membered ring substituted with one and two heteroatoms selected from O, S, N, unsubstituted or substituted with one, two or three substituents selected from the group consisting of: Br, Cl, F, I, $(C_1-C_6)$-alkoxy, cyano, oxo, nitro, hydroxy, CHO, $CO_2H$, $COC_1-C_6$-alkyl, $CO_2C_1-C_6$-alkyl, $CONR^4R^5$, $NR^4R^5$, $NR^4COC_1-C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring.

A subembodiment of the invention are compounds of structural Formula 1, wherein:
$R^{10a}$ is further defined as:
(1) H,
(2) =O, when $R^{10b}$ is absent,
(3) $(C_1-C_4)$-alkyl, wherein alkyl is unsubstituted or substituted with one or two substituents selected from the group consisting of:
(a) halo, wherein halo is fluoro, chloro, bromo, or iodo,
(b) hydroxy,
(c) oxo,
(d) $(C_1-C_3)$-alkyloxy,
(e) CHO,
(g) $CO(C_1-C_3)$-alkyl,
(i) aryl, wherein aryl is defined as phenyl or naphthyl, unsubstituted or substituted with one or two of the substituents selected from the group consisting of:
(a') halo, as defined above,
(b') hydroxy,
(c') $(C_1-C_6)$-alkyl,
(d') $(C_1-C_4)$-perfluoroalkyl,
(e') $(C_1-C_6)$-alkenyl,
(f') $(C_1-C_6)$-alkynyl,
(g') $(C_1-C_6)$-alkyloxy,
(h') $(C_1-C_6)$-alkyl-S(O)$_n$—,
(i') phenyl,
(j') phenoxy,
(k') cyano,
(l') nitro,
(m') $CO_2H$,
(n') $COC_1-C_6$-alkyl,
(o') $CO_2C_1-C_6$-alkyl,
(p') $CONR^4R^5$,
(q') $NR^4R^5$,
(r') $NR^4COC_1-C_6$-alkyl,
(s') $(C_1-C_6)$-alkenyloxy, and
(t') benzyloxy;
(j) heteroaryl, wherein heteroaryl is defined as pyridyl or thienyl,
(4) $(C_2-C_4)$-alkenyl, wherein alkenyl is unsubstituted or substituted with aryl, wherein aryl is as defined above;
(5) $(C_2-C_3)$-alkynyl, wherein alkynyl is unsubstituted or substituted with phenyl or $Si(R^4)_3$, or
(6) an exo-methylene group, when $R^{10b}$ is absent.

Another subembodiment of the invention are the compounds of structural Formula I, wherein:

$R^3$ is further defined as:
(1) H, or
(2) $(C_1-C_3)$-alkyl, wherein alkyl is unsubstituted or substituted with one or two substituents selected from the group consisting of:
  (a) halo, wherein halo is fluoro, chloro, bromo, iodo,
  (b) hydroxy,
  (c) oxo,
  (d) $(C_1-C_6)$-alkyloxy,
  (e) $(C_1-C_6)$-S(O)$_n$—,
  (f) aryl-$(C_1-C_6)$-alkyloxy,
  (g) cyano,
  (h) nitro,
  (i) vinyl,
  (j) $NR^4R^5$,
  (k) $NR^4COC_1-C_6$-alkyl,
  (l) CHO,
  (m) $CO_2H$,
  (n) $COC_1-C_6$-alkyl,
  (o) $CO_2C_1-C_6$-alkyl,
  (p) $CONR^4R^5$,
  (q) aryl, wherein aryl is defined as phenyl or naphthyl, unsubstituted or substituted with one, two or three of the substituents selected from the group consisting of:
    (a') halo, as defined above,
    (b') hydroxy,
    (c') $(C_1-C_6)$-alkyl,
    (d') $(C_1-C_4)$-perfluoroalkyl,
    (e') $(C_1-C_6)$-alkenyl,
    (f') $(C_1-C_6)$-alkynyl,
    (g') $(C_1-C_6)$-alkyloxy,
    (h') $(C_1-C_6)$-alkyl-S(O)$_n$—,
    (i') phenyl,
    (j') phenoxy,
    (k') cyano,
    (l') nitro,
    (m') $CO_2H$,
    (n') $COC_1-C_6$-alkyl,
    (o') $CO_2C_1-C_6$-alkyl,
    (p') $CONR^4R^5$,
    (g') $NR^4R^5$, and
    (r') $NR^4COC_1-C_6$-alkyl,
  (r) $Si(R^4)_3$,
(3) $(C_2-C_3)$-alkenyl, wherein alkenyl is unsubstituted or substituted with one or two substituents selected from the group consisting of:
  (a) halo, wherein halo is fluoro, chloro, bromo, or iodo,
  (b) hydroxy,
  (c) oxo,
  (d) $(C_1-C_6)$-alkyloxy,
  (e) $(C_1-C_6)$-S(O)$_n$—,
  (f) phenyl-$(C_1-C_6)$-alkyloxy,
  (g) cyano,
  (h) nitro,
  (i) vinyl,
  (j) $NR^4R^5$,
  (k) $NR^4COC_1-C_6$-alkyl,
  (l) CHO,
  (m) $CO_2H$,
  (n) $COC_1-C_6$-alkyl,
  (o) $CO_2C_1-C_6$-alkyl,
  (p) $CONR^4R^5$,
  (q) aryl, wherein aryl is as defined above,
  (r) heteroaryl, wherein heteroaryl is as defined above, and
  (s) heterocyclyl, wherein heterocyclyl is as defined above;
(4) $(C_2-C_3)$-alkynyl, wherein alkynyl is unsubstituted or substituted with one or two substituents selected from the group consisting of:
  (a) halo, wherein halo is fluoro, chloro, bromo, or iodo,
  (b) hydroxy,
  (c) oxo,
  (d) $(C_1-C_6)$-alkyloxy,
  (e) $(C_1-C_6)$-S(O)$_n$—,
  (f) phenyl-$(C_1-C_6)$-alkyloxy,
  (g) cyano,
  (h) nitro,
  (i) vinyl,
  (j) $NR^4R^5$,
  (k) $NR^4COC_1-C_6$-alkyl,
  (l) CHO,
  (m) $CO_2H$,
  (n) $COC_1-C_6$-alkyl,
  (o) $CO_2C_1-C_6$-alkyl,
  (p) $CONR^4R^5$,
  (q) aryl, wherein aryl is as defined above,
  (r) heteroaryl, wherein heteroaryl is as defined above, and
  (s) heterocyclyl, wherein heterocyclyl is as defined above; or
(5) cyano;

$R^4$ and $R^5$ are further defined independently as:
(1) hydrogen,
(2) $C_1-C_3$ alkyl, or
(3) phenyl, $R^6$ is further defined as:
(1) hydrogen,
(2) oxo and a is a single bond,
(3) $O(C=O)R^{11}$, or
(4) absent, when a is a double bond;

$R^7$, $R^8$ and $R^9$ are further defined as independently selected from the group consisting of:
(1) hydrogen,
(2) oxo,
(3) $O(C=O)R^{11}$; and $R^{11}$ and $R^{12}$ are further defined as independently chosen from the group consisting of:
(1) H, and
(2) $(C_1-C_3)$-alkyl.

A preferred embodiment of the invention is wherein:
$R^1$ is further defined as:
(1) H,
(2) =O, when $R^2$ is absent,
(3) $(C_1-C_8)$-alkyl, wherein alkyl is unsubstituted or substituted with one or two substituents selected from the group consisting of:
  (a) halo, wherein halo is fluoro, chloro, bromo, or iodo,
  (b) hydroxy,
  (c) oxo,
  (d) $(C_1-C_3)$-alkyloxy,
  (e) CHO,
  (g) $CO(C_1-C_3)$-alkyl,
  (i) aryl, wherein aryl is defined as phenyl or naphthyl, unsubstituted or substituted with one, two or three of the substituents selected from the group consisting of:
    (a') halo, as defined above,
    (b') hydroxy, (c') $(C_1-C_6)$-alkyl,
(d') $(C_1-C_4)$-perfluoroalkyl,
(e') $(C_1-C_6)$-alkenyl,
(f') $(C_1-C_6)$-alkynyl,
(g') $(C_1-C_6)$-alkyloxy,
(h') $(C_1-C_6)$-alkyl-S(O)$_n$—,
(i') phenyl,
(j') phenoxy,
(k') cyano,
(l') nitro,
(m') CO$_2$H,
(n') COC$_1$–C$_6$-alkyl,
(o') CO$_2$C$_1$–C$_6$-alkyl,
(p') CONR$^4$R$^5$,
(q') NR$^4$R$^5$,
(r') NR$^4$COC$_1$–C$_6$-alkyl,
(s') $(C_1-C_6)$-alkenyloxy, and
(t') benzyloxy;
(j) heteroaryl, wherein heteroaryl is defined as pyridyl or thienyl,
(4) $(C_2-C_6)$-alkenyl, wherein alkenyl is unsubstituted or substituted with aryl, wherein aryl is as defined above; and
(5) $(C_2-C_3)$-alkynyl, wherein alkynyl is unsubstituted or substituted with phenyl or Si(R$^4$)$_3$, or
(6) an exo-methylene group, when R$^2$ is absent;
R$^3$ is further defined as:
(1) H, or
(2) $(C_1-C_3)$-alkyl, wherein alkyl is unsubstituted or substituted with phenyl or Si(R$^4$)$_3$,
(3) $(C_2-C_3)$-alkenyl, wherein alkenyl is unsubstituted or substituted with aryl, wherein aryl is defined as phenyl or naphthyl, unsubstituted or substituted with one, two or three substituents selected from the group consisting of:
(a') halo, as defined above,
(b') hydroxy,
(c') $(C_1-C_6)$-alkyl,
(d') $(C_1-C_4)$-perfluoroalkyl,
(e') $(C_1-C_6)$-alkenyl,
(f') $(C_1-C_6)$-alkynyl,
(g') $(C_1-C_6)$-alkyloxy,
(h') $(C_1-C_6)$-alkyl-S(O)$_n$—,
(i') phenyl,
(j') phenoxy,
(k') cyano,
(l') nitro,
(m') CO$_2$H,
(n') COC$_1$–C$_6$-alkyl,
(o') CO$_2$C$_1$–C$_6$-alkyl,
(p') CONR$^4$R$^5$,
(q') NR$^4$R$^5$,
(r') NR$^4$COC$_1$–C$_6$-alkyl,
(s') $(C_1-C_6)$-alkenyloxy, and
(t') benzyloxy;
(4) cyano;
R$^4$ and R$^5$ are further defined independently as:
(1) hydrogen,
(2) C$_1$–C$_3$ alkyl, or
(3) phenyl,
R$^6$ is further defined as:
(1) hydrogen,
(2) oxo and a is a single bond,
(3) O(C=O)R$^{11}$, or
(4) absent, when a is a double bond;
R$^7$, R$^8$ and R$^9$ are further defined as independently selected from the group consisting of:

(1) hydrogen,
(2) oxo, and
(3) O(C=O)R$^{11}$; and
R$^{11}$ and R$^{12}$ are further defined as independently chosen from the group consisting of:
(1) H, and
(2) $(C_1-C_3)$-alkyl.
Yet another preferred embodiment of the invention is wherein R$^{10a}$ and R$^{10b}$ are further defined as H.
A most preferred embodiment is a compound selected from the group consisting of:

[3a-S-3aa,3bb,5aa,9b,9ab,10a,11a,11aa]-11a-(1-R-acetoxyethyl)-6-oxo-9,10,11-triacetoxy-3b,7,9a-trimethyl-1,3,3a,3b,4,5,5a,6,9,9a,9b,10,11,11a-tetradecahydrophenanthro[1,2-c]furan;

[3a-S-3aa,3bb,5aa,9b,9ab,10a,11a,11aa]-11a-11a-(1-R-acetoxyethyl)-6-benzyl-6-hydroxy-9,10,11-triacetoxy-3b,7,9a-trimethyl-1,3,3a,3b,4,5,5a,6,9,9a,9b,10,11,11a-tetradecahydrophenanthro[1,2-c]furan;

[3a-S-3aa,3bb,5aa,9b,9ab,10a,11a,11aa]-11a-(1-R-acetoxyethyl)-6-hydroxy-9,10,11-triacetoxy-3b,7,9a-trimethyl-1,3,3a,3b,4,5,5a,6,9,9a,9b,10,11,11a-tetradecahydrophenanthro[1,2-c]furan;

[3a-S-3aa,3bb,5aa,9b,9ab,10a,11a,11aa]-11a-(1-R-acetoxyethyl)-6-(3-phenyl-n-propyl)-6-hydroxy-9,10,11-triacetoxy-3b,7,9a-trimethyl-1,3,3a,3b,4,5,5a,6,9,9a,9b,10,11,11a-tetradecahydrophenanthro[1,2-c]furan;

[3a-S-3aa,3bb,5aa,9b,9ab,10a,11a,11aa]-11a-(1-R-acetoxyethyl)-6-(2-phenethyl)-6-hydroxy-9,10,11-triacetoxy-3b,7,9a-trimethyl-1,3,3a,3b,4,5,5a,6,9,9a,9b,10,11,11a-tetradecahydrophenanthro[1,2-c]furan;

[3a-S-3aa,3bb,5aa,9b,9ab,10a,11a,11aa]-11a-(1-R-acetoxyethyl)-6-(2-phenethyl)-6-hydroxy-9,10,11-triacetoxy-3b,7,9a-trimethyl-1,3,3a,3b,4,5,5a,6,7,8,9,9a,9b,10,11,11a-hexadecahydrophenanthro[1,2-c]furan;

[3a-S-3aa,3bb,5aa,9b,9ab,10a,11a,11aa]-11a-(1-R-acetoxyethyl)-6-(2-phenethyl)-9,10,11-triacetoxy-3b,7,9a-trimethyl-1,3,3a,3b,4,5,7,8,9,9a,9b,10,11,11a-tetradecahydrophenanthro[1,2-c]furan;

[3a-S-3aa,3bb,5aa,9b,9ab,10a,11a,11aa]-11a-(1-R-acetoxyethyl)-6-(2-(2-methoxyphenyl)ethyl)-6-hydroxy-9,10,11-triacetoxy-3b,7,9a-trimethyl-1,3,3a,3b,4,5,5a,6,9,9a,9b,10,11,11a-tetradecahydrophenanthro[1,2-c]furan;

[3a-S-3aa,3bb,5aa,9b,9ab,10a,11a,11aa]-11a-(1-R-acetoxyethyl)-6-(2-(2-ethoxyphenyl)ethyl))-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2-n -butyloxyphenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2-allyloxyphenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2-benzyloxyphenyl)ethyl)-6-hydroxy-9,10,11-triacetoxy-3b,7,9a-trimethyl- 1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(but-3-en-1-yl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(4-dimethyl-pent-3-en-1-yl)-6-hydroxy- 9,10,11-triacetoxy-3b,7,9a-trimethyl-1,3,3a,3b,4,5,5a,6, 9,9a,9b,10,11,11a-tetradecahydro phenanthro[1,2-c] furan;

[3a-S-3aa,3bb,5aa,9b,9ab,10a,11a,11aa]-11a-(1-R-acetoxyethyl)-6-(2-(2-fluorophenyl)ethyl)-6-hydroxy-9, 10,11-triacetoxy-3b,7,9a-trimethyl-1,3,3a,3b,4,5,5a,6,9, 9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2,6-difluorophenyl)ethyl)-6-hydroxy-9,10,11-triacetoxy-3b,7,9a-trimethyl-1,3,3a,3b, 4,5,5a,6,9,9a,9b,10,11,11a-tetradecahydro phenanthro[1, 2-c]furan;

[3a-S-3aa,3bb,5aa,9b,9ab,10a,11a,11aa]-11a-(1-R-acetoxyethyl)-6-(2-(2-chlorophenyl)ethyl)-6-hydroxy-9, 10,11-triacetoxy-3b,7,9a-trimethyl-1,3,3a,3b,4,5,5a,6,9, 9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(3-chlorophenyl)ethyl)-6-hydroxy-9, 10,11-triacetoxy-3b,7,9a-trimethyl-1,3,3a,3b,4,5,5a,6,9, 9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(4-chlorophenyl)ethyl)-6-hydroxy-9, 10,11-triacetoxy-3b,7,9a-trimethyl-1,3,3a,3b,4,5,5a,6,9, 9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(3,4-dichlorophenyl)ethyl)-6-hydroxy-9,10,11-triacetoxy-3b,7,9a-trimethyl-1,3,3a,3b, 4,5,5a,6,9,9a,9b,10,11,11a-tetradecahydro phenanthro[1, 2-c]furan;

[3a-S-3aa,3bb,5aa,9b,9ab,10a,11a,11aa]-11a-(1-R-acetoxyethyl)-6-(2-(2-methylphenyl)ethyl)-6-hydroxy-9, 10,11-triacetoxy-3b,7,9a-trimethyl-1,3,3a,3b,4,5,5a,6,9, 9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(3-methylphenyl)ethyl)-6-hydroxy-9, 10,11-triacetoxy-3b,7,9a-trimethyl-1,3,3a,3b,4,5,5a,6,9, 9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(4-methylphenyl)ethyl)-6-hydroxy-9, 10,11-triacetoxy-3b,7,9a-trimethyl-1,3,3a,3b,4,5,5a,6,9, 9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2-trifluoromethylphenyl)ethyl)-6-hydroxy-9,10,11-triacetoxy-3b,7,9a-trimethyl-1,3,3a,3b, 4,5,5a,6,9,9a,9b,10,11,11a-tetradecahydro phenanthro[1, 2-c]furan;

[3a-S-3aa,3bb,5aa,9b,9ab,10a,11a,11aa]-11a-(1-R-acetoxyethyl)-6-(2-(3-trifluoromethylphenyl)ethyl)-6-hydroxy-9,10,11-triacetoxy-3b, 7,9a-trimethyl-1,3,3a,3b, 4,5,5a,6,9,9a,9b,10,11,11a-tetradecahydro phenanthro[1, 2-c]furan;

[3a-S-3aa,3bb,5aa,9b,9ab,10a,11a,11aa]-11a-(1-R-acetoxyethyl)-6-(2-naphth-2-ylethyl)-6-hydroxy-9,10,11-triacetoxy-3b,7,9a-trimethyl-1,3,3a,3b,4,5,5a,6,9,9a,9b, 10,11,11a-tetradecahydro phenanthro[1,2-c]furan;

[3a-S-3aa,3bb,5aa,9b,9ab,10a,11a,11aa]-11a-(1-R-acetoxyethyl)-6-(2-naphth-1-ylethyl)-6-hydroxy-9,10,11-triacetoxy-3b,7,9a-trimethyl-1,3,3a,3b,4,5,5a,6,9,9a,9b, 10,11,11a-tetradecahydro phenanthro[1,2-c]furan;

[3a-S-3aa,3bb,5aa,9b,9ab,10a,11a,11aa]-11a-(1-R-acetoxyethyl)-6-(2methoxyphenyl)ethyl))-6-hydroxy-9, 10,11-triacetoxy-3b,7,9a-trimethyl-1,3,3a,3b,4,5,5a,6,9, 9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(4-methoxyphenyl)ethyl))-6-hydroxy-9,10,11-triacetoxy-3b,7,9a-trimethyl-1,3,3a,3b,4,5,5a,6, 9,9a,9b,10,11,11a-tetradecahydro phenanthro[1,2-c] furan;

[3a-S-3aa,3bb,5aa,9b,9ab,10a,11a,11aa]-11a-(1-R-acetoxyethyl)-6-(2(2,3-dimethoxyphenyl)ethyl))-6-hydroxy-9,10,11-triacetoxy-3b,7,9a-trimethyl-1,3,3a,3b, 4,5,5a,6,9,9a,9b,10,11,11a-tetradecahydro phenanthro[1, 2-c]furan;

[3a-S-3aa,3bb,5aa,9b,9ab,10a,11a,11aa]-11a-(1-R-acetoxyethyl)-6-(2-(3,4-dimethoxyphenyl)ethyl))-6-hydroxy-9,10,11-triacetoxy-3b,7,9a-trimethyl-1,3,3a,3b, 4,5,5a,6,9,9a,9b,10,11,11a-tetradecahydro phenanthro[1, 2-c]furan;

[3a-S-3aa,3bb,5aa,9b,9ab,10a,11a,11aa]-11a-(1-R-acetoxyethyl)-6-(2-(2,5-dimethoxyphenyl)ethyl))-6-hydroxy-9,10,11-triacetoxy-3b,7,9a-trimethyl-1,3,3a,3b, 4,5,5a,6,9,9a,9b,10,11,11a-tetradecahydro phenanthro[1, 2-c]furan;

[3a-S-3aa,3bb,5aa,9b,9ab,10a,11a,11aa]-11a-(1-R-acetoxyethyl)-6-(2-(3,5-dimethoxyphenyl)ethyl)-6-hydroxy-9,10,11-triacetoxy-3b,7,9a-trimethyl-1,3,3a,3b, 4,5,5a,6,9,9a,9b,10,11,11a-tetradecahydro phenanthro[1, 2-c]furan;

[3a-S-3aa,3bb,5aa,9b,9ab,10a,11a,11aa]-11a-(1-R-acetoxyethyl)-6-(2-(3,4-methylenedioxyphenyl)ethyl)-6-hydroxy-9,10,11-triacetoxy-3b,7,9a-trimethyl-1,3,3a,3b, 4,5,5a,6,9,9a,9b,10,11,11a-tetradecahydro phenanthro[1, 2-c]furan;

[3a-S-3aa,3bb,5aa,9b,9ab,10a,11a,11aa]-11a-(1-R-acetoxyethyl)-6-(2-(2,3-methylenedioxyphenyl)ethyl)-6-hydroxy-9,10,11-triacetoxy-3b,7,9a-trimethyl-1,3,3a,3b, 4,5,5a,6,9,9a,9b,10,11,11a-tetradecahydro phenanthro[1, 2-c]furan;

[3a-S-3aa,3bb,5aa,9b,9ab,10a,11a,11aa]-11a-(1-R-acetoxyethyl)-6-(2-(4-dimethylaminophenyl)ethyl)-6-hydroxy-9,10,11-triacetoxy-3b,7,9a-trimethyl-1,3,3a,3b, 4,5,5a,6,9,9a,9b,10,11,11a-tetradecahydro phenanthro[1, 2-c]furan;

[3a-S-3aa,3bb,5aa,9b,9ab,10a,11a,11aa]-11a-(1-R-acetoxyethyl)-6-(2,2-diphenylethyl)-6-hydroxy-9,10,11-triacetoxy-3b,7,9a-trimethyl-1,3,3a,3b,4,5,5a,6,9,9a,9b, 10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2-methoxy-5-methylphenyl)ethyl)-6-hydroxy-9,10,11-triacetoxy-3b, 7,9a-trimethyl-1,3,3a,3b, 4,5,5a,6,9,9a,9b,10,11,11a-tetradecahydro phenanthro[1, 2-c]furan;

[3a-S-3aa,3bb,5aa,9b,9ab,10a,11a,11aa]-11a-(1-R-acetoxyethyl)-6-(2-(thien-2-yl)ethyl)-6-hydroxy-9,10,11-triacetoxy-3b,7,9a-trimethyl-1,3,3a, 3b,4,5,5a,6,9,9a,9b, 10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2,6-dimethoxylphenyl)ethyl)-6-hydroxy-9,10,11-triacetoxy-3b,7,9a-trimethyl-1,3,3a,3b, 4,5,5a,6,9,9a,9b,10,11,11a-tetradecahydro phenanthro[1, 2-c]furan;

[3a-S-3aa,3bb,5aa,9b,9ab,10a,11a,11aa]-11a-(1-R-acetoxyethyl)-6-(2-phenyl-propyl)-6-hydroxy-9,10,11-triacetoxy-3b,7,9a-trimethyl-1,3,3a,3b,4,5,5a,6,9,9a,9b, 10,11,11a-tetradecahydro phenanthro[1,2-c]furan;

[3a-S-3aa,3bb,5aa,9b,9ab,10a,11a,11aa]-11a-(1-R-acetoxyethyl)-6-(2-phenyl-2-methylpropyl)-6-hydroxy-9, 10,11-triacetoxy-3b,7,9a-trimethyl-1,3,3a,3b,4,5,5a,6,9, 9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-hydroxyphenylethyl)-6-hydroxy-9,10, 11-triacetoxy-3b,7,9a-trimethyl-1,3,3a,3b,4,5,5a,6,9,9a, 9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(S)-phenylpropyl)-6-hydroxy-9,10, 11-triacetoxy-3b,7,9a-trimethyl-1,3,3a, 3b,4,5,5a,6,9,9a, 9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-phenylprop-2-enyl)-6-hydroxy-9,10, 11-triacetoxy-3b,7,9a-trimethyl-1,3,3a,3b,4,5,5a,6,9,9a, 9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(R)-phenylpropyl)-6-hydroxy-9,10, 11-triacetoxy-3b,7,9a-trimethyl-1,3,3a,3b,4,5,5a,6,9,9a, 9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2-methoxyphenyl)prop-2-enyl)-6-hydroxy-9,10,11-triacetoxy-3b,7,9a-trimethyl-1,3,3a,3b, 4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2-ethylmercaptophenyl)prop-2-enyl)-6-hydroxy-9,10,11 -triacetoxy-3b,7,9a-trimethyl-1, 3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2-ethylphenyl)prop-2-enyl)-6-hydroxy-9,10,11-triacetoxy-3b,7,9a-trimethyl-1,3,3a,3b, 4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2-methylmercaptophenyl)prop-2-enyl)-6-hydroxy-9,10,11-triacetoxy-3b,7,9a-trimethyl-1, 3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2-n-butylmercaptophenyl)prop-2-enyl)-6-hydroxy-9,10,11-triacetoxy-3b,7,9a-trimethyl-1, 3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2-vinylphenyl)prop-2-enyl)-6-hydroxy-9,10,11-triacetoxy-3b,7,9a-trimethyl-1,3,3a,3b, 4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(S)-(2-ethylphenyl)propyl)-6-hydroxy-9,10,11-triacetoxy-3b,7,9a-trimethyl-1,3,3a,3b, 4,5,5a,6,9,9a,9b,10,11,11a-tetradecahydro phenanthro[1,2-c]furan; and

[3a-S-3aa,3bb,5aa,9b,9ab,10a,11a,11aa]-11a-(1-R-acetoxyethyl)-6(2-(S)-(–)-(2-methoxyphenyl)propyl)-6-hydroxy-9,10,11-triacetoxy-3b,7,9a-trimethyl-1,3,3a,3b, 4,5,5a,6,9,9a,9b,10,11,11a-tetradecahydro phenanthro[1,2-c]furan.

The compounds of the present invention have asymmetric centers and this invention includes all of the optical isomers and mixtures thereof.

In addition compounds with carbon-carbon double bonds may occur in Z- and E-forms with all isomeric forms of the compounds being included in the present invention.

As used herein, the term "alkyl" includes those alkyl groups of a designated number of carbon atoms of either a straight, branched, or cyclic configuration. Examples of "alkyl" include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy.

"Alkenyl" is intended to include hydrocarbon chains of a specified number of carbon atoms of either a straight- or branched-configuration and at least one unsaturation, which may occur at any point along the chain, such as ethenyl, propenyl, butenyl, pentenyl, dimethyl pentenyl, and the like, and includes E and Z forms, where applicable. "Halogen", as used herein, means fluoro, chloro, bromo and iodo.

The term "aryl" is defined as a phenyl or naphthyl ring which is optionally substituted with the substituents listed above at any available carbon atoms. The aryl may also be substituted with a fused 5-, 6-, or 7-membered ring containing one or two oxygens and the remaining ring atoms being carbon, the fused 5-, 6-, or 7-ring being selected from the group consisting of: dioxolanyl, dihydrofuranyl, dihydropyranyl, and dioxanyl.

The term "heteroaryl" as utilized herein, unless specifically defined otherwise, is intended to include the following: a 5 or 6-membered ring substituted with one, two or three heteroatoms selected from O, S, N, and is unsubstituted or substituted with one, two or three substituents selected from the group consisting of: Br, Cl, F, I, $(C_1$–$C_6)$-alkoxy, cyano, nitro, hydroxy, CHO, $CO_2H$, $COC_1$–$C_6$-alkyl, $CO_2C_1$–$C_6$-alkyl, $CONR^{11}R^{12}$, $NR^{11}R^{12}$, $NR^{11}COC_1$–$C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, pyrazinyl, pyridazinyl, pyridinyl, pyrimidinyl, and pyrrolyl which are substituted or unsubstituted as defined above.

In the compounds of Formula I, the heteroaryl group may be optionally substituted with the substituents listed above at any available carbon atom or nitrogen atom (if present), but compounds bearing certain substitutents, directly substituted to a nitrogen may be relatively unstable and are not preferred. The heteroaryl may also be fused to a second 5-, 6-, or 7-membered ring containing one or two oxygens such as: dioxolanyl, dihydrofuranyl, dihydropyranyl, and dioxanyl.

The term "heterocyclyl" as utilized herein, unless specifically defined otherwise, is intended to include a cyclic, non-aromatic substituents containing from 1 to 3 heteroatoms selected from the group consisting of O, N, and S, said heterocyclyl substituent being itself unsubstituted or substituted with one, two or three substituents selected from the group consisting of: Br, Cl, F, I, $(C_1$–$C_6)$-alkoxy, cyano, nitro, hydroxy, CHO, $CO_2H$, $COC_1$–$C_6$-alkyl, $CO_2C_1$–$C_6$-alkyl, $CONR^1R^2$, $NR^{11}R^{12}$, $NR^{11}COC_1$–$C_6$-alkyl. Representative heterocyclyl substituents include, but are not limited to the following: piperidinyl, morpholinyl, pyrrolidinyl, tetrahydrofuranyl, imidazolinyl, piperazinyl, pyrolidine-2-one, piperidine-2-one and the like.

Pharmaceutically acceptable salts include both the metallic (inorganic) salts and organic salts; a list of which is given in *Remington's Pharmaceutical Sciences,* 17th Edition, pg. 1418 (1985). It is well known to one skilled in the art that an appropriate salt form is chosen based on physical and chemical stability, flowability, hydro-scopicity and solubility. As will be understood by those skilled in the art, pharmaceutically acceptable salts include, but are not limited to salts of inorganic acids such as hydrochloride, sulfate, phosphate, diphosphate, hydrobromide, and nitrate or salts of an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with secondary amines). Preferred salts of this invention for the reasons cited above include potassium, sodium, calcium and ammonium salts. Also included within the scope of this invention are crystal forms, hydrates and solvates of the compounds of Formula I.

REACTION SCHEME A

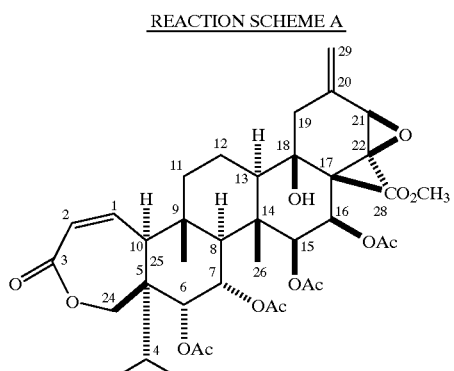

1. $O_3$
2. $NaBH_4$

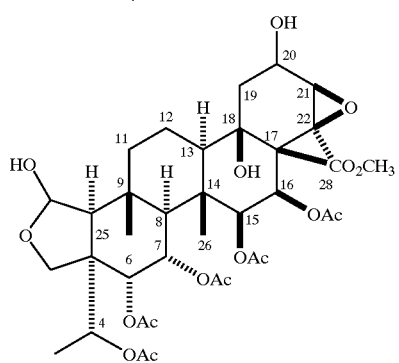

As seen in Reaction Scheme A, compound Ia [(4,6,7,15,16-pentakis(acetyloxy)-21,22-epoxy-18-hydroxy-22-methyoxycarbonyl-[6α,7α,15β,16β,21β,22β]D:A-Friedo-A-homo-27,30-dinor-24-oxaoleana-1, 20(29)-dien-3-one] is ozonized under standard conditions. Reductive workup with an agent such as sodium borohydride gives the hydroxy lactol intermediate.

REACTION SCHEME B

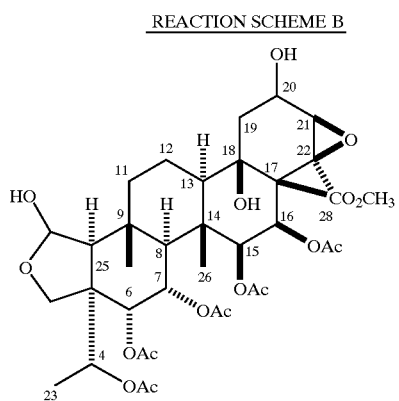

$Et_3SiH, BF_3\cdot OEt_2$

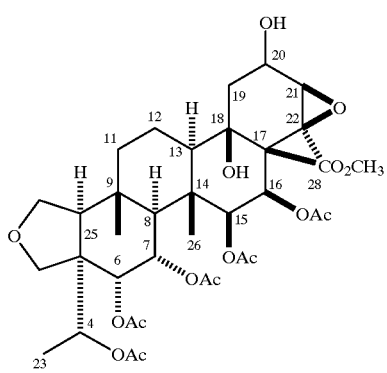

As seen in Scheme B, the lactol product of Reaction Scheme A can be reacted with triethylsilane and a Lewis acid such as borontrifluoride diethyl etherate to give the tetrahydrofuran (THF) analog.

REACTION SCHEME C

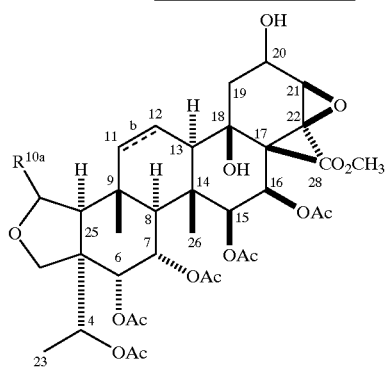

$R^{10a}$ SiMe, $BF_3\cdot OEt_2$
1. DAST
2. $(R^{10a})_3Al$

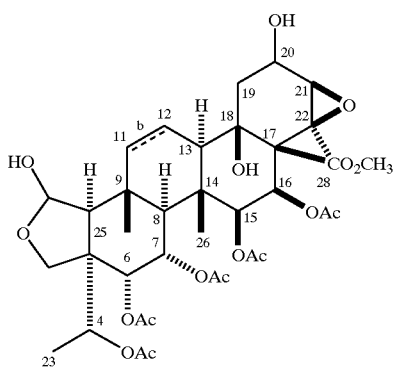

[O]

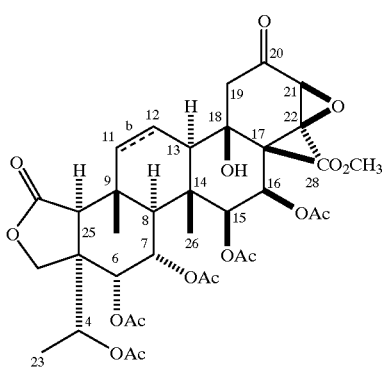

The lactol hydroxy group can be replaced as demonstrated in Scheme C with a variety of substituents (represented as $R^{10a}$).

Reaction with allyltrimethyl silane and a Lewis acid such as boron trifluoride etherate ($BF_3 \cdot OEt_2$) in dichloromethane gives the allyl analog ($R^{10a}$=allyl $R^{10b}$=H) which can be modified in a variety of ways that are known to the practitioner. Alternatively, the lactol can be reacted with diethylaminosulfur trifluoride (DAST) in a basic solvent such as collidine to give the fluoro analog ($R^{10a}$=F) which can be reacted with trisubstituted aluminum reagents such as triethyl aluminum to give the ethyl derivative, for example.

The hydroxy lactol derivative can be oxidized to its keto lactone derivative by use of a variety of reagents, including pyridinium chlorochromate (PCC).

REACTION SCHEME D

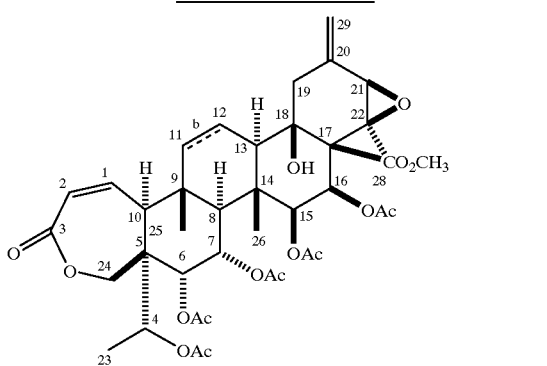

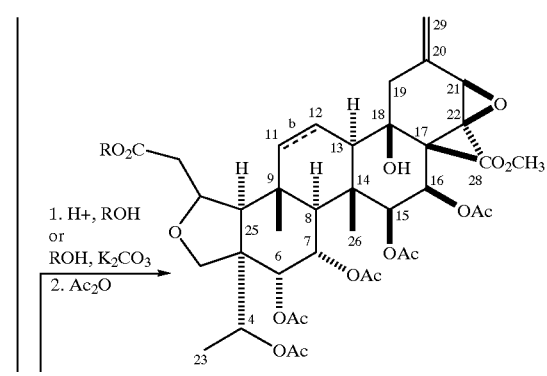

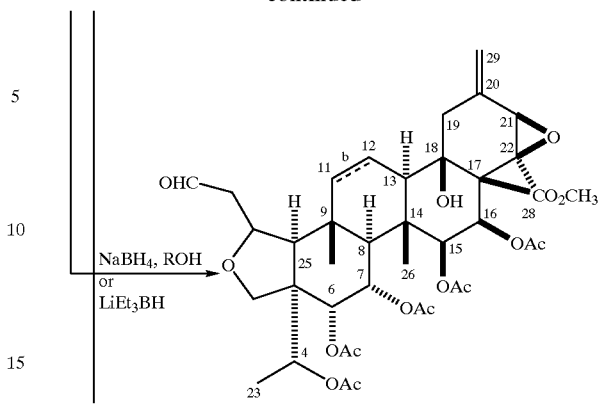

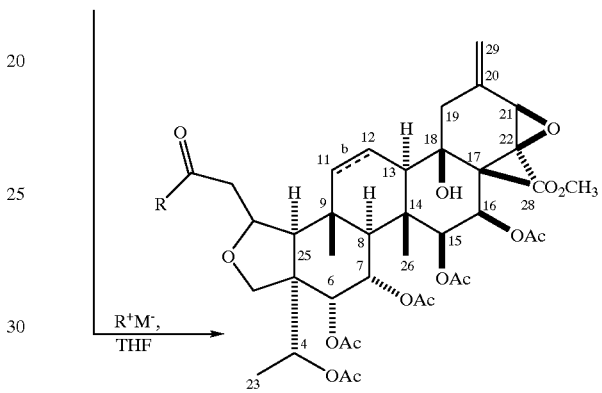

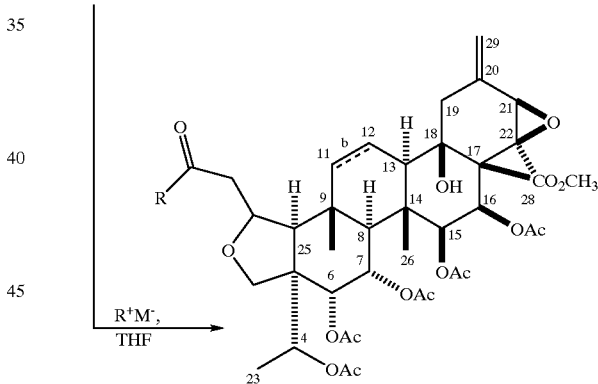

The lactone group of compound 1a can be rearranged to substituted THF esters under acidic or basic conditions (Reaction Scheme D). Stirring the lactone derivative in an alcoholic solvent such as methanol or ethanol with an acid such as $H_2SO_4$ or a base such as potassium carbonate ($K_2CO_3$) gives the rearranged THF ester with the ester group corresponding to the alcohol selected as solvent. This reaction also causes the hydrolysis of the C4 acetate group which is reesterified by stirring the hydroxy analog with acetic anhydride ($Ac_2O$).

$R^{10a}$-acetadehyde THF derivatives can be prepared by reacting the lactone starting material with reducing agents such as $NaBH_4$ or $LiEt_3BH$ (Super hydride) in an alcoholic solvent.

$R^{10a}$-ketone THF derivatives are prepared by reacting the lactone starting material with alkylmetal reagents such as methyl lithium in an aprotic solvent such as THF preferably at low temperatures such as −78° C.

The $R^{10a}$ ester, aldehyde and ketone groups of these THF analogs can be derivatized with a variety of procedures commonly known to practitioners.

The C20 olefin can then be converted to the corresponding hydroxy derivative with ozone and reductive workup as described above.

REACTION SCHEME E

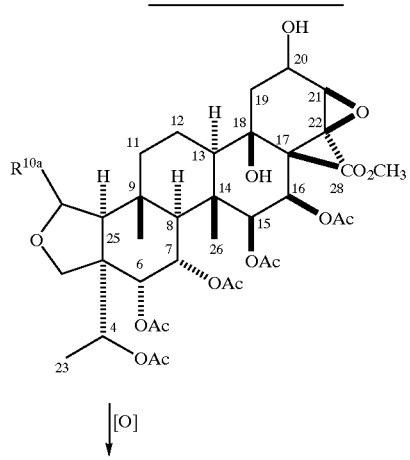

↓ [O]

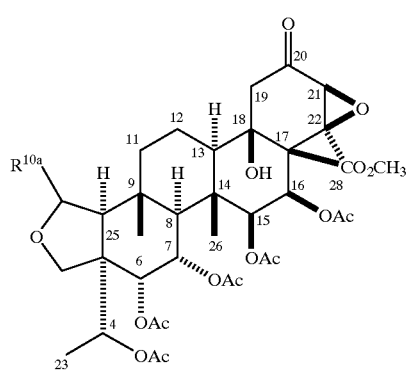

In Reaction Scheme E, the C20 hydroxy group of the derivatized THF derivatives described in the preceeding Reaction Schemes can be oxidized to the corresponding ketone under a variety of conditions. The Jones reagent (chromic acid and sulfuric acid in $H_2O$), pyridinium chlorochromate, or oxalyl chloride plus DMSO will achieve this conversion.

REACTION SCHEME F

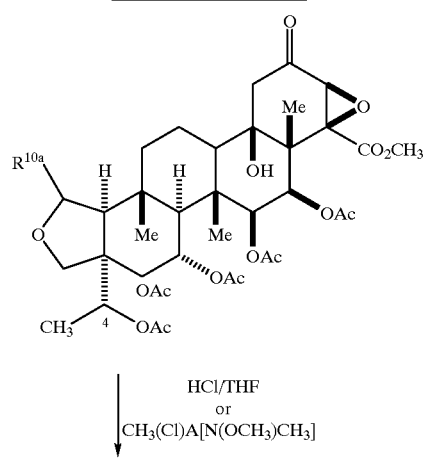

↓ HCl/THF or $CH_3(Cl)Al[N(OCH_3)CH_3]$

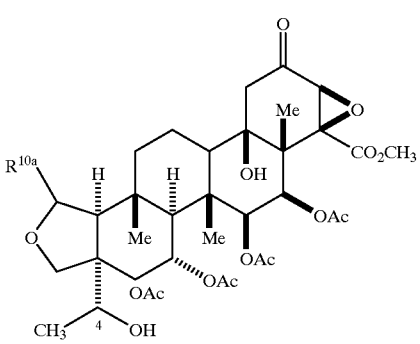

Tetrahydrofuran derivatives can be selectively de-acetylated at C4 to give the corresponding alcohol by reaction with an aqueous solution of HCl (preferably 2M to 3M concentration) in THF at 45° C. Deacetylation can also be achieved by reacting with $CH_3(Cl)Al[N(OCH_3)CH_3$ (Weinreb reagent) in inert solvents such as THF, toluene or methylene chloride.

REACTION SCHEME G

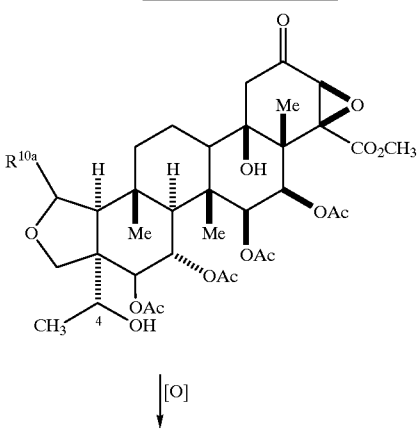

↓ [O]

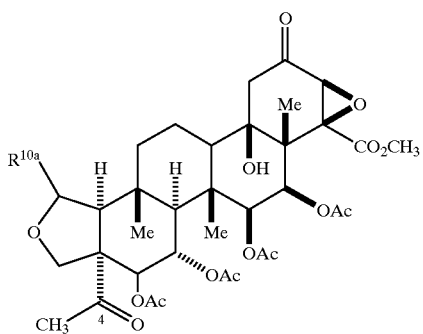

The C4 hydroxy group can be oxidized to the corresponding ketone by a variety of oxidizing agents. The Jones reagent (chromic acid and sulfuric acid in $H_2O$), pyridinium chlorochromate, and oxalyl chloride plus DMSO all will achieve this conversion.

REACTION SCHEME II

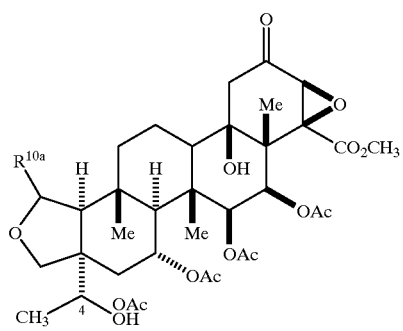

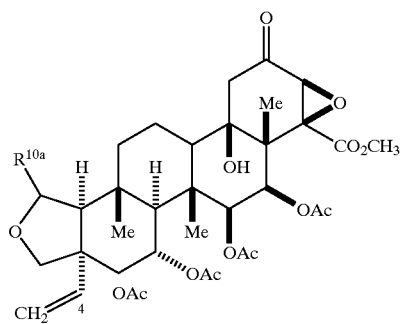

The C4 hydroxy group can be dehydrated to give the olefin. Reaction of the alcohol with tris-phenoxymethylphosphonium iodide in hexamethylphosphorous triamide (HMPT) at 75° C. will achieve this conversion.

REACTION SCHEME I

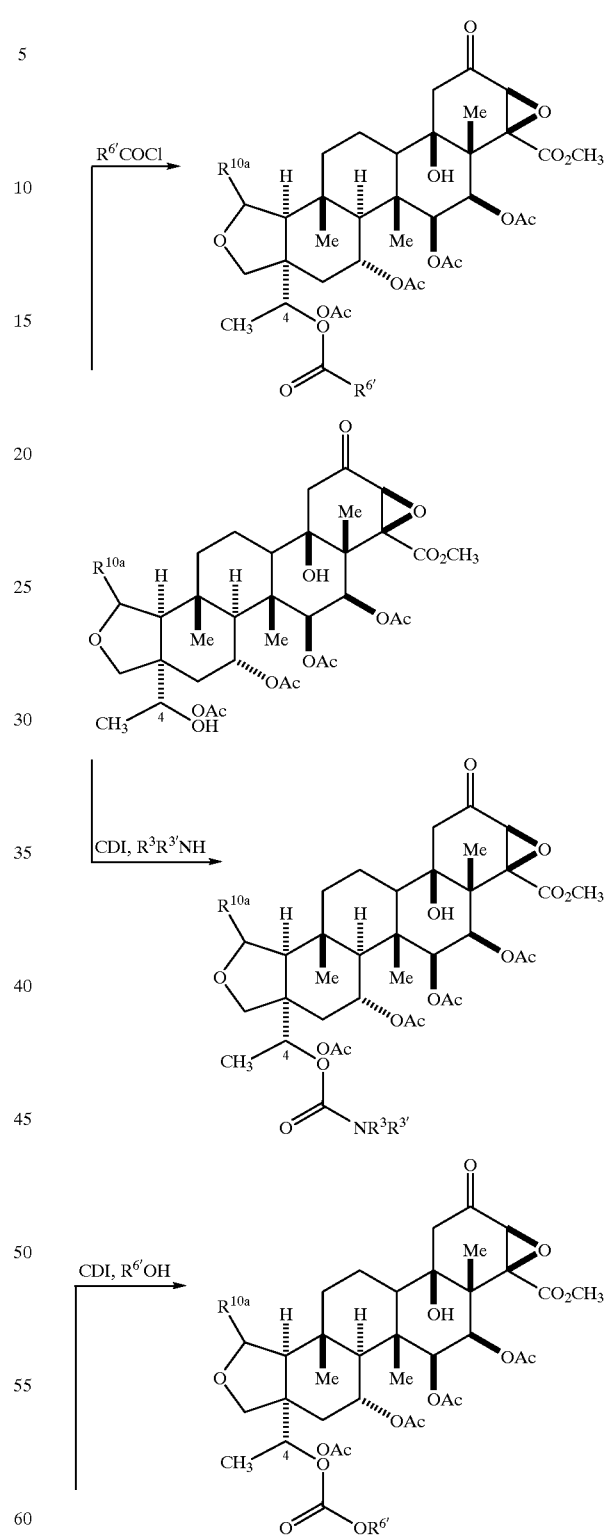

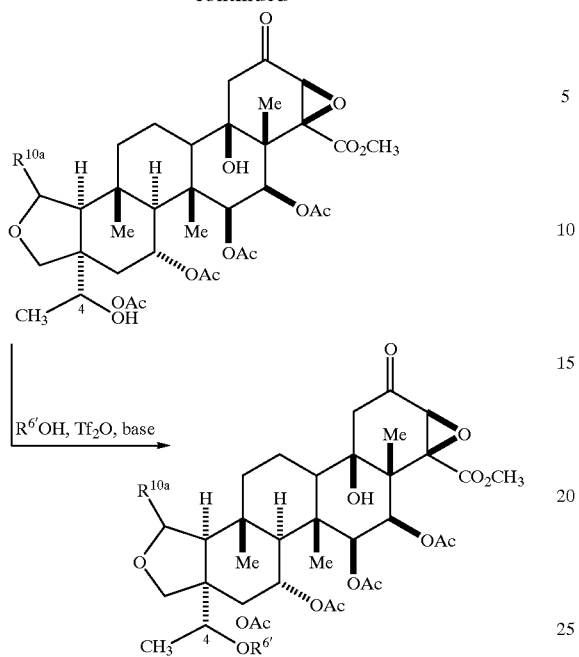

As depicted in Reaction Scheme I, esters at C4 can be prepared by reaction of a preformed carboxylic acid chloride with the C4 alcohol derivative in a basic solvent such as pyridine. It should be understood that $R^{6'}$ is used to represent a portion of the $R^6$ definition, e.g. $R^6$ can be an alkyl carbonate which is depicted in the scheme as $OC(=O)OR^{6'}$, $R^{6'}$ representing the alkyl substituent. The acid chlorides, when not purchased, are prepared by stirring the carboxylic acids in reagents such as oxalyl chloride or thionyl chloride. Esters may also be prepared by reaction of the acid chloride and C4 alcohol with silver cyanide (AgCN) in an aprotic solvent such as HMPA. C4 sulfonate derivatives are prepared in a similar manner by reaction with sulfonyl chlorides.

C4 carbonate and carbamate derivatives are prepared by first reacting the C4 alcohol derivative with carbonyldiimidazole (CDI) to obtain the imidazolecarbonyl intermediate which is then reacted with an alcohol or amine ($R^3R^{3'}NH$) to give the corresponding carbonate or carbamate derivatives.

C4 ether derivatives can also be prepared. The best procedure involves reacting an alcohol with trifluoromethanesulfonic anhydride ($Tf_2O$, triflic anhydride) to obtain the preformed triflate in dichloromethane at reduced temperature, preferably −78° C. To this solution is added the C4 alcohol, the reaction mixture is warmed to room temperature and stirring is continued until reaction is complete. Ethers may also be prepared by heating a mixture of C4 alcohol, the appropriate alkylhalide and an excess of silver oxide ($Ag_2O$) in an aprotic invert solvent such as THF.

The transformations described above can be first performed on compound Ia [(4,6,7,15,16-pentakis(acetyloxy)-21,22-epoxy-18-hydroxy-22-methyoxycarbonyl[6α,7α,15β,16β,21β,22β]D:A-Freido-A-homo-27,30-dinor-24-oxaoleana-1,20(29)-dien-3-one]. Then the resultant derivatives can be converted to C20 keto THF derivatives as described above.

REACTION SCHEME J

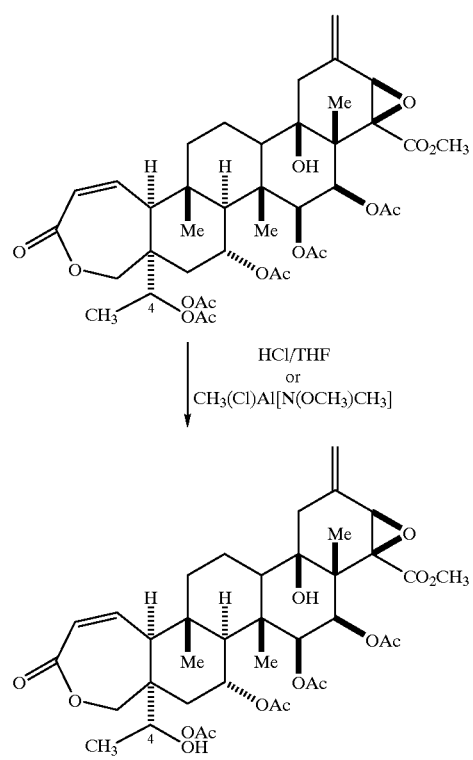

Lactone 1a can be selectively de-acetylated at C4 to give the corresponding alcohol by reacting it with an aqueous solution of HCl (preferably 2M to 3M concentration) in THF. It can also be prepared by reaction with $CH_3(Cl)Al[N(OCH_3)CH_3]$ (Weinreb reagent) in inert solvents such as THF, toluene or methylene chloride. The hydroxy product can be further derivatized according to procedures described in Reaction Schemes G and H. The lactone derivatives can then be converted to C20 keto THF derivatives according to Reaction Schemes A–E.

The following 2 reaction schemes are incompatible with a C18 ketone group. They can be first performed on lactone 1a, which in turn can be converted to $C_{20}$ keto THF derivatives.

REACTION SCHEME K

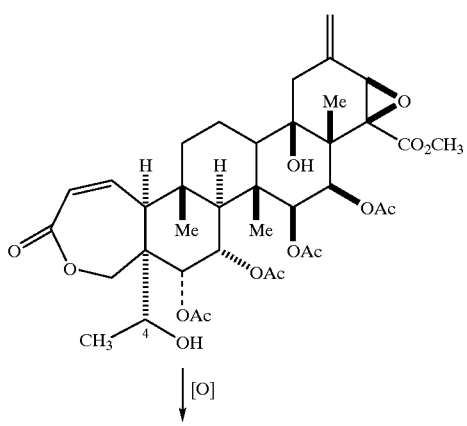

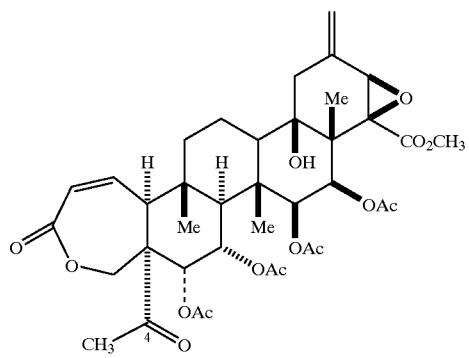

The C4 hydroxy group can be oxidized to the corresponding ketone by a variety of oxidizing agents. The Jones reagent (chromic acid and sulfuric acid in $H_2O$), pyridinium chlorochromate, and oxalyl chloride plus DMSO all will achieve this conversion.

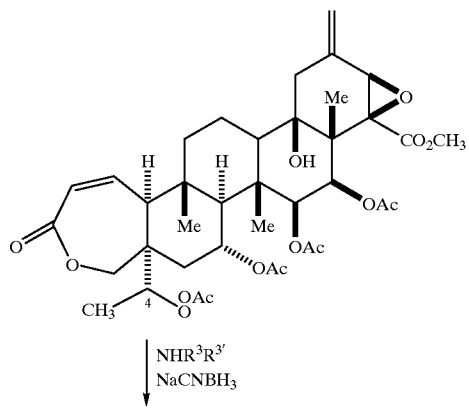

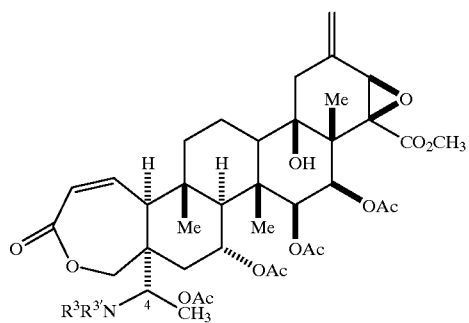

C4 amino derivatives can be prepared by reacting the C4 ketone with an amine $NHR^3R^{3'}$ in a variety of solvents with a reducing agent such as sodium cyanoborohydride. The lactone derivatives can then be converted to C20 keto THF derivatives according to Reaction Schemes A–E.

REACTION SCHEME L

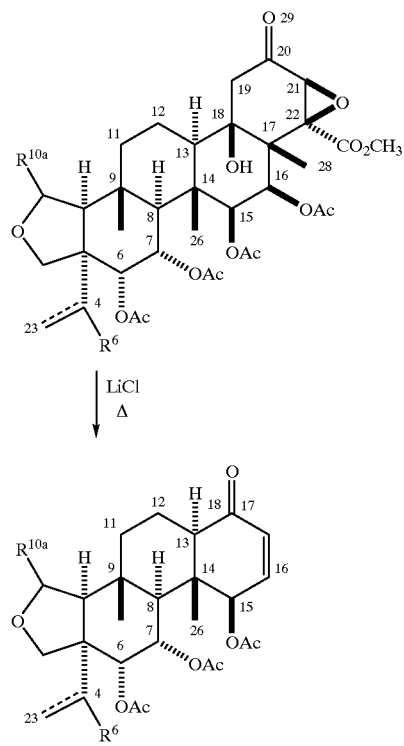

Reaction of the pentacyclic ketone with a metalhalide such as LiCl in a solvent such as DMF or DMSO at elevated temperatures such as 100° C. results in ring cleavage to obtain the tetracyclic enone depicted.

REACTION SCHEME M

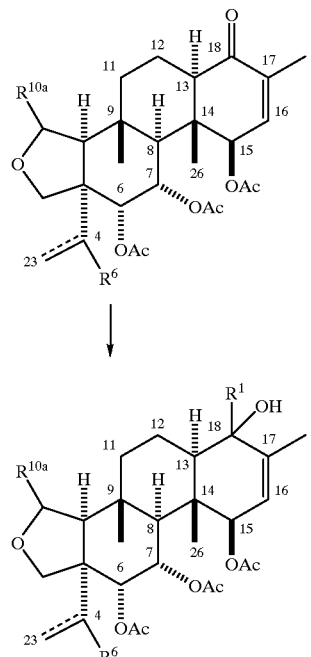

The C18 ketone can be reacted with nucleophiles ($R^1$-$M+$) to give C18 substituted hydroxy derivatives. In general, Grignard reagents ($R^1MgBr$) or alkyllithium reagents ($R^1Li$) are utilized in aprotic solvents such as diethyl ether or THF. Allylsilane reagents also add to the C18 ketone. For instance, reaction with allyltrimethylsilane and titanium tetrachloride in THF or diethyl ether gives the allyl adduct.

When R6 is OAc, it can be selectively hydrolyzed and derivatized using reaction schemes described above for the pentacyclic series.

REACTION SCHEME N

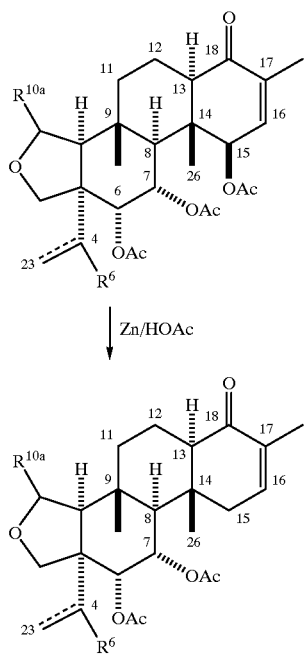

The acetoxy group at position 15 can be selectively removed from the ketone precursor shown in excellent yield by refluxing in acetic acid with Zn powder. The C18 ketone can then be derivatized according to methods described in Reaction scheme M.

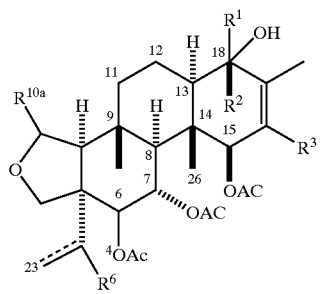

REACTION SCHEME O

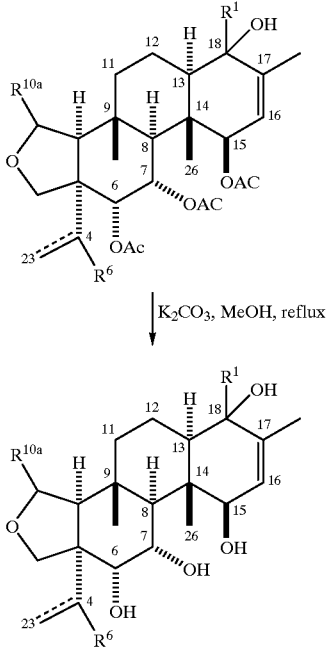

It was already shown in Reaction Scheme F that the acetate group at position 4 can be selectively removed. The acetate groups at positions 6, 7 and 15 can be removed by reaction with $K_2CO_3$ in refluxing methanol.

REACTION SCHEME P

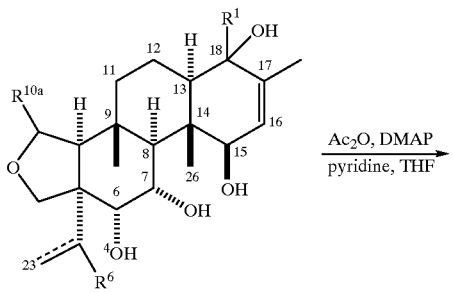

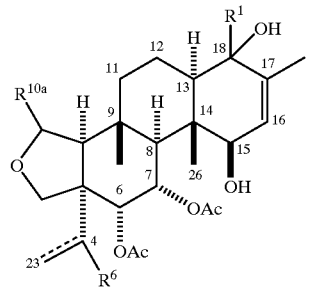

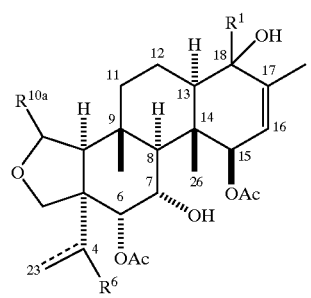
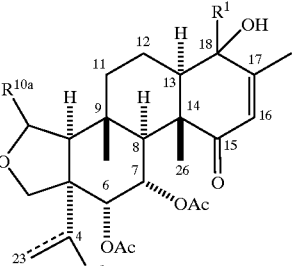

Treatment of the hydroxy derivative from Reaction Scheme O gives the C15 and C7 hydroxy derivatives shown in this scheme. Similar reactions can be performed on this starting material. For instance, reaction with acetone with catalysis with PTSA (para-toluene sulfonic acid) gives a mixture of acetonides, primarily at C6/C7 and C7/C15. Ester, carbamate and ether derivatives can be prepared using procedures described in Reaction Scheme I.

REACTION SCHEME Q

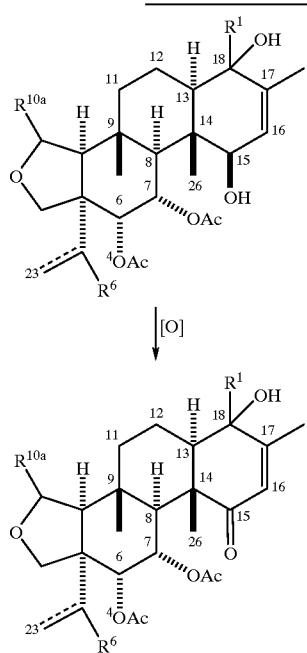

REACTION SCHEME Q

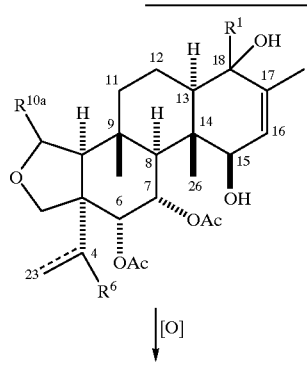

The C15 hydroxy group can be oxidized to the corresponding ketone by a variety of oxidizing agents. The Jones reagent (chromic acid and sulfuric acid in $H_2O$), pyridinium chlorochromate, and oxalyl chloride plus DMSO all will achieve this conversion.

Utility

The present invention is related to compounds of formula I, including but not limited to those specified in the examples, which are useful in a mammalian subject for the treatment and prevention of immunemediated diseases such as the resistance by transplantation of organs or tissue such as heart, kidney, liver, medulla ossium, skin, cornea, lung, pancreas, intestinum tenue, limb, muscle, nervus, duodenum, small-bowel, pancreatic-islet-cell, including xeno transplants, etc.; graft-versus-host diseases brought about by medulla ossium transplantation; autoimmune diseases such as rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, and the like; and further infectious diseases caused by pathogenic microorganisms. Further uses may include the treatment and prophylaxis of inflammatory and hyperproliferative skin diseases and cutaneous manifestations of immunologically mediated illnesses, such as psoriasis, atopical dermatitis, contact dermatitis and further eczematous dermatitises and further eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne and Alopecia areata; various eye diseases (autoimmune and otherwise) such as keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; pollen allergies, reversible obstructive airway disease, which includes condition such as asthma (for example, bronchial asthma, allergic asthma, intrinsic asthma, extrinsic asthma and dust asthma), particularly chronic or inveterate asthma (for example, late asthma and airway hyper-responsiveness), bronchitis and the like; inflammation of mucous and blood vessels such as gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases; intestinal inflammations/allergies such as Coeliac diseases, proctitis, eosinophilic gastroenteritis, mastocytosis, Crohn's disease and ulcerative colitis; food-related allergic diseases which have symptomatic manifestation remote from the gastrointestinal tract (e.g. migraine, rhinitis and eczema); renal diseases such as interstitial nephritis, Good-pasture's syndrome, hemolytic-uremic syndrome and diabetic nephropathy; nervous diseases such as multiple myositis, Guillain-Barre syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fascitis; periodontal disease such as lesions of gingiva, periodontium, alveolar bone and substantia ossea dentis; nephrotic syndrome such as glomerulonephritis; male pattern alopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation or ischemic disease (for example, thrombosis and cardiac infraction): intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring and corneal alkali burn; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenis, metastasis of carcinoma and hypobaropathy; disease caused by histamine or leukotriene-$C_4$ release; Behcet's disease such as intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease such as immunogenic diseases (for example, chronic autoimmune liver diseases such as the group consisting of autoimmune hepatitis, primary biliary cirrhosis and sclerosing cholangitis), partial liver resection, acute liver necrosis (e.g. necrosis caused by toxin, viral hepatitis, shock, or anoxia), B-virus hepatitis, non-A/non-B hepatitis, cirrhosis (such as alcoholic cirrhosis) and hepatic failure such as fulminant hepatic failure, late-onset hepatic failure and "acute-on-chronic" liver failure (acute liver failure on chronic liver diseases), and moreover are useful for various diseases because of their useful activity such as augmention of chemotherapeutic effect, preventing or treating activity of cytomegalovirus infection, particularly HCMV infection, and antiinflammatory activity; and The compounds of the present invention may also be used in the treatment of immunodepression or a disorder involving immunodepression, such as AIDS, cancer, senile dementia, trauma (including wound healing, surgery and shock) chronic bacterial infection, and certain central nervous system disorders.

A method of treating a condition in a mammal, the treatment of which is effected or facilitated by $K_v1.3$ inhibition, comprising the administration, in an amount that is effective at inhibiting $K_v1.3$, of a compound of Formula I. The method of treating a condition in a mammal, the treatment of which is effected or facilitated by $K_v1.3$ inhibition, wherein the condition is selected from the group consisting of: immunemediated diseases such as the resistance by transplantation of organs or tissue such as heart, kidney, liver, medulla ossium, skin, cornea, lung, pancreas, intestinum tenue, limb, muscle, nervus, duodenum, small-bowel, pancreatic-islet-cell, including xeno transplants, etc.; graft-versus-host diseases brought about by medulla ossium transplantation; autoimmune diseases such as rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, and the like; and further infectious diseases caused by pathogenic microorganisms. Further uses may include the treatment and prophylaxis of inflammatory and hyperproliferative skin diseases and cutaneous manifestations of immunologically mediated illnesses, such as psoriasis, atopical dermatitis, contact dermatitis and further eczematous dermatitises and further eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne and Alopecia areata; various eye diseases (autoimmune and otherwise) such as keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; pollen allergies, reversible obstructive airway disease, which includes condition such as asthma (for example, bronchial asthma, allergic asthma, intrinsic asthma, extrinsic asthma and dust asthma), particularly chronic or inveterate asthma (for example, late asthma and airway hyper-responsiveness), bronchitis and the like; inflammation of mucous and blood vessels such as gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases; intestinal inflammations/allergies such as Coeliac diseases, proctitis, eosinophilic gastroenteritis, mastocytosis, Crohn's disease and ulcerative colitis; food-related allergic diseases which have symptomatic manifestation remote from the gastrointestinal tract (e.g. migraine, rhinitis and eczema); renal diseases such as interstitial nephritis, Good-pasture's syndrome, hemolytic-uremic syndrome and diabetic nephropathy; nervous diseases such as multiple myositis, Guillain-Barre syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Siogren's syndrome; adiposis; eosinophilic fascitis; periodontal disease such as lesions of gingiva, periodontium, alveolar bone and substantia ossea dentis; nephrotic syndrome such as glomerulonephritis; male pattern aleopreia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation or ischemic disease (for example, thrombosis and cardiac infraction): intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring and corneal alkali burn; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenis, metastasis of carcinoma and hypobaropathy; disease caused by histamine or leukotriene-$C_4$ release; Behcet's disease such as intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease such as immunogenic diseases (for example, chronic autoimmune liver diseases such as the group consisting of autoimmune hepatitis, primary biliary cirrhosis and sclerosing cholangitis), partial liver resection, acute liver necrosis (e.g. necrosis caused by toxin, viral hepatitis, shock, or anoxia), B-virus hepatitis, non-A/non-B hepatitis, cirrhosis (such as alcoholic cirrhosis) and hepatic failure such as fulminant hepatic failure, late-onset hepatic failure and "acute-on-chronic" liver failure (acute liver failure on chronic liver diseases), and moreover are useful for various diseases because of their useful activity such as augmention of chemotherapeutic effect, preventing or treating activity of cytomegalovirus infection, particularly HCMV infection, and antiinflammatory activity; and immunodepression or a disorder involving immunodepression, such as AIDS, cancer, senile dementia, trauma (including wound healing, surgery and shock), chronic bacterial infection, and certain central nervous system disorders.

An embodiment of the invention is a method for the treatment of autoimmune diseases. Another embodiment of the invention is a method for the prevention of rejection of foreign organ transplants comprising administering to a patient in need of such treatment a therapeutically effective amount of a compound of formula I.

One end result of an autoimmune or a rejection process is tissue destruction caused by inflammatory cells and the mediators they release. Anti-inflammatory agents such as NSAID's and corticosteroids act principally by blocking the effect or secretion of these mediators, but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immuno-suppressive agents are as likely to succumb from infection as they are from their autoimmune disease.

Cyclosporin A, which was approved by the U.S. FDA in 1983, is currently the leading drug used to prevent rejection of transplanted organs. The drug acts by inhibiting the body's immune system from mobilizing its vast arsenal of natural protecting agents to reject the transplant's foreign protein. Though cyclosporin A is effective in fighting transplant rejection, it is nephrotoxic and is known to cause several undesirable side effects including kidney failure, abnormal liver function and gastrointestinal discomfort.

Newer, safer drugs exhibiting fewer side effects are constantly being searched for in the field. The present invention provides for immunosuppressant agents which are inhibitors of a voltage dependent potassium channel, $K_v1.3$, that is found on human T-lymphocytes.

Potassium channels modulate a number of cellular events such as muscle contraction, neuro-endocrine secretion, frequency and duration of action potentials, electrolyte homeostasis, and resting membrane potential. These channels comprise a family of proteins that have been classified according to their biophysical and pharmacological characteristics. Inhibition of $K^+$ channels, in their role as modulators of the plasma membrane potential in human T-lymphocytes, has been postulated to play a role in eliciting immunosuppressive responses. In regulating membrane potential, $K^+$ channels play a role in the regulation of intracellular $Ca^{++}$ homeostasis, which has been found to be important in T-cell activation. The biochemical characterization of $K^+$ channels is underdeveloped, due to the paucity of selective high affinity probes.

Functional voltage-gated $K^+$ channels can exist as multimeric structures formed by the association of either identical or dissimilar subunits. This phenomena is thought to account for the wide diversity of $K^+$ channels. However, subunit compositions of native $K^+$ channels and the physiologic role that particular channels play are, in most cases, still unclear.

The $K_v1.3$ channel is a voltage-gated potassium channel that is found in neurons, blood cells, osteoclasts and T-lymphocytes. The Chandy and Cahalan laboratories proposed a hypothesis that blocking the $K_v1.3$ channel would elicit an immunosuppressant response. (Chandy et al., *J. Exp. Med.* 160, 369, 1984; Decoursey et al., Nature, 307, 465, 1984). However, the $K^+$ channel blockers employed in their studies were non-selective. Until research with the peptide margatoxin, a peptide found in scorpion venom, no specific inhibitor of the $K_v1.3$ channel existed to test this hypothesis. Although a laboratory (Price et al., *Proc. Natl. Acad. Sci. USA,* 86, 10171, 1989) showed that charybdotoxin would block $K_v1.3$ in human T cells, charybdotoxin was subsequently shown to inhibit four different $K^+$ channels ($K_v1.3$ and three distinct small conductance $Ca^{++}$ activated $K^+$ channels) in human T-lymphocytes, limiting the use of this toxin as a probe for the physiological role of $K_v1.3$ (Leonard et al., *Proc. Natl. Acad. Sci. USA,* 89, 10094, 1992). Margatoxin, on the other hand, blocks only $K_v1.3$ in T-cells, and has immunosuppressant activity in both in vitro and in vivo models. (Lin et al., *J. Exp. Med,* 177, 637, 1993). Since the compounds of the embodiments of this invention produce blockade of $K_v1.3$, they will also inhibit T-cell activation.

Also within the scope of this invention is a method of treating a condition in a mammal, the treatment of which is effected or facilitated by $K_v1.3$ inhibition, comprising the administration of a pharmaceutical composition comprising a suitable pharmaceutical carrier and a compound of Formula (I), in an amount that is effective at inhibiting $K_v1.3$.

Also within the scope of this invention is a combination therapy comprising a compound of formula I and one or more immunosuppressant agents. These immunosuppressant agents within the scope of this invention include, but are not limited to, IMUREK® azathioprine sodium, brequinar sodium, SPANIDIN® gusperimus trihydrochloride (also known as deoxyspergualin), mizoribine (also known as bredinin), CELLCEPT® mycophenolate mofetil, NEORAL® Cyclosporin A (also marketed as a different formulation of Cyclosporin A under the trademark SANDIMMUNE®), PROGRAF® tacrolimus (also known as FK-506) and RAPIMMUNE® sirolimus (also known as rapamycin), leflunomide (also known as HWA-486), glucocortcoids, such as prednisolone and its derivatives, antibody therapies such as orthoclone (OKT3) and Zenapax and antithymyocyte globulins, such as thymoglobulins.

Using the methodologies described below, representative compounds of the invention were evaluated and found to exhibit $IC_{50}$ values of at least <10 µM in any of the assays thereby demonstrating and confirming the utility of the compounds of the invention as $K_v1.3$ inhibitors and immunosuppressants.

T Cell IL-2 Assay

Peripheral blood mononuclear (MNC) cells from healthy donors were separated by density centrifugation with ficoll-hypaque (LSM, Organon Teknika, Durham, N.C.), followed by rosetted with neuraminidase treated sheep red blood cells (SRBC). After another centrifugation with leucocyte separation medium (LSM), the SRBC of the rosetted T cells were then lysed with ammonium chloride lysing buffer (GIBCO, Grand Island, N.Y.). Such purified T cells were resuspended at $3\times10^6$/ml in RPMI 1640 culture medium (GIBCO) supplemented with 10% fetal calf serum (Sigma, St. Louis, Mo.), 100 mM glutamine, 1 mM sodium pyruvate, 0.1 mM non-essential amino acids, and 1% penn-strep (GIBCO). The cell suspension was immediately distributed into 96 well round-bottom microculture plates (Costar) at 200 µl/well. The various dilutions of test compound were then added in triplicate wells at 25 µl/well, incubated for 30 min at 37° C. Ionomycin (125 ng/ml), and PMA (1 or 5 ng/ml), were added to the appropriate wells. The culture plates were then incubated at 37° C. in a humidified atmosphere of 5% $CO_2$—95% air for 18–24 hours. The supernatants were removed, and assayed for IL-2 with an IL-2 capture ELISA, using monoclonal anti-IL-2, and biotinylated goat anti-IL-2 antibodies (unconjugated antibodies purchased from R&D System, Minneapolis, Minn.). The ELISA was developed with streptavidin conjugated peroxidase (Zymed, San Francisco, Calif.) and substrate for peroxidase (Sigma). Mean OD and units of IL-2 of the replicate wells were calculated from standard curve, created with recombinant IL-2 (Collaborative Biomedical Products, Bedford, Mass.) and the results were expressed as concentration of compound required to inhibit IL-2 production of T cells by 50%.

T Cell Proliferation Assay

Peripheral blood mononuclear cells (MNC) from healthy donors were separated by density centrifugation with ficoll-hypaque (LSM, Organon Teknika, Durham, N.C.). After washing the MNC with complete media (RPMI 1640 medium with 5% fetal calf serum, 100 mM glutamine, 1 mM sodium pyruvate, 0.1 mM non-essential amino acid, and 1% penn-strep, obtained from GIBCO, Grand Island, N.Y.), they were then irradiated at 7500 RADS, and resuspended at $4-4.5\times10^6$ cells/ml in complete media. Another aliquot of MNC were rosetted with neuraminidase treated SRBC. After another centrifugation with LSM, the sheep red blood cells (SRBC) of these rosetted T cells were then lysed with ammonium chloride lysing buffer (GIBCO, Grand Island, N.Y.). After washing 2x with complete media, these purified T cells were also resuspended at $2-2.5\times10^6$ cells/ml in complete media. The various dilutions of the compound were added in triplicates at 50 µl/well of a 96 well flat-bottom microculture plate (Costar, Cambridge, Mass.). T cell suspension was then immediately distributed into the wells at 100 µl/well. After incubating the cells with compound for 30 min. at 37° C. in a humidified atmosphere of 5% $CO_2$—95% air, 20 µl/well of anti-CD3 (Ortho Diagnostic, N.J.) at final conc. of 0.3 ng/ml was added, followed by 50 µl of the irradiated MNC. The culture plates were then incubated at 37° C. in a humidified atmosphere of 5% $CO_2$–95% air for 72 hours. The proliferation of T lymphocytes was assessed by measurement of tritiated thymidine incorporation. During the last 18–24 hrs. of culturing, the cells were pulse-labeled with 2 µCi/well of tritiated thymidine (NEN, Cambridge, Mass.). The cultures were harvested on glass fiber filters using a multiple sample harvester (MACH-II, Wallac, Gaithersburg, Md.). Radioactivity of filter discs corresponding to individual wells was measured by standard liquid scintillation counting methods (Betaplate Scint Counter, Wallac). Mean counts per minute of replicate wells were calculated and the results were expressed as concentration of compound required to inhibit tritiated thymidine uptake of T cells by 50%.

KV1.3-Rubidium Efflux Assay

CHO cells transfected with $K_v1.3$ channels at site densities of approximately 40,000 sites/cell are plated into 96 well culture plates and maintained in Iscove's Modified Dulbecco's Medium (IMDM, with L-Glutamine and HEPES, JRH Biosciences). Cells are incubated overnight with $^{86}Rb^+$ (3 µCi/ml, Dupont-NEN) in the glutamine supplemented IMDM. After aspiration of the media, 100 µl of Low K Buffer (in mM, 6.5 KCl, 125 NaCl, 1 $CaCl_2$, 2 $MgCl_2$, 10 HEPES, pH adjusted to 7.2 with NaOH) is added to each well followed by 100 µl test samples in Low K Buffer also containing 0.2% BSA and 2 mM ouabain. Samples are tested at either 1 µg/ml for routine screening or at a variety of concentrations encompassing at least 1/10 to 10 times the putative $IC_{50}$ of test compound to determine potency. After a fixed preincubation time, which is usually 10 min, the samples are aspirated. The $K_v1.3$ channels are opened by depolarization of the cells with High K Buffer (final concentrations, in mM, 63.25 KCl, 68.25 NaCl, 1 $CaCl_2$, 2 $MgCl_2$, 10 HEPES, pH adjusted to 7.2 with NaOH) also containing test compounds. To measure $^{86}Rb^+$ efflux through the channels, aliquots of 100 µl are taken from each well after a given time and added to plates containing 100 µl MicroScint-40 (Packard) for counting by liquid scintillation techniques. MicroScint-40 (100 µl) is then added to each well of the cell plate to determine the remaining $^{86}Rb^+$ activity. The efflux counts are normalized for the total amount of $^{86}Rb^+$ that was in the cells by adding the efflux counts to the cell plate counts. Activity is determined by % inhibition of the efflux window that is established using a saturating concentration of margatoxin (MgTX), a 39 amino acid peptide that is a potent blocker of $K_v1.3$ channels ($IC_{50}=100$ pM).

Dosage Forms

As an immunosuppressive, these compounds are useful in the treatment of autoimmune diseases, the prevention of rejection of foreign organ transplants and/or related afflictions, diseases and illnesses.

The compounds of this invention can be administered for the treatment of autoimmune diseases, the prevention of rejection of foreign organ transplants and/or related afflictions, diseases and illnesses according to the invention by any means that effects contact of the active ingredient compound with the site of action in the body of a warm-blooded animal. For example, administration, can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1–500 milligrams per day. Ordinarily, from 10 to 100 milligrams per day in one or more applications is effective to obtain desired results. These dosages are the effective amounts for the treatment of autoimmune diseases, the prevention of rejection of foreign organ transplants and/or related afflictions, diseases and illnesses.

The active ingredient can be administered orally in solid dosage forms, such as capsules, tablets, troches, dragees, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol. The solution is made to volume with water for injection and sterilized.

Suspension

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

The following examples illustrate the preparation of the compounds of Formula I and as such are not to be considered as limiting the invention set forth in the claims appended hereto.

EXAMPLE 1

A Method of Extracting the Compounds of Formula 1(a) and 1(b) from *Spachea correa*

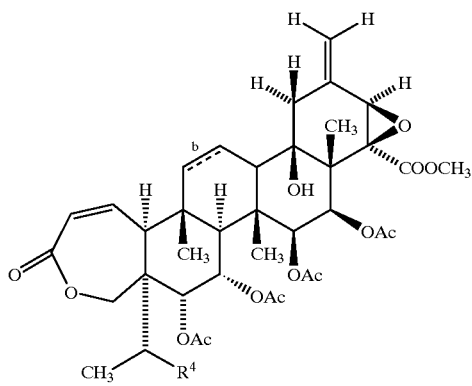

Formula 1(a) b is a single bond and R is OAc
Formula 1(b) b is a double bond and R is OAc One gram of an ethanol extract of the roots of *Spachea correa* was partitioned between 100 ml of hexane (twice) and 100 ml of 90% aqueous methanol. After separation of the phases, the defatted methanol was concentrated down under vacuum to give an aqueous suspension. This was diluted out to 100 ml with water and extracted, with 100 ml of methylene chloride.

The bioactive methylene chloride extract was dried down to give 12 mg of residue. This was first fractionated by preparative thin layer chromatography (TLC) on a 20 cm by 20 cm E. Merck silica gel 60F$_{254}$ plate of 1 mm thickness using methylene chloride-ethyl acetate 1:1 (v/v) as solvent, then by high performance liquid chromatography (HPLC) using a Zorbax RxC$_8$ 4.6 mm×25 cm column, operated at 50° C. and eluted with a 50 minute gradient of acetonitrile-:water (1:1, v/v) to 100% acetonitrile, delivered at 1 ml/min, to afford compound 1(a) and 1(b).

Homogeneity of the preparations was ascertained in several TLC systems, such as E. Merck silica gel 60F$_{254}$, methylene chloride-ethyl acetate 1:1, Rf 1(a) 0.4, Rf 1(b) 0.3; Whatman KC$_{18}$, methanol-water 9:1, Rf 1(a) 0.65, Rf 1(b) 0.75 and by HPLC using a Zorbax RxC$_8$ column, acetonitrile-water 3:2, k' 1(a) 4.15, k' 1(b) 3.30; and by NMR.

Mass spectra were recorded on JEOL SX-102A (electron impact, EI,903V) and JEOL HX110 (Fast Atom Bombardment, FAB) mass spectrometers. Exact mass measurements were performed at high resolution (HR-EI) using perfluorokerosene (PFK) as the internal standard. Trimethylsilyl derivatives were prepared with a 1:1 mixture of BSTFA-pyridine at room temperature The FAB spectrum was run in a matrix of dithiothreitol (20/80).

The compound of Formula 1(a) runs underivatized by EI. The molecular ion is observed a m/z 788 and three successive loses of acetic acid are observed. The base peak is observed a m/z 334. The compound does not silylate. Scanning HR-EI indicated a molecular formula of $C_{40}H_{52}O_{16}$. A table of the critical HR-EI data is given below.

| Observed m/z | Formula | Assignment |
|---|---|---|
| 788.3220 | $C_{40}H_{52}O_{16}$ | M+ |
| 728.3040 | $C_{38}H_{48}O14$ | M-acetic acid |
| 668.2834 | $C_{36}H_{44}O_{12}$ | M-2 × acetic acid |
| 334.1417 | $C_{18}H_{22}O_6$ | base peak |

$^{13}$C NMR spectra were recorded for the compound of Formula 1(a) in CD$_2$Cl$_2$ at 100 MHz on a Varian Unity 400 NMR spectrometer at 20° C. Chemical shifts are given in ppm relative to tetramethylsilane (TMS) at zero ppm using the solvent peak at 53.8 ppm as internal standard. The following data were observed: 15.0, 15.2, 16.8, 17.1, 20.7*, 20.9, 21.1, 21.6, 21.8, 22.2, 35.6, 40.8*, 42.1, 43.6, 45.1, 47.5, 49.3*, 53.5, 59.1, 62.6, 63.5, 66.1, 66.7*, 68.4*, 69.9, 73.9, 75.0, 75.6, 77.1*, 119.4, 123.7, 138.9, 143.0, 167.7, 169.2, 169.3*, 170.25, 170.31, 170.8, 171.3 ppm (where the * signifies the observation as broad resonances). The carbon count of 40 is in agreement with the molecular formula $C_{40}H_{52}O_{16}$ derived by scanning HR EI-MS.

The $^1$H NMR spectra of compound of Formula(a) was recorded at 400 MHz in CD$_2$Cl$_2$ on a Varian Unity 400 NMR spectrometer at 25° C. Chemical shifts are in ppm relative to TMS at zero ppm using the solvent peak as δ5.32 as the internal standard.

The mass spectra of the compound of Formula 1(b) was obtained as above. The following results were obtained:

| Observed m/z | Formula | Assignment |
|---|---|---|
| 786.3075 | $C_{40}H_{50}O_{16}$ | M+ |
| 726.2886 | $C_{38}H_{46}O14$ | M-acetic acid |
| 666.2651 | $C_{36}H_{42}O_{12}$ | M-2 × acetic acid |
| 606.2451 | $C_{34}H_{38}O_{10}$ | M-3 × acetic acid |
| 489.2099 | $C_{26}H_{33}O_9$ | base peak |
| 471.1992 | $C_{26}H_{31}O_8$ | |

$^{13}$C NMR spectra were recorded for the compound of Formula1(b) using the procedure described above. The following results were observed: 14.8, 14.9, 17.3, 20.8, 20.9, 21.3, 21.7, 21.8, 21.9, 27.1, 35.1, 40.6, 42.3, 45.4, 48.1, 50.4, 53.5, 54.1, 57.8, 63.7, 66.2, 67.8, 68.6, 71.4, 73.3, 73.8, 74.4, 119.5, 121.1, 124.3, 137.1, 138.9, 143.3, 167.6, 168.6, 169.3, 169.5, 169.9, 171.0, 171.7 ppm.

The carbon count of 40 is in agreement with the molecular formula $C_{40}H_{50}O_{16}$ derived by scanning HR EI-MS.

EXAMPLE 2

A Method of Extracting the Compounds of Formula 1(c) And 1(d) from *Spachea correa*

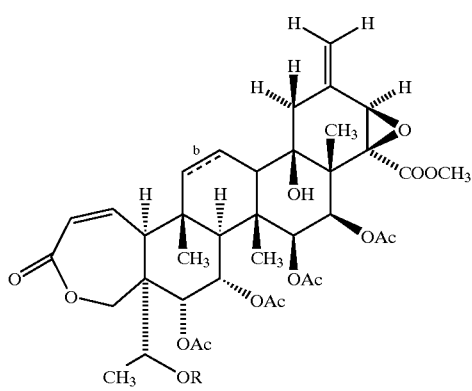

Formula 1(c) b is a single bond and R is OH

Formula 1(d) b is a double bond and R is OH

Analogs of the compounds of Formula 1(a) and 1(b) could be detected in the crude extract and fractions thereof when the process of Example 1 was carried out on a larger scale. Thus, 50 g of ethanol extract were partitioned as described in Example 1 using 900 ml of each solvent at each step.

Partial purification of the methylene chloride extract was achieved by column chromatography on E. Merck silica gel 60 (120 ml), eluting with a step gradient of ethyl acetate in methylene chloride. The step gradient was designed so that the column was washed first with 100% methylene chloride and then with methylene chloride-ethyl acetate mixtures of 9:1, 8:2, 3:2, 2:1, 1:1, 1:2, 2:8 and 1:9. Ultimately the column was washed with 100% ethyl acetate. Fractions eluted with methylene chloride-ethyl acetate 3:2 were enriched in compound of Formula 1(a) and 1(b). These were resolved by HPLC using a Zorbax $RxC_8$ 9 mm×25 cm column, maintained at 50° C. and eluted at 4 ml/min with acetonitrile-water 1:1 v/v. Three identical runs finally afforded 100 mg and 20 mg respectively of 1(a) and 1(b) after crystallization from methanol. Later-eluting fractions from the silica gel column above were found to contain at least two related compounds based on UV spectra and color reactions on TLC plates. Material from the methylene chloride-ethyl actate 1:1 and 1:2 washings were combined and evaporated down. Separation was achieved on the same HPLC column as above, eluting with a 50 minute gradient of 30% to 50% acetonitrile in water. Two identical runs gave 6 mg of purified compound 1(c). Fractions containing the compound of Formula 1(d) were again processed by HPLC (same column) using acetonitrile-water 3:7 delivered isocratically, to yield purified compound of Formula 1(d).

The mass spectra of these compounds were recorded on a Finnigan TSQ700 mass spectrometer (electrospray ionization, ESI). The samples were analyzed by LC/MS using a 2.1×150 mm $C_8$ column at 0.2 ml/min. with a mobile phase of 45% acetonitrile/0.01M aqueous ammonium acetate at 50° C. Component 1(d) had a retention time of 10.5 min. and a molecular weight of 744 which is observed a m/z: 745 (M+H), 762 (M+$NH_3$), 786 (M+H+MeCN). Component 1(c) has a retention time of 11.8 and a molecular weight of 746 which is observed at m/z: 747 (M+H), 764 (M+$NH_3$) and 788 (M+H+MeCN).

The $^{13}C$ NMR spectra obtained for the compound of Formula 1(c) using the conditions previously described is as follows: 15.1 (2x), 16.9, 19.8, 20.8, 20.91, 20.94, 21.9, 22.3, 35.6, 40.6, 42.2, 43.9, 45.0, 47.7, 50.8, 53.5, 55.6, 61.8, 63.5, 66.0, 67.6 (2x), 69.8, 70.0, 73.9, 75.0, 75.6, 119.3, 123.7, 139.0, 144.4, 167.8, 169.2, 169.5, 170.1, 170.4, 171.4 ppm.

The carbon count of 38 is in agreement with the molecular formula $C_{38}H_{50}O_{16}$ derived by scanning HR EI-MS.

EXAMPLE 3

Separation By HPLC

Compounds of this invention were characterized by the following behavior during HPLC separation on a Zorbax $RxC_8$ 4.6 mm×25 cm column, maintained at 50° C. and eluted at 1 ml/min with acetonitrile-water 3:2 v/v):

Compound 1(a): k'=4.15; 1(b): k'=3.30; 1(c): k'=2.30; 1(d): k'=2.10.

Analyses using this HPLC system can be used to quantify the compounds in the crude extract or other mixtures, by comparing the absorbance of HPLC peaks at a wavelength of 220 nm with that produced by injections of known (weighed) amounts of pure standards.

EXAMPLE 4

Additional Purification Procedure

A simplified purification process allows for rapid fractionation of even larger amounts of crude extract and the preparation of gram amounts of the compounds of Formula 1(a) and 1(b).

The ethanol extract is first dissolved at 20 grams per 150 ml in methanol. This solution is diluted with 150 ml of water and then extracted three times with methylene chloride using 150 ml of methylene chloride each time. The pooled methylene chloride extracts are evaporated down and fractionation proceeds by repeated column chromatography on silica gel. One employs methylene chloride-methanol 97:3 in a first step; the mixed compounds of Formula 1(a) and 1(b) thus obtained are resolved by chromatographing on fresh silica gel eluted with methylene chloride-ethyl acetate 3:1. Volume of elution for the compound of Formula 1(a) ranges from about 2 to about 3.5 column volumes of solvent; that for the compound of Formula 1(b) is about 3 to about 4.5 column volumes. Finally, advantage is taken of the low solubility of these compounds, and, after total resolution by chromatography, the compounds of Formula 1(a) and 1(b) can be precipitated and or crystallized from concentrated methanol solutions.

EXAMPLE 5

4,6,7,15,16-pentakis(acetyloxy)-21,22-epoxy-18-hydroxy-20-oxo-22-methoxycarbonyl[6α,7α,15β,16β,21β,22β]D:A-Friedo-2,3,27,30-tetranor-24-oxaoleanane

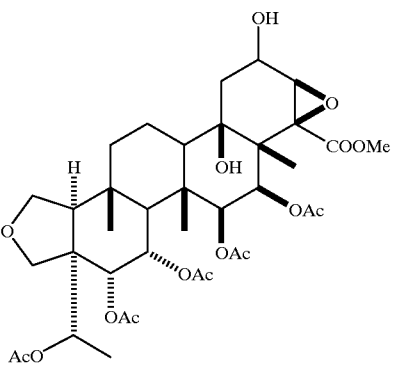

Step A: 4,6,7,15,16-pentakis(acetyloxy)-21,22-epoxy-1,18,20-tris-hydroxy-22-methoxycarbonyl[6α,7α,15β,16β,21β,22β]-D:A-Friedo-2,3,27,30-tetranor-24-oxaoleanane

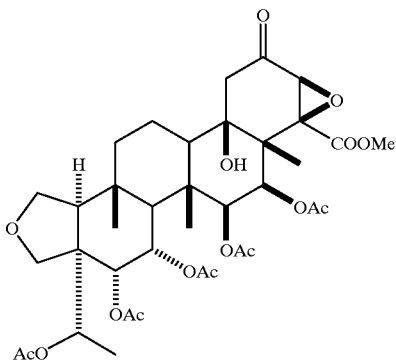

750 mg of 4,6,7,15,16-Pentakis(acetyloxy)-21,22-epoxy-18-hydroxy-22-methoxycarbonyl[6α,7α,15β,16β,21β,22β]-D:A-Friedo-A-homo-27,30-dinor-24-oxaoleana-1,20(29)-dien-3-one (0.95 mmole) were dissolved in a mixture of 20 ml of methanol and 20 ml of dichloromethane. The solution was ozonized at 0° C. for 90 min (Welsbach-Ozonator, T-408, 90V, 0.5 S.L.P.M.) and purged with nitrogen for 15 min. Several small portions of sodium borohydride (250 mg total) were added and the mixture was stirred at room temperature for 1 h. The solution was diluted with 50 ml of dichloromethane, 20 ml of 1N hydrochloric acid was added and the layers were separated. The organic layer was washed with saturated aqueous sodium chloride then was dried over MgSO$_4$ and concentrated. The residue was filtered through a plug of silica gel and then purified by HPLC (Waters RCM, Prep Nova-Pak HR Silica, 2 25×100 mm cartridges) to afford the title compound as a white solid.

$^1$H NMR (CDCl$_3$) δ3.60 (s, 1H, C21-H), 3.63, 4.10 (AB, 2H, J=9.4 Hz, C24-H), 4.31 (m, 1H, C20), 5.21 (m, 1H, C1-H); $^{13}$C NMR (CDCl$_3$) δ53.2 (COOMe), 100.1 (C1); Mass Spectrum (APCI): m/e 786 (M+NH$_4$).

Step B: 4,6,7,15,16-pentakis(acetyloxy)-21,22-epoxy-18,20-dihydroxy-22-methoxycarbonyl[6α,7α,15β,16β,21β,22β]-D:A-Friedo-2,3,27,30-tetranor-24-oxaoleanane

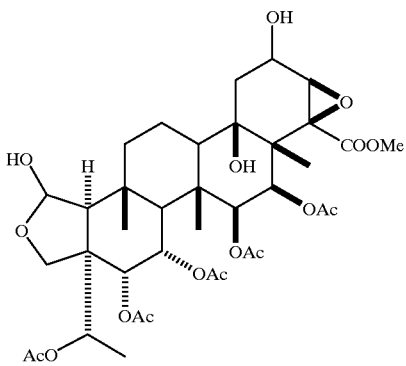

50 mg of 4,6,7,15,16-pentakis(acetyloxy)-21,22-epoxy-1,18,20-tris-hydroxy-22-methoxycarbonyl[6α,7α,15β,16β,21β,22β]-D:A-Friedo-2,3,27,30-tetranor-24-oxaoleanane (0.065 mmole) were dissolved in 2 ml of dichloromethane. 0.25 ml of triethylsilane (2.0 mmole) were added followed by 0.25 ml of BF$_3$.OEt$_2$ (1.58 mmole). After 1 h, 5 ml of aqueous sodium bicarbonate solution and 20 ml of dichloromethane were added. The organic layer was separated and washed with saturated aqueous sodium chloride then was dried over MgSO$_4$ and concentrated. The residue was filtered through a plug of silica gel and then purified by HPLC (Waters RCM, Prep Nova-Pak HR Silica, 2 25×100 mm cartridges) using a mixture of 8:4:1 hexane: tbutylmethyl ether: acetonitrile to afford the title compound as a white solid.

$^1$H NMR (CDCl$_3$) δ3.62 (s, 1H, C21-H), 3.60, 3.85 (AB, 2H, J=9.4 Hz, C24-H), 3.60, 3.89 (2×m, 2H, C1-H), 4.32 (m, 1H, C20-H); Mass Spectrum (APCI): m/e 770 (M+NH$_4$).

Step C: 4,6,7,15,16-pentakis(acetyloxy)-21,22-epoxy-18-hydroxy-20-oxo-22-methoxycarbonyl[6α,7α,15β,16β,21β,22β]D:A-Friedo-2,3,27,30-tetranor-24-oxaoleanane

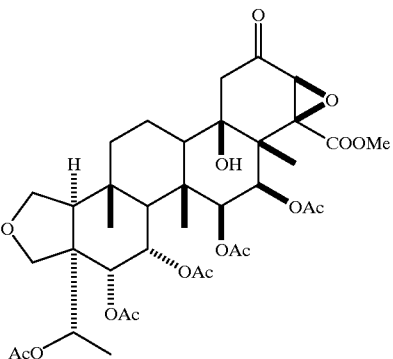

To a mixture of pyridinium chlorochromate (115 mg, 0.526 mmol), sodium acetate (788 mg, 3.51 mmol) and powdered 4 Å molecular sieves (57 mg) in 1.5 ml of dichloromethane at rt was added 20 mg of 4,6,7,15,16-pentakis(acetyloxy)-21,22-epoxy-18,20-dihydroxy-22-methoxycarbonyl[6α,7α,15β,16β,21β,22β]D:A-Friedo-10 2,3,27,30-tetranor-24-oxaoleanane (0.027 mmol) dissolved in 1 ml of dichloromethane. The reaction mixture was stirred for 24 hr whereupon it was diluted with ethyl acetate (20 ml) and filtered through a thin pad of silica gel, eluting with ethyl acetate. The residue was then purified by HPLC (Waters RCM, Prep Nova-Pak HR Silica, 2 25×100 mm cartridges) to afford the title compound.

$^1$H NMR (CDCl$_3$) δ2.41, 2.83 (AB, 2H, J=13.9 Hz, C19-H), 3.59, 3.84 (AB, 2H, J=8.9 Hz, C24-H), 3.61, 3.86 (ABX, 2H, J$_{AB}$=8.9 Hz, J$_{AX}$=6.9 Hz, J$_{BX}$=1.0 Hz, C1-H).

¹³C NMR (CDCl₃) δ201.1 (C20); Mass Spectrum (APCI): m/e 768 (M+NH₄).

EXAMPLE 6

[3a-S-3aα,3bβ,5aα,9β,9aβ,10α,11α,11aα]-11a-(1-R-acetoxyethyl)-6-oxo-9,10,11-triacetoxy-3b,7,9a-trimethyl-1,3,3a,3b,4,5,5a,6,9,9a,9b,10,11,11a-tetradecahydrophenanthro[1,2-c]furan

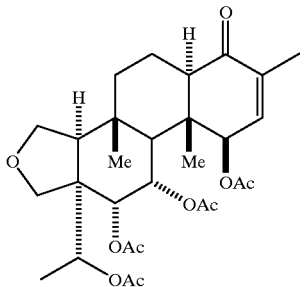

A solution of 4,6,7,15,16-pentakis(acetyloxy)-21,22-epoxy-18-hydroxy-20-oxo-22-methoxycarbonyl[6α,7α,15β,16β,21β,22β]D:A-Friedo-2,3,27,30-tetranor-24oxaoleanane (Example 5) (219 mg, 0.29 mmol) and LiCl (42.4 mg, 2.9 mmol) in 5.0 ml of DMSO was heated at 130° C. for 6 h and was poured into ether. The organic layer was washed with brine twice, dried with MgSO₄ and filtered through a plug of silica gel. Upon removal of solvent, it was purified by HPLC to give the title compound.

¹H NMR (CDCl₃) δ6.16 (s, 1H), 5.72 (q, 1H, J=6.1 Hz), 5.54 (d of d, 1H, J=6.4, 3.1 Hz), 5.50 (bs, 1H), 5.27 (d, 1H, J=3.9 Hz), 3.90 (d, 1H, J=9.6 Hz), 3.82 (d, 1H, J=9.2 Hz), 3.64 (d, 1H, J=9.2 Hz), 3.58 (d of d, 1H, J=9.6, 7.1 Hz), 2.26 (d of d, 1H, J=12.2, 3.5 Hz), 2.10 (s, 3H), 2.06 (s, 3H), 2.02 (s, 3H), 2.01 (s, 3H), 1.77 (s, 3H), 1.25 (d, 3H, J=6.4 Hz), 1.118 (s, 3H), 1.113 (s, 3H). Mass Spectrum (APCI): m/e 566 (M+NH₄).

EXAMPLE 7

[3a-S-3aα,3bβ,5aα,9β,9aβ,10α,11α,11aα]-11a-(1-R-acetoxyethyl)-6-benzyl-6-hydroxy-9,10,11-triacetoxy-3b,7,9a-trimethyl-1,3,3a,3b,4,5,5aα,6,9,9aα,9b,10,11,11a-tetradecahydrophenanthro]1,2-c]furan

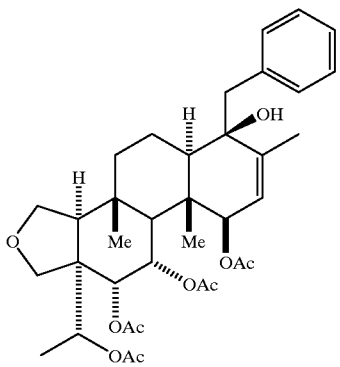

The Grignard reagent is formed by adding the halide (benzyl chloride) in THF solution to an excess of magnesium in THF at room temperature under a nitrogen atmosphere and then refluxing for 1 hr. To a solution of the ketone from Example 6 (10 mg, 0.018 mmol) in 0.5 ml of THF was added benzylmagnesium chloride (0.12 ml, 1.0 M in ether) at rt. After 2 h, it was quenched with 3 drops of pH =7 buffer and the wet solution was filtered through silica gel. Upon removal of the solvent the residue was purified by HPLC to give the title compound.

¹H NMR (CDCl₃) δ7.29–7.34 (m, 3H), 7.09 (d, 2H, J=7.1 Hz), 5.54–5.50 (m, 2H), 5.24 (d, 1H, J=3.6 Hz), 5.19 (s, 1H), 4.79 (s, 1H), 3.86 (d, 1H, J=9.4 Hz), 3.82 (d, 1H, J=7.2 Hz), 3.57–3.61 (m, 2H), 3.12 (d, 1H, J=14.4 Hz), 2.88 (d, 1H, J=14.4 Hz), 2.05 (s, 3H), 1.99 (bs, 6H), 1.96 (bs, 6H), 1.25 (s, 3H), 1.20 (d, 3H, J=6.1 Hz), 1.13 (s, 3H). Mass Spectrum (APCI): m/e 658 (M+NH₄).

EXAMPLE 8

[3a-S-3aα,3bβ,5aα,9β,9aβ,10α,11α,11aα]-11a-(1-R-acetoxyethyl)-6-n-butyl-6-hydroxy-9,10,11-triacetoxy-3b,7,9a-trimethyl-1,3,3a,3b,4,5,5a,6,9,9a9b,10,11,11a-tetradecahydrophenanthro[1,2-c]furan

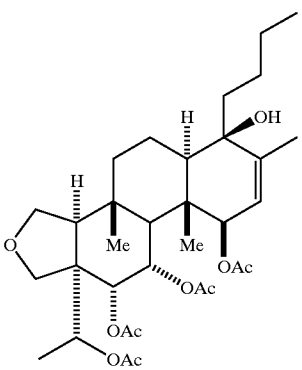

The title compound was prepared as in Example 7.

¹H NMR (CDCl₃) δ5.71 (q, 1H, J=6.4 Hz), 5.59 (d of d, 1H, J=6.2, 4.2 Hz), 5.27 (d, 1H, J=3.9 Hz), 5.15 (bs, 1H), 5.05 (bs, 1H), 3.90 (d, 1H, J=6.2, 4.2 Hz), 3.84 (d, 1H, J=9.0 Hz), 3.64 (d, 1H, J=9.0 Hz), 3.59 (d of d, 1H, J=9.4, 7.1 Hz), 2.10 (s, 3H), 2.03 (s, 3H), 2.01(s, 3H), 1.98 (s, 3H), 1.70 (s, 3H), 1.25 (s, 3H), 1.24 (d, 3H, J=6.2 Hz), 1.15 (s, 3H), 0.93 (t, 3H, J=7.3 Hz). Mass Spectrum (APCI): m/e 624 (M+NH₄).

EXAMPLE 9

[3a-S-3aα,3bβ,5aα,9β,9aβ,10α,11α,11aα]-11a-(1-R-acetoxyethyl)-6-(3-phenyl-n-propyl)-6-hydroxy-9,10,11-triacetoxy-3b,7,9a-trimethyl-1,3,3a,3b,4,5,5a,6,9,9a,9b,10,11,11a-tetradecahydrophenanthro[1,2-c]furan

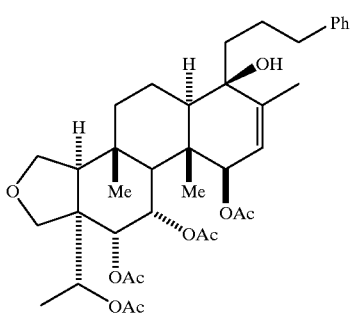

The title compound was prepared by procedures described in Example 7.

¹H NMR (CDCl₃) δ7.28 (t, 2H, J=7.8 Hz), 7.17 (t, 1H, J=7.0 Hz), 7.18 (d, 2H, J=7.4 Hz), 5.68 (q, 1H, J=6.4 Hz), 5.57 (d of d, 1H, J=5.7, 3.9 Hz), 5.25 (d, 1H, J=3.7 Hz), 5.12 (bs, 1H), 5.02 (bs, 1H), 3.88 (d, 1H, J=9.2 Hz), 3.83 (d, 1H, J=9.2 Hz), 3.62 (d, 1H, J=9.2 Hz), 3.58 (d of d, 1H, J=9.2, 7.1 Hz), 2.53–2.65 (m, 2H), 2.10 (s, 3H), 2.01 (s, 3H), 2.00 (s, 3H), 1.96 (s, 3H), 1.58 (bs, 3H), 1.26 (s, 3H), 1.23 (d, 3H, J=6.4 Hz), 1.21 (s, 3H), 1.12 (s, 3H). Mass Spectrum (APCI): m/e 686 (M+NH₄).

EXAMPLE 10

[3a-S-3aα,3bβ,5aα,9β,9aβ,10α,11α,11aα]-11a-(1-R-acetoxyethyl)-6-(2-phenethyl)-6-hydroxy-9,10,11-triacetoxy-3b,7,9a-trimethyl-1,3,3a,3b,4,5,5a,6,9,9a9b,10,11,11a-tetradecahydrophenanthro[1,2-c]furan

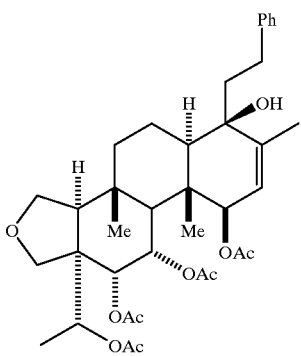

Step A: Preparation of [3a-S-3aα,3bβ,5aα,9β,9aβ,10α,11α,11aα11aα]-11a-(1-R-acetoxyethyl)-6-(2-phenylacetylenyl)-6-hydroxy-9,10,11-triacetoxy-3b,7,9a-trimethyl-1,3,3a,3b,4,5,5a,6,9,9a,9b,10,11,11a-tetradecahydrophenanthro[1,2-c]furan

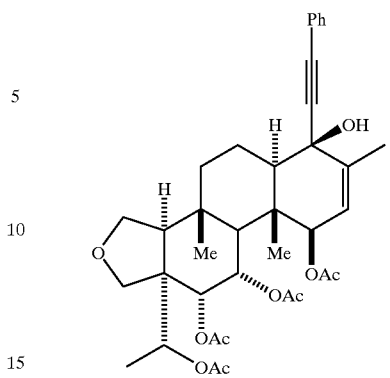

The title compound was prepared by procedures described in Example 7.

¹H NMR (CDCl₃) δ7.40–7.42 (m, 2H), 7.30–7.33 (m, 3H), 5.73 (q, 1H, J=6.4 Hz), 5.60 (d of d, 1H, J=6.2, 4.1 Hz), 5.29 (d, 1H, J=3.9 Hz), 5.23 (bs, 1H), 5.19 (bs, 1H), 3.92 (d, 1H, J=9.4 Hz), 3.83 (d, 1H, J=9.2 Hz), 3.64 (d, 1H, J=9.2 Hz), 3.59 (d of d, 1H, J=9.4, 7.1 Hz), 2.09 (s, 3H), 2.04 (s, 3H), 2.01 (s, 3H), 2.00 (s, 3H), 1.98 (bs, 3H), 1.25 (s, 3H), 1.24 (d, 3H, J=6.4 Hz), 1.18 (s, 3H). Mass Spectrum (APCI): m/e 668 (M+NH₄).

Step B: Preparation of [3a-S-3aα,3bβ,5β,9β,9aβ, 10α,11α, 11aα]-11a-(1-R-acetoxyethyl)-6-(2-phenethyl)-6-hydroxy-9,10,11-triacetoxy-3b,7,9a-trimethyl-1,3,3a,3b,4,5,6a,6,9, 9a,9b,10,11,11a-tetradecahydrophenanthro[1,2-c]furan

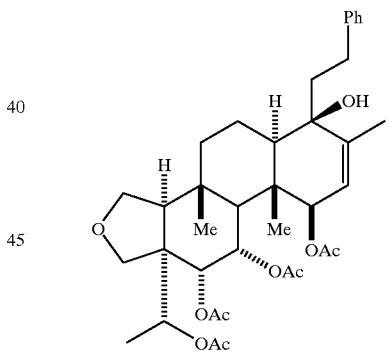

To a solution of the compound from Step A (4.3 mg, 0.07 mmol) in 5 ml of EtOAc was added 4 mg of palladium on carbon (10%). The mixture in a Parr apparatus was pressurized with hydrogen to 50 PSI for 14 h. The solution was filtered through a plug of silica gel and dried to give the title compound.

¹H NMR (CDCl₃) δ7.30 (t, 2H, J=7.5 Hz), 7.17–7.21 (m, 3H), 5.71 (q, 1H J=6.2 Hz), 5.60 (d of d, 1H, J=5.9, 3.9 Hz), 5.27 (d, 1H, J=3.6 Hz), 5.25 (bs, 1H), 5.10 (bs, 1H), 3.89 (d, 1H, J=9.4 Hz), 3.84 (d, 1H, J=9.2 Hz), 3.64 (d, 1H, J=9.2 Hz), 3.59 (d of d, 1H, J=9.4, 7.1 Hz), 2.30–2.45 (m, 2H), 2.12 (s, 3H), 2.05 (s, 3H), 2.02 (s, 3H), 2.00 (s, 3H), 1.80 (bs, 3H), 1.26 (s, 3H), 1.25 (d, 3H, J=6.4 Hz), 1.14 (s, 3H). Mass Spectrum (APCI): m/e 672 (M+NH₄).

EXAMPLE 11

[3a-S-3aα,3bβ,5aα,9β,9aβ,10α,11α,11aα]-11a-(1-R-acetoxyethyl)-6-(2phenethyl)-6-hydroxy-9,10,11-triacetoxy-3b,7,9a-trimethyl-1,3,3a,3b,4,5,5a,6,7,8,9,9a,9b,10,11,11a-hexadecahydrophenanthro[1,2-c]furan

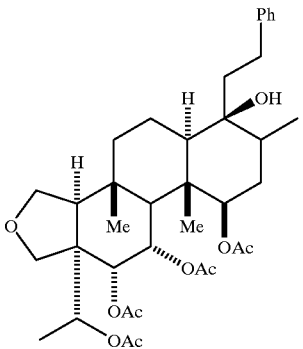

Step A: Preparation of [3a-S-3aα,3bβ,5aα,9β,9aβ,10α,11α,11aα]-11a (1-R-acetoxyethyl)-6-oxo-9,10,11-triacetoxy-3b,7,9a-trimethyl-1,3,3a,3b,4,5,5a,6,7,8, 9,9a,9b,10,11,11a-hexa-decahydrophenanthro[1,2-c]furan

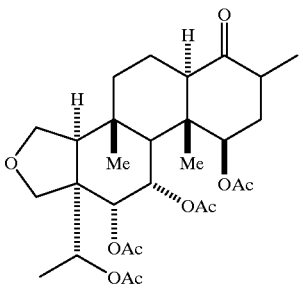

To a solution of [3a-S-3aα,3bβ,5aα,9β,9aβ,10α,11α,11aα]-11a -(1-R-acetoxyethyl)-6-oxo-9,10,11-triacetoxy-3b,7,9a-trimethyl-1,3,3a,3b,4,5,5a,6,9,9a,9b,10,11,11a-tetradecahydrophenanthro[1,2-c]furan (Example 6) (10.0 mg, 0.018 mmol) in 5 ml of MeOH was added 2 mg of Palladium on carbon (10%) The mixture in a Parr apparatus was pressurized with hydrogen to 50 psi for 14 h. The solution was filtered through a plug of silica gel and dried to give the title compound.

$^1$H NMR (CDCl$_3$) δ5.74 (q, 1H, J=6.2 Hz), 5.51 (d of d, 1H, J=6.1, 3.8 Hz), 5.24 (d, 1H, J=3.9 Hz), 5.07 (d of d, 1H, J=10.5, 5.3 Hz), 3.87 (d, 1H, J=9.6 Hz), 3.81 (d, 1H, J=9.2 Hz), 3.62 (d, 1H, J=9.2 Hz), 3.56 (d of d, 1H, J=9.3, 7.1Hz), 2.59–2.49 (m, 2H), 2.22 (d of d, 1H, J=11.9, 2.3 Hz), 2.09 (s, 3H), 2.04 (s, 3H), 1.99 (s, 3H), 1.94 (s, 3H), 1.77 (s, 3H), 1.23 (d, 3H, J=6.2 Hz), 1.12 (s, 3H), 1.06 (s, 3H), 0.94 (d, 3H, J=5.9 Hz). Mass Spectrum (APCI): m/e 568 (M+NH$_4$).

Step B: Preparation of [3a-S-3aα,3bβ,5aα,9β,9aβ,10α,11α,11aα]-11a -(1-R-acetoxyethyl)-6-(2-phenylacetylenyl)-6-hydroxy-9,10,11-triacetoxy-3b,7,9a-trimethyl-1,3,3a,3b,4,5,5a,6,7,8,9,9a,9b,10,11,11a-hexadecahydrophenanthro[1,2-c]furan

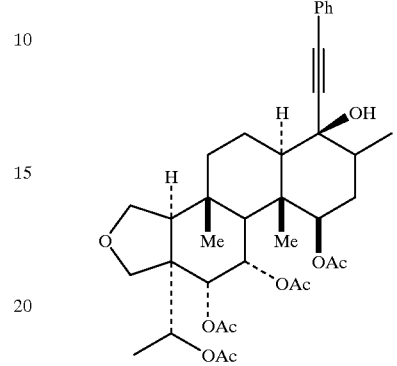

The title compound was prepared according to procedures described in Example 7.

$^1$H NMR (CDCl$_3$) δ7.35–7.38 (m, 2H), 7.26–7.31 (m, 3H), 5.71 (q, 1H, J=6.4 Hz), 5.54 (d of d, 1H, J=6.2, 3.9 Hz), 5.24 (d, 1H, J=3.9 Hz), 4.67 (d of d, 1H, J=11.0, 4.8 Hz), 3.87 (d, 1H, J=9.6 Hz), 3.78 (d, 1H, J=9.2 Hz), 3.60 (d, 1H, J=9.2 Hz), 3.54 (d of d, 1H, J=9.6, 7.4 Hz), 2.06 (s, 3H), 2.00 (s, 3H), 1.97 (s, 3H), 1.91 (s, 3H), 1.26 (s, 3H), 1.20 (d, 3H, J=6.4 Hz) 1.13 (s, 3H), 1.08 (d, 3H, J=6.4 Hz), Mass Spectrum (APCI): m/e 670 (M+NH$_4$).

Step C: Preparation of [3a-S-3aα,3bβ,5aα,9β,9aβ,10α,11α,11aα]-11a -(1-R-acetoxyethyl)-6-(2-phenethyl)-6-hydroxy-9,10,11-triacetoxy-3b,7,9a-trimethyl-1,3,3a,3b,4,5,5a,6,7,8,9,9a,9b,10,11,11a-hexadecahydrophenanthro[1,2-c]furan

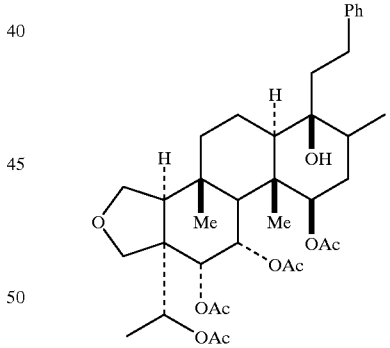

The title compound was prepared according to procedures described in Example 10, Step B.

$^1$H NMR (CDCl$_3$) δ7.28 (t, 2H, J=7.8 Hz), 7.18 (t, 1H, J=7.3 Hz), 7.15 (d, 2H, J=7.4 Hz), 5.71 (q, 1H, J=6.4 Hz), 5.57 (d of d, 1H, J=6.0, 3.9 Hz), 5.24 (d, 1H, J=3.9 Hz), 4.64 (d of d, 1H, J=10.5, 4.3 Hz), 3.87 (d, 1H, J=9.6 Hz), 3.81 (d, 1H, J=9.2 Hz), 3.61 (d, 1H, J=9.2 Hz), 3.56 (d of d, 1H, J=9.6, 7.1 Hz), 2.45–2.50 (m, 1H), 2.34–2.39 (m, 1H), 2.09 (s, 3H), 2.01 (s, 3H), 1.99 (s, 3H), 1.92 (s, 3H), 1.29 (s, 3H), 1.22 (d, 3H, J=6.2 Hz), 1.13 (s, 3H), 0.88 (d, 3H, J=6.4 Hz). Mass Spectrum (APCI): m/e 674 (M+NH$_4$).

EXAMPLE 12

[3a-S-3aα,3bβ,5aα,9β,9aβ,10α,11α,11aα]-11a(1-R-acetoxyethyl)-6-(2-phenethyl)-9,10,11-triacetoxy-3b,7,9a-trimethyl-1,3,3a,3b,4,5,7,8,9,9a,9b,10,11,11a-tetradecahydrophenanthro[1,2-c]furan

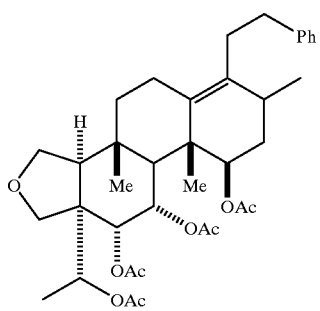

To a solution of [3a-S-3aα,3bβ,5aα,9β,9aβ,10α,11α,11aα]-11a -(1-R-acetoxyethyl)-6-(2-phenethyl)-6-hydroxy-9,10,11-triacetoxy-3b,7,9a-trimethyl-1,3,3a,3b,4,5,5a,6,7,8,9,9a,9b,10,11,11a-hexadecahydro phenanthro[1,2-c]furan (Example 11, 17 mg, 0.026 mmol) in 0.5 ml of pyridine was added SOCl$_2$ (1 ml) and the solution was stirred at rt for 2 h. It was poured into 1 N H$_2$SO$_4$ and was extracted with ether. The organic layer was washed with aqueous NaHCO$_3$ and water, dried with MgSO$_4$ and filtered through a plug of silica gel and the residue was purified by HPLC to give the title compound.

$^1$H NMR (CDCl$_3$) δ7.29 (t, 2H, J=7.6 Hz), 7.18 (d, 2H, J=6.8 Hz), 7.14 (t, 1H, J=7.3 Hz), 5.62 (q, 1H, J=6.3 Hz), 5.54 (d of d, 1H, J=6.4, 4.1 Hz), 5.50 (d, 1H, J=4.5 Hz), 4.72 (d of d, 1H, J=11.4, 3.4 Hz), 3.82 (d, 2H, J=9.2 Hz), 3.62 (d, 1H, J=9.2 Hz), 3.56 (d of d, 1H, J=9.2, 7.1 Hz), 2.69–2.7 (m, 1H), 2.56–2.62 (m, 1H), 2.13 (s, 3H), 2.05 (s, 3H), 2.00 (s, 3H), 1.9 (s, 3H), 1.30 (s, 3H), 1.24 (d, 3H, J=6.4 Hz), 1.20 (s, 3H), 1.09 (d, 3H, J=6.9 Hz). Mass Spectrum (APCI): m/e 656 (M+NH$_4$).

By procedures described in the preceeding examples, the following compounds can be prepared (Examples 13–47).

EXAMPLE 13

[3a-S-3aα,3bβ,5aα,9β,9aβ,10α,11α,11aα]-11a-(1-R-acetoxyethyl)-6-(2-(2-methoxyphenyl)ethyl)-6-hydroxy-9,10,11-triacetoxy-3b,7,9a-trimethyl-1,3,3a,3b,4,5,5a,6,9,9a,9b,10,11,11a-tetradecahydrophenanthro[1,2-c]furan

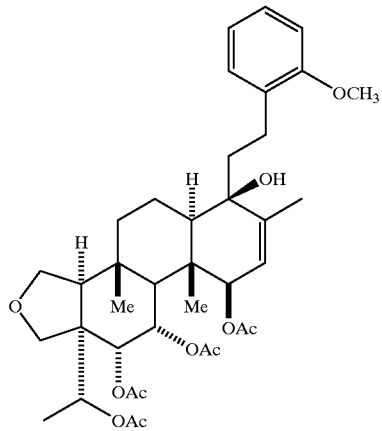

EXAMPLE 14

[3a-S-3aα,3bβ,5aα,9β,9aβ,10α,11α,11aα]-11a-(1-R-acetoxyethyl)-6-(2-(2-ethoxyphenyl)ethyl))-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

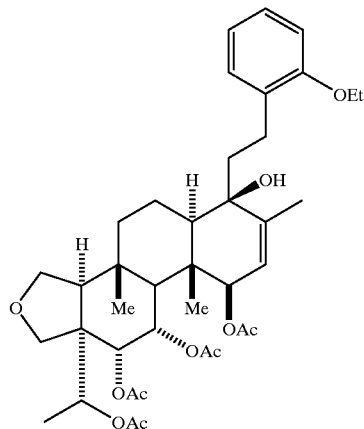

EXAMPLE 15

[3a-S-3aα,3bβ,5aα,9β,9aβ,10α,11α,11aα]-11a-(1-R-acetoxyethyl)-6-(2-(2-n-butyloxyphenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

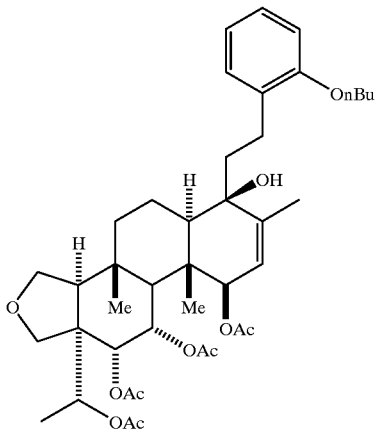

EXAMPLE 16

[3a-S-3aα,3bβ,5aα,9β,9aβ,10α,11α,11aα]-11a-(1-R-acetoxyethyl)-6-(2-(2-allyloxyphenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

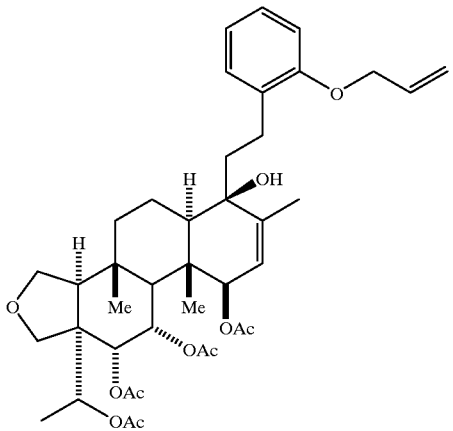

EXAMPLE 17

[3a-S-3aα,3bβ,5aα,9β,9aβ,10α,11α,11aα]-11a-(1-R-acetoxyethyl)-6-(2-(2-benzyloxyphenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

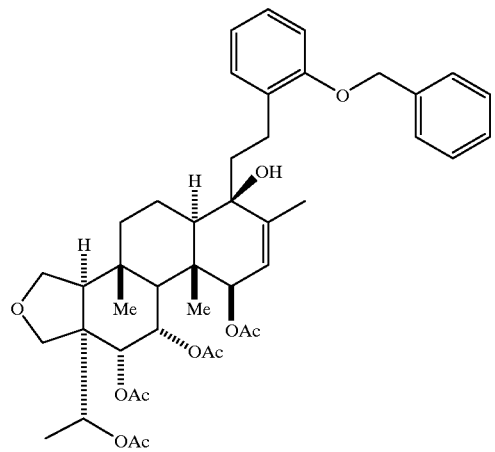

EXAMPLE 18

[3a-S-3aα,3bβ,5aα,9β,9aβ,10α,11α,11aα]-11a-(1-R-acetoxyethyl)-6-(but-3-en-1-yl)-6-hydroxy-9,10,11-triacetoxy-3b,7,9a-trimethyl-1,3,3a, 3b,4,5,5a,6,9,9a,9b,10,11,11a-tetradecahydro phenanthro[1,2-c]furan

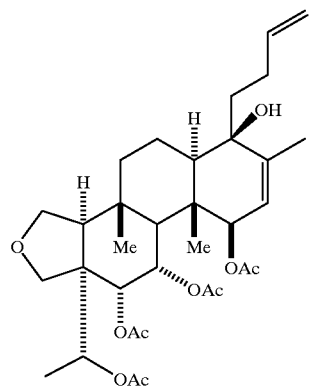

EXAMPLE 19

[3a-S-3aα,3bβ,5aα,9β,9aβ,10α,11α,11aα]-11a-(1-R-acetoxyethyl)-6-(4-dimethyl-pent-3-en-1-yl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

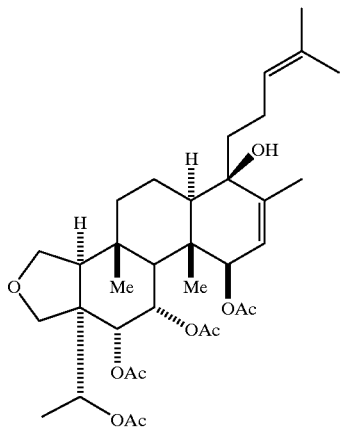

EXAMPLE 20

[3a-S-3aα,3bβ,5aα,9β,9aβ,10α,11α,11aα]-11a-(1-R-acetoxyethyl)-6-(2-(2-fluorophenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

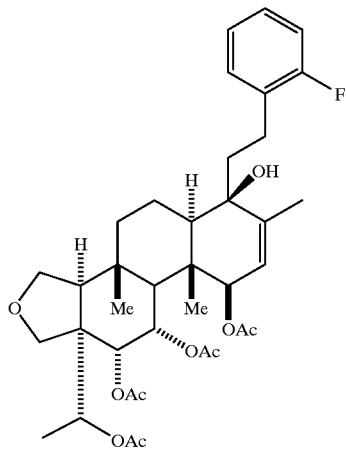

EXAMPLE 21

[3a-S-3aα,3bβ,5aα,9β,9aβ,10α,11α,11aα]-11a-(1-R-acetoxyethyl)-6-(2-(2,6-difluorophenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

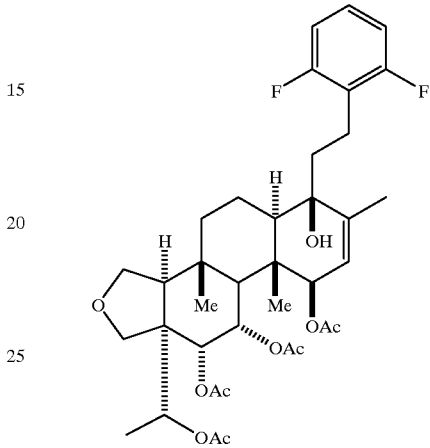

EXAMPLE 22

[3a-S-3aα,3bβ,5aα,9β,9aβ,10α,11α,11aα]-11a-(1-R-acetoxyethyl)-6-(2-(2-chlorophenyl)ethyl)-6-hydroxy-9,10,11-triacetoxy-3b,7,9a-trimethyl-1,3,3a,3b,4,5,5a,6,9,9a,9b 10,11,11a-tetradecahydro phenanthro[1,2-c]furan

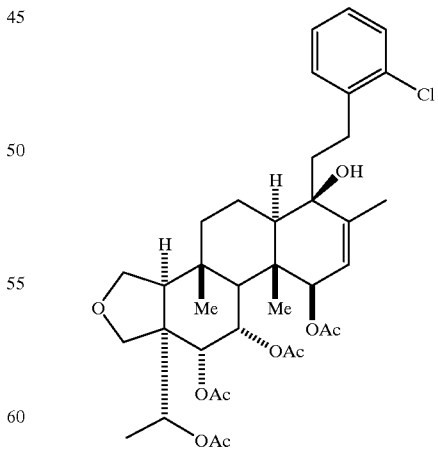

EXAMPLE 23

[3a-S-3aα,3bβ,5aα,9β,9aβ,10α,11α,11aα]-11a-(1-R-acetoxyethyl)-6-(2-(3-chlorophenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

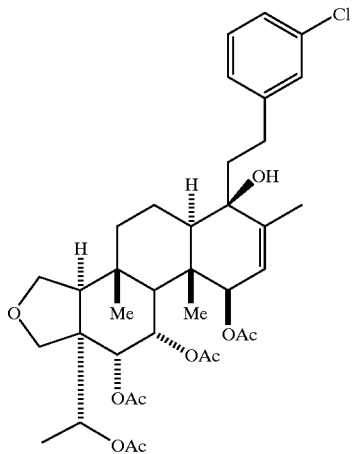

EXAMPLE 24

[3a-S-3aα,3bβ,5aα,9β,9aβ,10α,11α,11aα]-11a-(1-R-acetoxyethyl)-6-(2-(4-chlorophenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

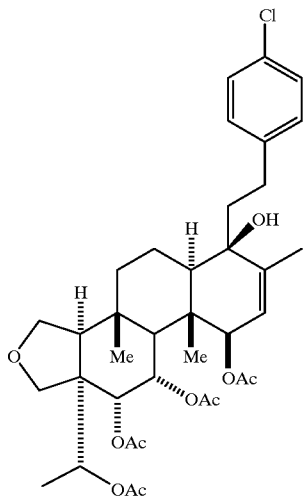

EXAMPLE 25

[3a-S-3aα,3bβ,5aα,9β,9aβ,10α,11α,11aα]-11a-(1-R-acetoxyethyl)-6-(2-(3,4-dichlorophenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

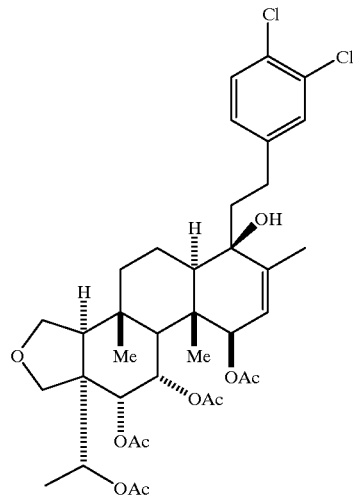

EXAMPLE 26

[3a-S-3aα,3bβ,5aα,9β,9aβ,10α,11α,11aα]-11a-(1-R-acetoxyethyl)-6-(2-(2-methylphenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

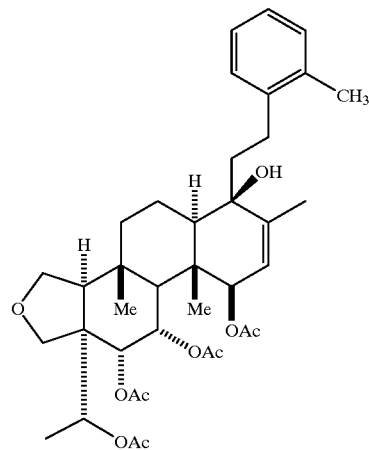

EXAMPLE 27

[3a-S-3aα,3bβ,5aα,9β,9aβ,10α,11α,11aα]-11a-(1-R-acetoxyethyl)-6-(2-(3-methylphenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

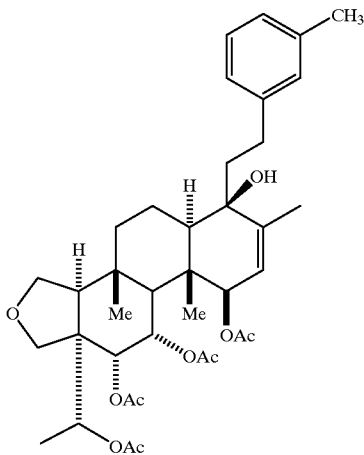

EXAMPLE 28

[3a-S-3aα,3bβ,5aα,9β,9aβ,10α,11α,11aα]-11a-(1-R-acetoxyethyl)-6-(2-(4-methylphenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

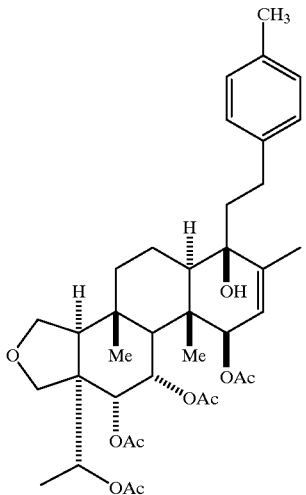

EXAMPLE 29

[3a-S-3aα,3bβ,5aα,9β,9aβ,10α,11α,11aα]-11a-(1-R-acetoxyethyl)-6-(2-(2-trifluoromethylphenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

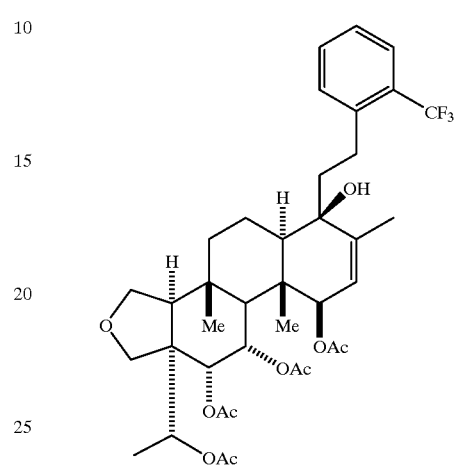

EXAMPLE 30

[3a-S-3aα,3bβ,5aα,9β,9aβ,10α,11α,11aα]-11a-(1-R-acetoxyethyl)-6-(2-(3-trifluoromethylphenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

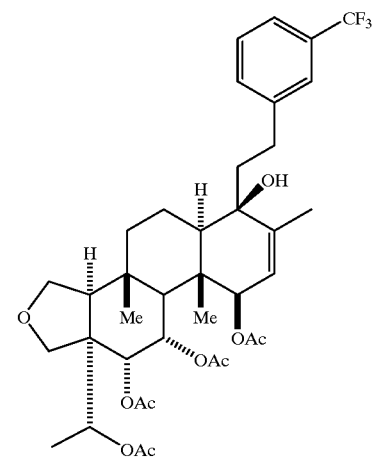

EXAMPLE 31

[3a-S-3aα,3bβ,5aα,9β,9aβ,10α,11α,11aα]-11a-(1-R-acetoxyethyl)-6-(2-naphth-2-ylethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

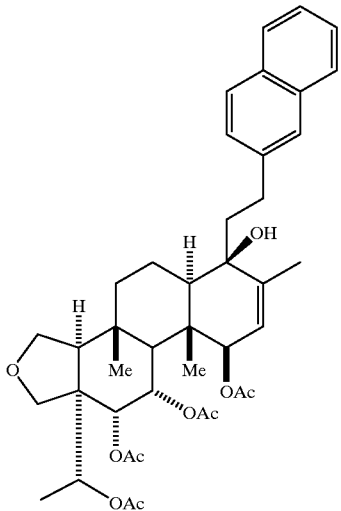

EXAMPLE 32

[3a-S-3aα,3bβ,5aα,9β,9aβ,10α,11α,11aα]-11a-(1-R-acetoxyethyl)-6-(2-naphth-1-ylethyl)-6-hydroxy-9,10,11-triacetoxy-3b,7,9a-trimethyl-1,3,3a,3b,4,5,5a,6,9,9a,10,11,11a-tetradecahydro phenanthro[1,2-c]furan

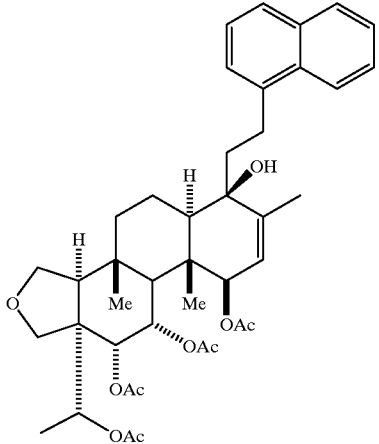

EXAMPLE 33

[3a-S-3aα,3bβ,5aα,9β,9aβ,10α,11α,11aα]-11a-(1-R-acetoxyethyl)-6-(2-(3-methoxyphenyl)ethyl))-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

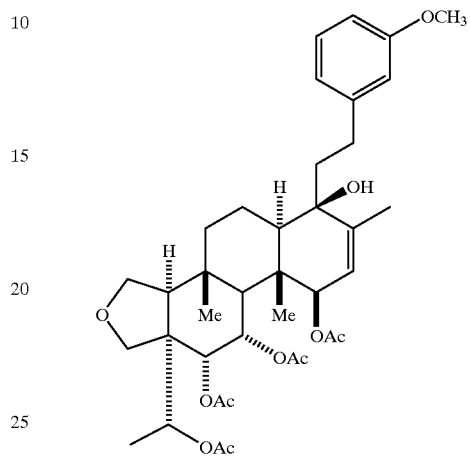

EXAMPLE 34

[3a-S-3aα,3bβ,5aα,9β,9aβ,10α,11α,11aα]-11a-(1-R-acetoxyethyl)-6-(2-(4-methoxyphenyl)ethyl))-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

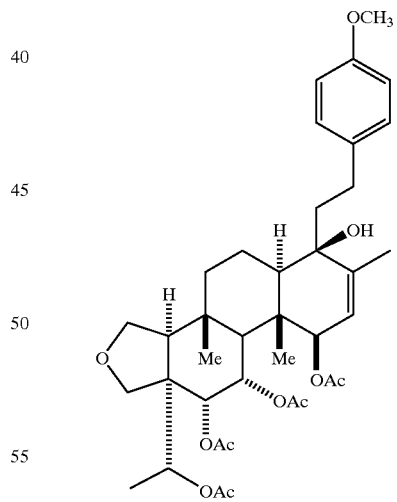

EXAMPLE 35

[3a-S-3aα,3bβ,5aα,9β,9aβ,10α,11α,11aα]-11a-(1-R-acetoxyethyl)-6-(2-(2,3-dimethoxyphenyl)ethyl))-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

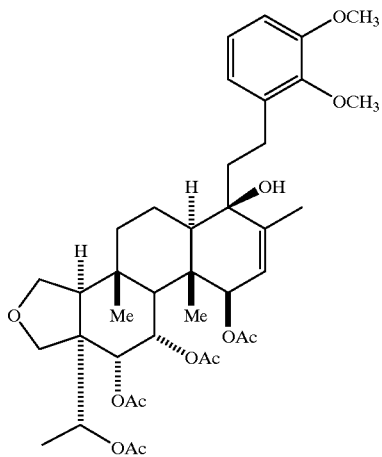

EXAMPLE 36

[3a-S-3aα,3bβ,5aα,9β,9aβ,10α,11α,11aα]-11a-(1-R-acetoxyethyl)-6-(2-(3,4-dimethoxyphenyl)ethyl))-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

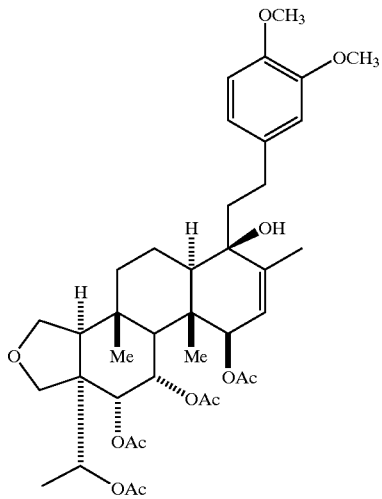

EXAMPLE 37

[3a-S-3aα,3bβ,5aα,9β,9aβ,10α,11α,11aα]-11a-(1-R-acetoxyethyl)-6-(2-(2,5-dimethoxyphenyl)ethyl))-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

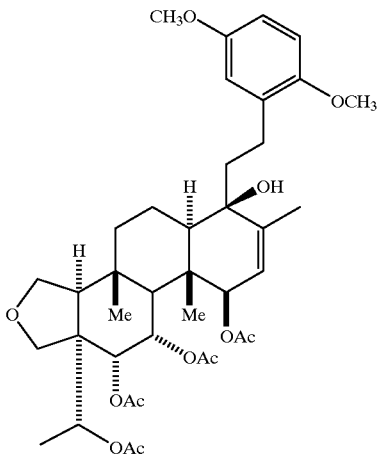

EXAMPLE 38

[3a-S-3aα,3bβ,5aα,9β,9aβ,10α,11α,11aα]-11a-(1-R-acetoxyethyl)-6-(2-(3,5-dimethoxyphenyl)ethyl))-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

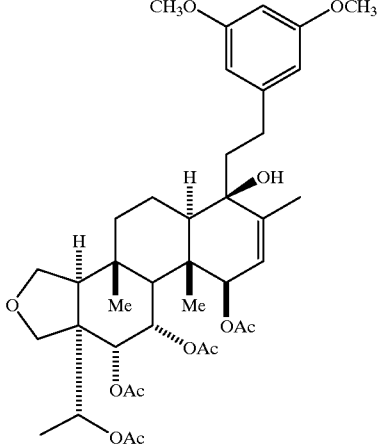

EXAMPLE 39

[3a-S-3aα,3bβ,5aα,9β,9aβ,10α,11α,11aα]-11a-(1-R-acetoxyethyl)-6-(2-(3,4-methylenedioxyphenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

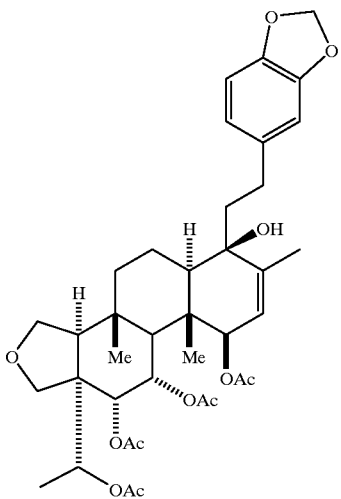

EXAMPLE 40

[3a-S-3aα,3bβ,5aα,9β,9aβ,10α,11α,11aα]-11a-(1-R-acetoxyethyl)-6-(2-(2,3-methylenedioxyphenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

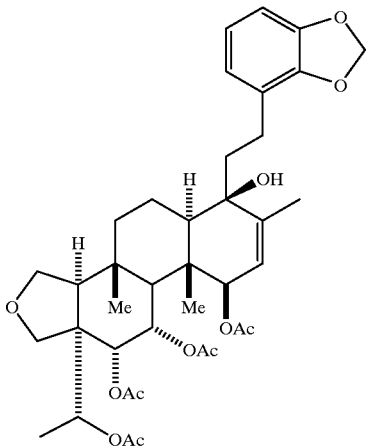

EXAMPLE 41

[3a-S-3aα,3bβ,5aα,9β,9aβ,10α,11α,11aα]-11a-(1-R-acetoxyethyl)-6-(2-(4-dimethylaminophenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

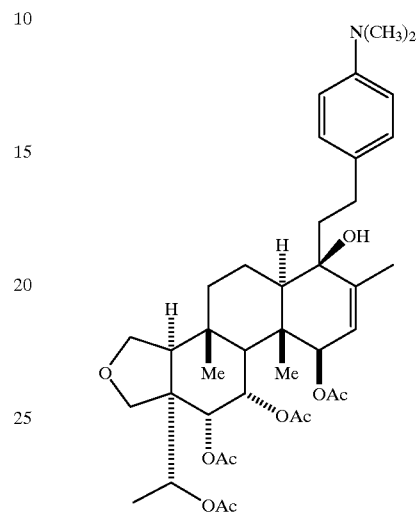

EXAMPLE 42

[3a-S-3aα,3bβ,5aα,9β,9aβ,10α,11α,11aα]-11a-(1-R-acetoxyethyl)-6-(2,2-diphenylethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

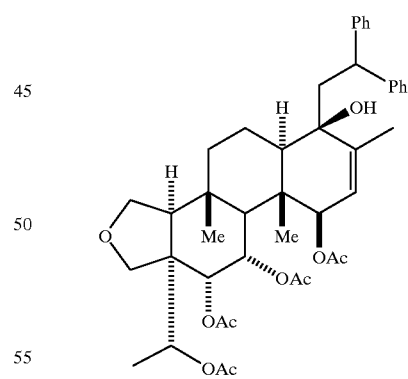

EXAMPLE 43

[3a-S-3aα,3bβ,5aα,9β,9aβ,10α,11α,11aα]-11a-(1-R-acetoxyethyl)-6-(2-(2-methoxy-5-methylphenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

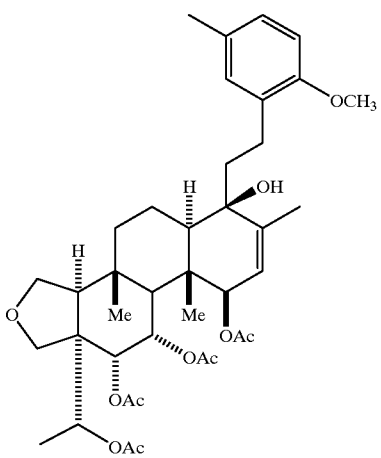

EXAMPLE 44

[3a-S-3aα,3bβ,5aα,9β,9aβ,10α,11α,11aα]-11a-(1-R-acetoxyethyl)-6-(2-(thien-2-yl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

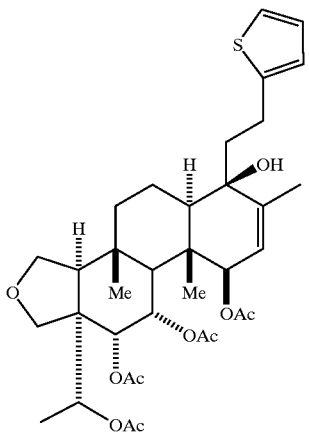

EXAMPLE 45

[3a-S-3aα,3bβ,5aα,9β,9aβ,10α,11α,11aα]-11a-(1-R-acetoxyethyl)-6-(2-(2,6-dimethoxyphenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

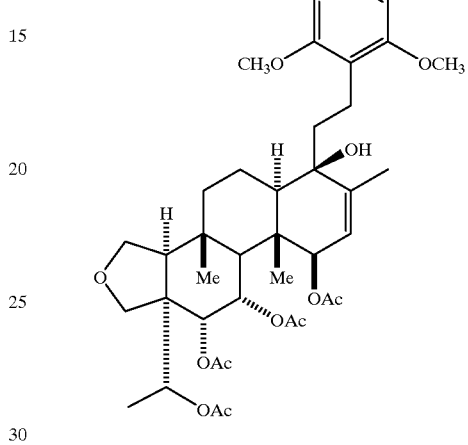

EXAMPLE 46

[3a-S-3aα,3bβ,5aα,9β,9aβ,10α,11α,11aα]-11a-(1-R-acetoxyethyl)-6-(2-phenyl-propyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

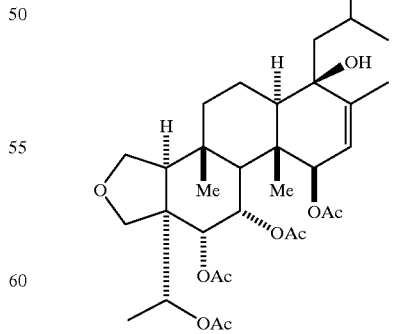

The title compound is isolated as a mixture of stereo isomers.

EXAMPLE 47

[3a-S-3aα,3bβ,5aα,9β,9aβ,10α,11α,11aα]-11a-(1-R-acetoxyethyl)-6-(2-phenyl-2-methylpropyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

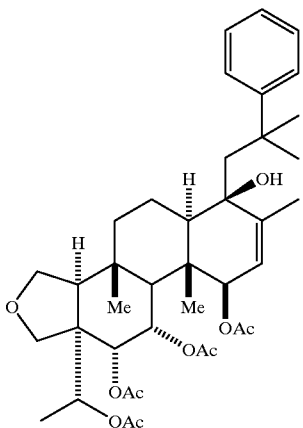

EXAMPLE 48

[3a-S-3aα,3bβ,5aα,9β,9aβ,10α,11α,11aα]-11a-(1-R-acetoxyethyl)-6-(2-hydroxyphenylethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

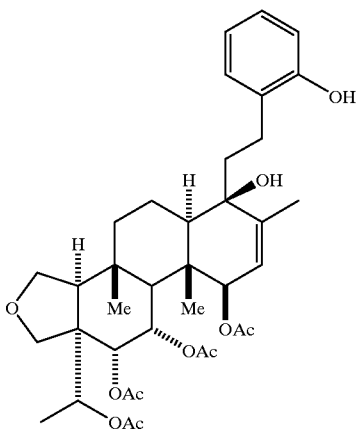

Step A: Preparation of 2-tetrahydropyranyloxyphenyl ethyl bromide

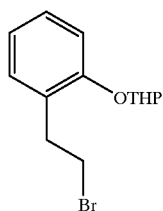

To a solution of 2-methoxyphenethyl alcohol (5.0 g, 32.6 mmol) in 40 ml of CH$_2$Cl$_2$ was added dimethylaminopyridine (DMAP) (10 mg), Et$_3$N (11.4 ml, 81.8 mmol) and MsCl (5.05 ml, 65.2 mmol) at 0° C. After 1 h, the reaction mixture was poured into hexane and it was washed with aqueous NaHCO$_3$ (2×), water and dried with MgSO$_4$. Upon removal of the solvents, the residue was dissolved in 50 ml of acetone and LiBr (11.34 g, 130.6 mmol) was added. After the solution was heated at reflux for 16 h, it was poured into ether and washed with water, dried with MgSO$_4$, filtered and dried to afford 2-methoxyphenethyl bromide.

To a solution of 2-methoxyphenethyl bromide (1.07 g, 4.98 mmol) in 5 ml of CH$_2$Cl$_2$ was added BBr$_3$ (9.5 ml, 1.0 M in CH$_2$Cl$_2$) at −78° C. and it was allowed to warm to rt over 1.5 h. The reaction mixture was poured into CH$_2$Cl$_2$ and was washed with brine, dried to afford 2-hydroxy phenethyl bromide.

To a solution of 2-hydroxyphenethyl bromide (241 mg, 1.20 mmol) in 6 ml of CH$_2$Cl$_2$ was added pyridinium p-toluene sulfonate (PPTS, 10 mg) and dihydropyran. After 2 h, volatiles were removed and the residue was purified by flash column to afford the title compound.

Step B: The THP ether derivative of the title compound was prepared according to the procedures described in Example 7. The THP protecting group is removed as follows. To the THP ether derivative in 4 ml of methanol was added 10 mg TsOH and the mixture stirred at rt for 3.5 h. After removal of solvent, the reaction mixture is purified by HPLC.

EXAMPLE 49

[3a-S-3aα,3bβ,5aα,9β,9aβ,10α,11α,11aα]-11a-(1-R-acetoxyethyl)-6-(2-(S)-phenylpropyl)-6-hydroxy-9,10,11-triacetoxy-3b,7,9a-trimethyl-1,3,3a, 3b,4,6,5a,6,9,9a,9b,10,11,11a-tetradecahydrophenanthro[1,2-c]furan

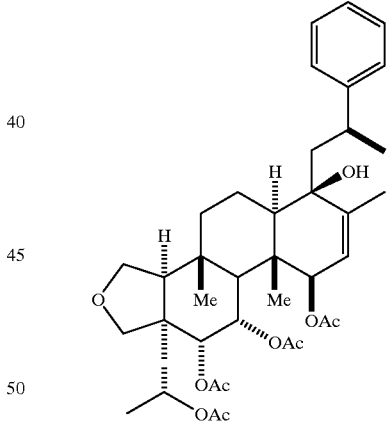

Step A: Preparation of R-(−)-2-phenylpropylbromide

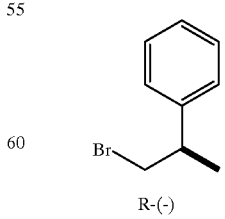

To a solution of R-(−)-2-phenylpropionic acid (1.04 g, 6.9 mmol) in 30 ml of THF was added LAH (6.9 ml, 1.0 M in THF) at 0° C. After stirring at rt for 14 h, the mixture was poured into 2 N HCl and the organic layer was washed with NaHCO₃ and brine, dried with MgSO₄ to give the corresponding alkanol which was converted to the bromide. The Grignard reagent was then prepared by the procedures described in Example 7 and reacted with the ketone to produce the title compound.

EXAMPLE 50

[3a-S-3aα,3bβ,5aα,9β,9aβ,10α,11α,11aα]-11a-(1-R-acetoxyethyl)-6-(2-phenylprop-2-enyl)-6-hydroxy-9,10,11-triacetoxy-3b,7,9a-trimethyl-1,3,3a,3b,4,5,5a,6,9,9a,9b 10,11,11a-tetradecahydro phenanthro[1,2-c]furan

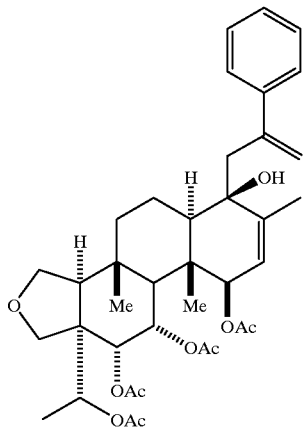

Step A: Preparation of 2-(phenyl)prop-2-enyltrimethylsilane

2 g of (2-bromoallyl)trimethylsilane (10.4 mmole) and 500 mg of tetrakis (triphenylphosphine) palladium (0.4 mmole) in 5 ml of benzene were heated to 80° C. until a homogenous solution resulted. The mixture was cooled to 40° C. and 10 ml of a 1M solution of phenylmagnesium chloride in THF were slowly added. The deep red reaction mixture was stirred at 40° C. for 12 h and poured into 20 ml of water. Extraction with ethyl acetate, washing of the combined organic layers with aqueous sodium chloride then drying over MgSO₄ gave an oil which was purified by silica gel chromatography with 19:1 hexanes-ethyl acetate to afford the title compound as a yellow oil.

¹H NMR (CDCl₃) δ0.06 (s, 9H, SiMe₃), 2.06 (s, 2H, CH₂), 4.91 (s, 1H, =CH₂), 5.17 (s, 1H, =CH₂), 7.26–7.64 (m, 2H, ar-H), 7.18–7.25 (m, 2H, ar-H).

Step B: To a solution of [3a-S-3aα,3bβ,5aα,9β,9aβ,10α,11α,11aα]-11a-(1-R-acetoxyethyl)-6-oxo-9,10,11-triacetoxy-3b,7,9a-trimethyl-1,3,3a,3b,4,5,5a,6,9,9a,9b,10,11,11a-tetradecahydrophenanthro[1,2-c]furan (Example 6) in CH₂Cl₂ is added a solution of TiCl₄ in CH₂Cl₂ at −78° C. The resulting suspension is stirred for 10 minutes then 0.2 ml of 2-phenylprop-2-enyltrimethylsilane is added. Stirring is continued at −40° C. until TLC control shows no remaining starting material. Water is then added, and the mixture is extracted with ethyl acetate The organic phase is washed with aqueous sodium chloride is then dried over MgSO₄ and concentrated. The residue is first filtered through a plug of silica gel and then purified by HPLC.

EXAMPLE 51

[3a-S-3aα,3bβ,5aα,9β,9aβ,10α,11α,11aα]-11a-(1-R-acetoxyethyl)-6-(2-(R)-phenylpropyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

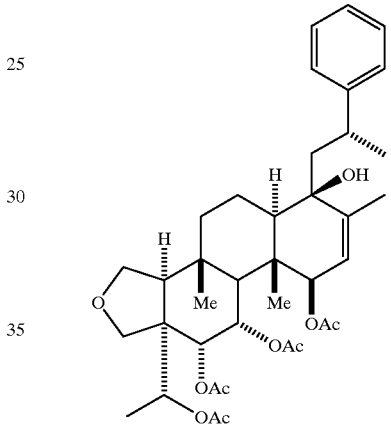

[3a-S-3aα,3bβ,5aα,9β,9aβ,10α,11α,11aα]-11a-(1-R-acetoxyethyl)-6-(2-phenylprop-2-enyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan (Example 49) is dissolved in dry THF. The solution is degassed under reduced pressure and saturated with nitrogen, the procedure being repeated several times. Wilkinson's catalyst [(PPh₃)₃RhCl] is added and the solution is degassed and saturated with hydrogen. The reaction vessel is pressurized with H₂ to 50 psi and hydrogenated on a Parr-apparatus at 25° C. When reaction is complete (TLC, HPLC) the solvent is removed under reduced pressure. The residue is first filtered through a plug of silica gel and then purified by HPLC (Waters RCM, Prep Nova-Pak HR Silica, 2 25×100 mm cartridges).

EXAMPLE 52

[3a-S-3aα,3bβ,5aα,9β,9aβ,10α,11α,11aα]-11a-(1-R-acetoxyethyl)-6-(2-(2-methoxyphenyl)prop-2-enyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

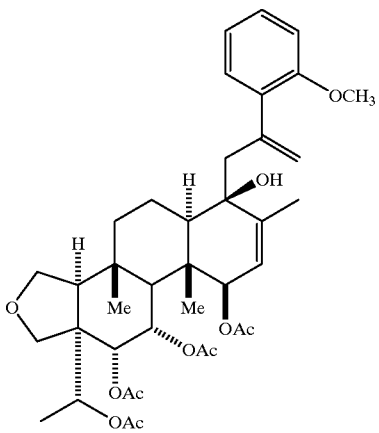

The title compound is prepared by procedures described in Example 49. The preparation of 2-(2'-methoxyphenyl)prop-2-enyltrimethylsilane is as follows.

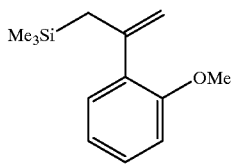

2 g of (2-bromoallyl)trimethylsilane (10.4 mmole) and 500 mg of tetrakis (triphenylphosphine)palladium (0.4 mmole) in 5 ml of benzene were heated to 80° C. until a homogenous solution resulted. The mixture was cooled to 40° C. and 10 ml of a 1M solution of phenylmagnesium chloride in THF were slowly added. The deep red reaction mixture was stirred at 40° C. for 12 h and poured into 20 ml of water. Extraction with ethyl acetate, washing of the combined organic layers with aqueous sodium chloride then drying over MgSO$_4$ gave an oil which was purified by silica gel chromatography with 19:1 hexanes-ethyl acetate to afford the title compound as a yellow oil.

$^1$H NMR (CDCl$_3$) δ0.12 (s, 9H, SiMe$_3$), 2.10 (s, 2H, CH$_2$), 3.86 (s, 3H, OMe), 4.90 (s, 1H, =CH$_2$), 4.97 (s, 1H, =CH$_2$), 6.82–6.98 (m, 2H, ar-H), 7.18–7.25 (m, 2H, ar-H).

EXAMPLE 53

[3a-S-3aα,3bβ,5aα,9β,9aβ,10α,11α,11aα]-11a-(1-R-acetoxyethyl)-6-(2-(2-ethylmercaptophenyl)prop-2-enyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

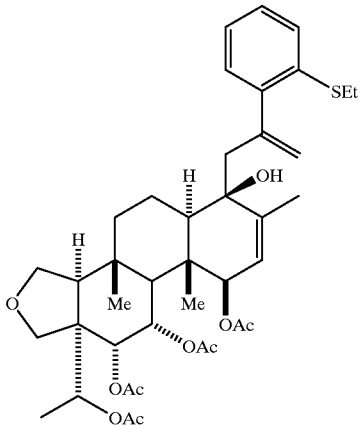

The title compound is prepared by procedures described in Example 50. The preparation 2-(2-ethylmercaptophenyl)-allyltrimethylsilane is as follows.

Step A: Preparation of 1-Ethylmercapto-2-bromobenzene

To a suspension of 1.00 g (5.3 mmol) of 2-bromobenzenethiol and 1.47 g (10.6 mmol) of potassium carbonate in 15 ml of N,N-dimethylformamide was added 1.65 g (10.6 mmol) of iodoethane at 0° C. The reaction mixture was stirred at 55–60° C. for 12 h and was poured into 200 ml of ether. It was washed with water (20 ml×3), dried over MgSO$_4$ and concentrated to afford 1-ethylmercapto-2-bromobenzene as a colorless oil.

Step B: Preparation of 2-(2-Ethylmercaptophenyl) allyltrimethylsilane

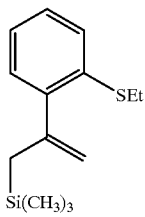

A solution of the Grignard reagent of 1-ethylmercapto-2-bromobenzene in tetrahydrofuran was prepared in the following way: 1.50 g (6.9 mmol) of 1-ethylmercapto-2-bromobenzene were added to 218 mg (9.0 mmol) of magnesium in 8 ml of anhydrous tetrahydrofuran at room temperature under N$_2$ and was heated to reflux for 1 h. Meanwhile, a solution of 1.20 g (6.2 mmol) of (2-bromoallyl)trimethylsilane and 358 mg (0.31 mmol) of tetrakis(triphenylphosphine)-palladium in 6 ml of dry benzene was stirred at 80° C. under $N_2$ for 30 min. Then it was cooled to 50° C. and to it was added the Grignard reagent described above. The reaction mixture was stirred at 40° C. for 3 h and was poured into 100 ml of ether. It was washed with water (20 ml×2), dried over $MgSO_4$ and concentrated. The residue was purified by silica gel chromatography with hexane to give [2-(2-ethylmercaptophenyl)allyl trimethylsilane as a colorless oil.

EXAMPLE 54

[3a-S-3aα,3bβ,5aα,9β,9aβ,10α,11α,11aα]-11a-(1-R-acetoxyethyl)-6-(2-(2-ethylphenyl)prop-2-enyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

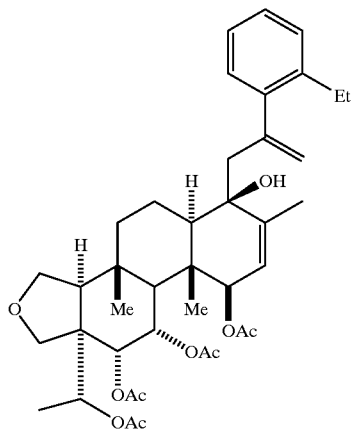

The title compound is prepared according to the procedures described in Example 50.

EXAMPLE 55

[3a-S-3aα,3bβ,5aα,9β,9aβ,10α,11α,11aα]-11a-(1-R-acetoxyethyl)-6-(2-(2-methylmercaptophenyl)prop-2-enyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

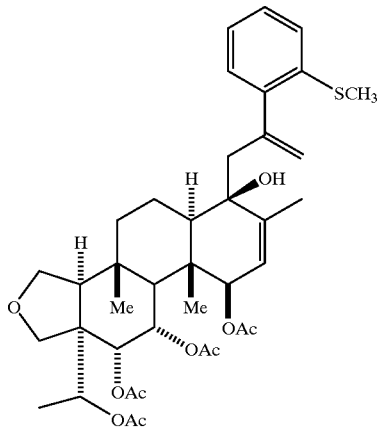

The title compound is prepared according to the procedures described in Example 50.

EXAMPLE 56

[3a-S-3aα,3bβ,5aα,9β,9aβ,10α,11α,11aα]-11a-(1-R-acetoxyethyl)-6-(2-(2-n-butylmercaptophenyl)prop-2-enyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

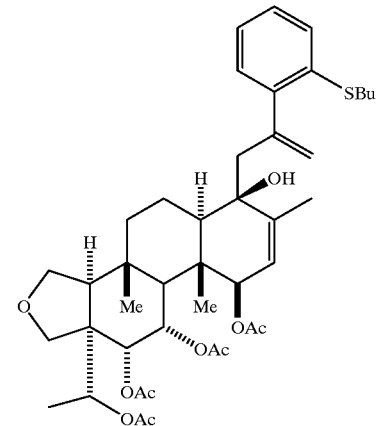

The title compound is prepared in the same manner as Example 50.

EXAMPLE 57

[3a-S-3aα,3bβ,5aα,9β,9aβ,10α,11α,11aα]-11a-(1-R-acetoxyethyl)-6-(2-(2-vinylphenyl)prop-2-enyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan

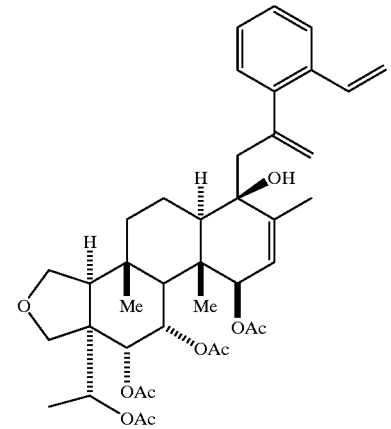

The title compound is prepared in the same manner as Example 49.

EXAMPLE 58

[3a-S-3aα,3bβ,5aα,9β,9aβ,10α,11α,11aα]-11a-(1-R-acetoxyethyl)-6-(2-(S)-(2-ethylphenyl)propyl)-6-hydroxy-9,10,11-triacetoxy-3b,7,9a-trimethyl-1,3,3a,3b,4,5,5a,6,9,9a9b,10,11,11a-tetradecahydro phenanthro[1,2-c]furan

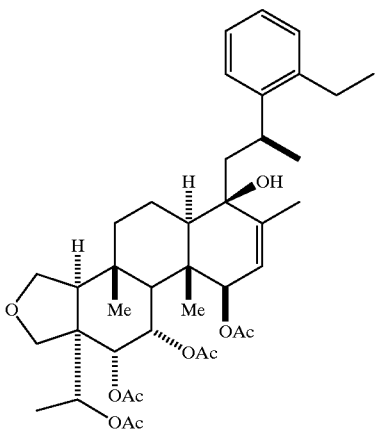

The title compound is prepared in the same manner as Example 50. The C6 sidechain is prepared as described below.

Step A: Preparation of (2-ethylphenyl)acetic acid

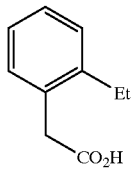

To a suspension of 8.53 g (350 mmoles) of magnesium in 270 mL in dry tetrahydrofuran was added 50 g (270 mmol) of 1-bromo-2-ethylbenzene. The temperature was maintained at 50° C. during addition, then was heated under reflux. After 1 h, the solution was cooled to −78° C. under $N_2$, and 54.42 g (324 mmoles) of allyl iodide was added dropwise. The mixture was allowed to warm to room temperature, stirred for an additional 2 h, then cooled to 0° C. The reaction was quenched by addition of 2M HCl and 500 mL of ether and the layers were separated. The organic layer was washed with 30 mL of saturated $NaHCO_3$ solution and brine, dried over $MgSO_4$, and concentrated. The oily residue was filtered through silica gel with 20% ethyl acetate-hexane and the eluate was concentrated to afford the crude 1-allyl-2-ethylbenzene as a colorless oil.

A solution of 54.05 g of the crude 1-allyl-2-ethylbenzene in 500 mL of 1:1 $CH_2Cl_2$—$CH_3OH$ was cooled to −78° C. A stream of $O_3$ was bubbled through the solution for 3 h, until all of the starting material had disappeared. Then a stream of air was bubbled through the solution until the blue color had faded. A total of 25 mL of methyl sulfide was added and the solution was stirred at room temperature for 1 h. The solution was concentrated and dried under vacuum to afford (2-ethylphenyl) acetaldehyde as a colorless oil which was used directly in the next step.

To a solution of the crude (2-ethylphenyl)acetaldehyde in 20 ml of EtOH was added a solution of 2.29 g (13.52 mmol) of $AgNO_3$ in 7.5 ml of water and a solution of 2.08 g (37.2 mmol) of KOH in 13 ml of water at 0° C. The reaction mixture was stirred at 0° C. for 2 h and was filtered to remove the precipitated silverhydroxide. The filtrate was extracted with $CH_2Cl_2$ (20 ml×3) and the organic fractions were discarded. The aqueous layer was acidified with 6N HCl to PH=1 and was extracted with $CH_2Cl_2$ (50 ml×3). The combined organic layers were dried over $MgSO_4$ and concentrated to give 2-ethylphenylacetic acid.

Step B: Preparation of (R)-4-benzyl-3-[2-(2-ethylphenyl) ethyl]oxazolidin-2-one

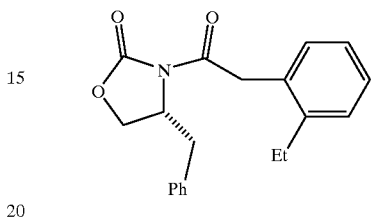

To a stirred solution of 2.16 g (13.2 mmol) of (2-ethylphenyl)acetic acid and 1.6 g (15.84 mmol) of triethylamine in 55 ml of anhydrous tetrahydrofuran was added 1.67 g (13.86 mmol) trimethylacetyl chloride at −78° C. under $N_2$. After the resultant white suspension was stirred for 10 min. at −78° C. and 30 min. at 0° C., it was recooled to −78° C. and a −78° C. solution of metallated oxazolidinone prepared by the addition of 8.67 ml (13,86 mmol, 1.6 M in hexane) of n-butyllithium to a −78° C. solution of 2.46 g (13.86 mmol) of (R)-(+)-4-benzyl-2-oxazolidinone in 50 ml of anhydrous tetrahydrofuran was added via cannula. The reaction mixture was stirred at 0° C. for an additional 30 min. and quenched by the addition of 50 ml of saturated aqueous ammonium chloride. The two layers were separated and the aqueous layer was extracted with $CH_2Cl_2$ (50 ml×3). The combined organic layers were dried over $MgSO_4$ and concentrated. The residue was purified by silica gel chromatography with 6:1 hexane/ethyl acetate to afford the title compound.

Step C: Preparation of (R),(R)-4-Benzyl-3-[2-(2-ethylphenyl)-propyl]oxazolidin-2-one

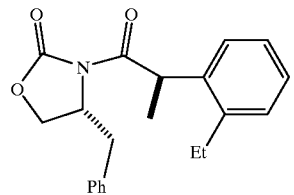

To a solution of 3.50 g (10.83 mmol) of (4R)-4-benzyl-3-[2-(2-ethyl-phenyl)-ethyl]-oxazolidin-2-one in 25 ml of tetrahydrofuran was added a solution of 13 ml (1.0 M, 13 mmol) of sodium bis(trimethylsilyl)amide at −78° C. under $N_2$. After the reaction mixture was stirred at −78° C. for 30 min., 3.29 g (9.92 mmol) of iodomethane was added at −78° C. The solution was stirred for 4 h and then quenched by the addition of 20 ml of aqueous saturated ammonium chloride solution. The two layers were separated and the aqueous was extracted with $CH_2Cl_2$ (50 ml×3). The combined organic layers were dried over $MgSO_4$ and concentrated. The residue was purified by silica gel chromatography with 500:35 hexane/ethyl acetate to afford the title compound. $[\alpha]^D$=−146 (c=1.55, $CHCl_3$).

Step D: Preparation of (R)-2-(2-Ethylphenyl)-propanol

To a solution of 2.20 g (6.50 mmol) of (R),(R)-4-benzyl-3-[2-(2-ethyl-phenyl)-propyl]-oxazolidin-2-one in 20 ml of tetrahydrofuran was added 13 ml (1.0 M in THF, 13 mmol) of lithium aluminum hydride slowly at 0° C. The reaction mixture was stirred at 0° C. for 2 h and then quenched by addition of 5 ml of water. The mixture was acidified with 2N HCl to PH=1 and was extracted with $CH_2Cl_2$ (50 ml×3). The combined organic layers were dried $MgSO_4$ and concentrated. The residue was purified by silica gel chromatography with 10:1 hexane/ethyl acetate to afford the title compound. $[\alpha]^D=5.6$ (c=7.15, $CHCl_3$).

Step E: Preparation of (R)-2-(2-Ethylphenol)propylbromide

A solution of 0.93 g (6.20 mmol) of (R)-2-(2-ethylphenyl) propanol in 40 ml of ether containing 2.60 g (9.92 mmol) of triphenylphosphine and 3.29 g (9.92 mmol) of carbon tetrabromide was stirred at room temperature for 3 h. It was filtered and concentrated. The residue was purified by silica gel chromatography with hexane to afford the title compound as a colorless oil (80%). $[\alpha]^D=19.1$ (c=1.15, $CHCl_3$).

EXAMPLE 59

[3a-S-3aα,3bβ,5aα,9β,9aβ,10α,11α,11aα]-11a-(1-R-acetoxyethyl)-6-(2-(S)-(−)-(2-methoxyphenyl) propyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan The title compound is prepared according to procedures described in Example 58.

What is claimed is:
1. A compound of structural Formula I:

or a pharmaceutically acceptable salt, crystal form, or hydrate, wherein:
   a and b are independently a single bond or a double bond, and represented by ----- in the structure above;
   n is: 0, 1 or 2;
   r is: 0 or 1;
   s is: 0 or 1;
   $R^1$ and $R^{10a}$ are independently:
   (1) H,
   (2) =O, when $R^2$ is absent or $R^{10b}$ is absent respectively,
   (3) $(C_1-C_{10})$-alkyl, wherein alkyl is unsubstituted or substituted with one or two substituents selected from the group consisting of:
      (a) halo, wherein halo is fluoro, chloro, bromo, or iodo,
      (b) hydroxy,
      (c) oxo,
      (d) $(C_1-C_6)$-alkyloxy,
      (e) $(C_1-C_6)$-S(O)$_n$—,
      (f) aryl-$(C_1-C_6)$-alkyloxy,
      (g) cyano,
      (h) nitro,
      (i) vinyl,
      (j) $NR^4R^5$,
      (k) $NR^4COC_1-C_6$-alkyl,
      (l) CHO,
      (m) $CO_2H$,
      (n) $COC_1-C_6$-alkyl,
      (o) $CO_2C_1-C_6$-alkyl,
      (p) $CONR^4R^5$,
      (q) aryl, wherein aryl is defined as phenyl or naphthyl, unsubstituted or substituted with one, two or three of the substituents selected from the group consisting of:
         (a') halo, as defined above,
         (b') hydroxy,
         (c') $(C_1-C_6)$-alkyl,
         (d') $(C_1-C_4)$-perfluoroalkyl,
         (e') $(C_1-C_6)$-alkenyl,
         (f') $(C_1-C_6)$-alkynyl,
         (g') $(C_1-C_6)$-alkyloxy,
         (h') $(C_1-C_6)$-alkyl-S(O)$_n$—,
         (i') phenyl,
         (j') phenoxy,
         (k') cyano,
         (l') nitro,
         (m') $CO_2H$,
         (n') $COC_1-C_6$-alkyl,
         (o') $CO_2C_1-C_6$-alkyl, (p') $CONR^4R^5$,
(q') $NR^4R^5$,
(r') $NR^4COC_1$–$C_6$-alkyl,
(s') $(C_1$–$C_6)$-alkenyloxy, and
(t') benzyloxy;
(r) heteroaryl, wherein heteroaryl is defined as an unsubstituted, monosubstituted, or disubstituted five or six membered aromatic heterocycle containing from 1 to 3 heteroatoms selected from the group consisting of O, N and S and wherein the substituents are selected from the group consisting of:
  (a') halo, as defined above,
  (b') hydroxy,
  (c') $(C_1$–$C_6)$-alkyl,
  (d') $(C_1$–$C_4)$-perfluoroalkyl,
  (e') $(C_1$–$C_6)$-alkenyl,
  (f') $(C_1$–$C_6)$-alkynyl,
  (g') $(C_1$–$C_6)$-alkyloxy,
  (h') $(C_1$–$C_6)$-alkyl-$S(O)_n$—,
  (i') phenyl,
  (j') phenoxy,
  (k') cyano,
  (l') nitro,
  (m') $CO_2H$,
  (n') $COC_1$–$C_6$-alkyl,
  (o') $CO_2C_1$–$C_6$-alkyl,
  (p') $CONR^4R^5$,
  (q') $NR^4R^5$,
  (r') $NR^4COC_1$–$C_6$-alkyl,
  (s') fused benzo, and
  (t') fused pyridyl group,
(s) heterocyclyl, wherein heterocyclyl is defined as a cyclic, non-aromatic moiety containing from 1 to 3 heteroatoms selected from the group consisting of O, N, and S, said heterocycle being unsubstituted or substituted with one, two or three substituents selected from the group consisting of:
  (a') halo, as defined above,
  (b') hydroxy,
  (c') $(C_1$–$C_6)$-alkyl,
  (d') $(C_1$–$C_4)$-perfluoroalkyl,
  (e') $(C_1$–$C_6)$-alkenyl,
  (f') $(C_1$–$C_6)$-alkynyl,
  (g') $(C_1$–$C_6)$-alkyloxy,
  (h') $(C_1$–$C_6)$-alkyl-$S(O)_n$—,
  (i') phenyl,
  (j') phenoxy,
  (k') cyano,
  (l') nitro,
  (m') $CO_2H$,
  (n') $COC_1$–$C_6$-alkyl,
  (o') $CO_2C_1$–$C_6$-alkyl,
  (p') $CONR^4R^5$,
  (q') $NR^4R^5$,
  (r') $NR^4COC_1$–$C_6$-alkyl, and
  (s') oxo,
  (t') fused benzo, and
  (u') fused pyridyl group;
(4) $(C_2$–$C_{10})$-alkenyl, wherein alkenyl is unsubstituted or substituted with one or two substituents selected from the group consisting of:
  (a) halo, wherein halo is fluoro, chloro, bromo, or iodo,
  (b) hydroxy,
  (c) oxo,
  (d) $(C_1$–$C_6)$-alkyloxy,
  (e) $(C_1$–$C_6)$-$S(O)_n$—,
  (f) phenyl-$(C_1$–$C_6)$-alkyloxy,
  (g) cyano,
  (h) nitro,
  (i) vinyl,
  (j) $NR^4R^5$,
  (k) $NR^4COC_1$–$C_6$-alkyl,
  (l) CHO,
  (m) $CO_2H$,
  (n) $COC_1$–$C_6$-alkyl,
  (o) $CO_2C_1$–$C_6$-alkyl,
  (p) $CONR^4R^5$,
  (q) aryl, wherein aryl is as defined above,
  (r) heteroaryl, wherein heteroaryl is as defined above, and
  (s) heterocycle, wherein the heterocycle is as defined above,
(5) $(C_2$–$C_{10})$-alkynyl, wherein alkynyl is unsubstituted or substituted with one or two substituents selected from the group consisting of:
  (a) halo, wherein halo is fluoro, chloro, bromo, or iodo,
  (b) hydroxy,
  (c) oxo,
  (d) $(C_1$–$C_6)$-alkyloxy,
  (e) $(C_1$–$C_6)$-$S(O)_n$—,
  (f) phenyl-$(C_1$–$C_6)$-alkyloxy,
  (g) cyano,
  (h) nitro,
  (i) vinyl,
  (j) $NR^4R^5$,
  (k) $NR^4COC_1$–$C_6$-alkyl,
  (l) CHO,
  (m) $CO_2H$,
  (n) $COC_1$–$C_6$-alkyl,
  (o) $CO_2C_1$–$C_6$-alkyl,
  (p) $CONR^4R^5$,
  (q) aryl, wherein aryl is as defined above,
  (r) heteroaryl, wherein heteroaryl is as defined above,
  (s) heterocyclyl, wherein heterocyclyl is as defined above, and
  (t) $Si(R^4)_3$,
(6) an exo-methylene group, when $R^2$ is absent or $R^{10b}$ is absent respectively; or
(7) aryl, wherein aryl is defined as phenyl or naphthyl, unsubstituted or substituted with one, two or three substituents selected from the group consisting of:
  (a') halo, as defined above,
  (b') hydroxy,
  (c') $(C_1$–$C_6)$-alkyl,
  (d') $(C_1$–$C_4)$-perfluoroalkyl,
  (e') $(C_1$–$C_6)$-alkenyl,
  (f') $(C_1$–$C_6)$-alkynyl,
  (g') $(C_1$–$C_6)$-alkyloxy,
  (h') $(C_1$–$C_6)$-alkyl-$S(O)_n$—,
  (i') phenyl,
  (j') phenoxy,
  (k') cyano,
  (l') nitro,
  (m') $CO_2H$,
  (n') $COC_1$–$C_6$-alkyl,
  (o') $CO_2C_1$–$C_6$-alkyl,
  (p') $CONR^4R^5$,
  (q') $NR^4R^5$,
  (r') $NR^4COC_1$–$C_6$-alkyl,
  (s') $(C_1$–$C_6)$-alkenyloxy, and (t') benzyloxy;

$R^2$ is:
(1) H,
(2) absent when $R^1$ is oxo,
(3) absent when $R^1$ is an exo-methylene group, or
(4) OH, $R^3$ is:
(1) H, or
(2) ($C_1$–$C_{10}$)-alkyl, wherein alkyl is unsubstituted or substituted with one or two substituents selected from the group consisting of:
 (a) halo, wherein halo is fluoro, chloro, bromo, iodo,
 (b) hydroxy,
 (c) oxo,
 (d) ($C_1$–$C_6$)-alkyloxy,
 (e) ($C_1$–$C_6$)-S(O)$_n$—,
 (f) aryl-($C_1$–$C_6$)-alkyloxy,
 (g) cyano,
 (h) nitro,
 (i) vinyl,
 (j) $NR^4R^5$,
 (k) $NR^4COC_1$–$C_6$-alkyl,
 (l) CHO,
 (m) $CO_2H$,
 (n) $COC_1$–$C_6$-alkyl,
 (o) $CO_2C_1$–$C_6$-alkyl,
 (p) $CONR^4R^5$,
 (q) aryl, wherein aryl is defined as phenyl or naphthyl, unsubstituted or substituted with one, two or three of the substituents selected from the group consisting of:
  (a') halo, as defined above,
  (b') hydroxy,
  (c') ($C_1$–$C_6$)-alkyl,
  (d') ($C_1$–$C_4$)-perfluoroalkyl,
  (e') ($C_1$–$C_6$)-alkenyl,
  (f') ($C_1$–$C_6$)-alkynyl,
  (g') ($C_1$–$C_6$)-alkyloxy,
  (h') ($C_1$–$C_6$)-alkyl-S(O)$_n$—,
  (i') phenyl,
  (j') phenoxy,
  (k') cyano,
  (l') nitro,
  (m') $CO_2H$,
  (n') $COC_1$–$C_6$-alkyl,
  (o') $CO_2C_1$–$C_6$-alkyl,
  (p') $CONR^4R^5$,
  (q') $NR^4R^5$, and
  (r') $NR^4COC_1$–$C_6$-alkyl,
 (r) heteroaryl, wherein heteroaryl is defined as an unsubstituted, monosubstituted, or disubstituted five or six membered aromatic heterocycle containing from 1 to 3 heteroatoms selected from the group consisting of O, N and S and wherein the substituents are members selected from the group consisting of:
  (a') halo, as defined above,
  (b') hydroxy,
  (c') ($C_1$–$C_6$)-alkyl,
  (d') ($C_1$–$C_4$)-perfluoroalkyl,
  (e') ($C_1$–$C_6$)-alkenyl,
  (f') ($C_1$–$C_6$)-alkynyl,
  (g') ($C_1$–$C_6$)-alkyloxy,
  (h') ($C_1$–$C_6$)-alkyl-S(O)$_n$—,
  (i') phenyl,
  (j') phenoxy,
  (k') cyano,
  (l') nitro,
  (m') $CO_2H$,
  (n') $COC_1$–$C_6$-alkyl,
  (o') $CO_2C_1$–$C_6$-alkyl,
  (p') $CONR^4R^5$,
  (q') $NR^4R^5$,
  (r') $NR^4COC_1$–$C_6$-alkyl, and
  (s') fused benzo or pyridyl group,
 (s) heterocyclyl, wherein heterocyclyl is defined as a cyclic, non-aromatic moiety containing from 1 to 3 heteroatoms selected from the group consisting of O, N, and S, said heterocycle being unsubstituted or substituted with one, two or three substituents selected from the group consisting of:
  (a') halo, as defined above,
  (b') hydroxy,
  (c') ($C_1$–$C_6$)-alkyl,
  (d') ($C_1$–$C_4$)-perfluoroalkyl,
  (e') ($C_1$–$C_6$)-alkenyl,
  (f') ($C_1$–$C_6$)-alkynyl,
  (g') ($C_1$–$C_6$)-alkyloxy,
  (h') ($C_1$–$C_6$)-alkyl-S(O)$_n$—,
  (i') phenyl,
  (j') phenoxy,
  (k') cyano,
  (l') nitro,
  (m') $CO_2H$,
  (n') $COC_1$–$C_6$-alkyl,
  (o') $CO_2C_1$–$C_6$-alkyl,
  (P') $CONR^4R^5$,
  (q') $NR^4R^5$,
  (r') $NR^4COC_1$–$C_6$-alkyl, and
  (s') oxo,
  (t') fused benzo, and
  (u') fused pyridyl group;
 (t) $Si(R^4)_3$,
(3) ($C_2$–$C_{10}$)-alkenyl, wherein alkenyl is unsubstituted or substituted with one or two substituents selected from the group consisting of:
 (a) halo, wherein halo is fluoro, chloro, bromo, or iodo,
 (b) hydroxy,
 (c) oxo,
 (d) ($C_1$–$C_6$)-alkyloxy,
 (e) ($C_1$–$C_6$)-S(O)$_n$—,
 (f) phenyl-($C_1$–$C_6$)-alkyloxy,
 (g) cyano,
 (h) nitro,
 (i) vinyl,
 (j) $NR^4R^5$,
 (k) $NR^4COC_1$–$C_6$-alkyl,
 (l) CHO,
 (m) $CO_2H$,
 (n) $COC_1$–$C_6$-alkyl,
 (o) $CO_2C_1$–$C_6$-alkyl,
 (p) $CONR^4R^5$,
 (q) aryl, wherein aryl is as defined above,
 (r) heteroaryl, wherein heteroaryl is as defined above, and
 (s) heterocyclyl, wherein heterocyclyl is as defined above;
(4) ($C_2$–$C_{10}$)-alkynyl, wherein alkynyl is unsubstituted or substituted with one or two substituents selected from the group consisting of:
 (a) halo, wherein halo is fluoro, chloro, bromo, or iodo,
 (b) hydroxy, (c) oxo,
(d) $(C_1-C_6)$-alkyloxy,
(e) $(C_1-C_6)$-S(O)$_n$—,
(f) phenyl-$(C_1-C_6)$-alkyloxy,
(g) cyano,
(h) nitro,
(i) vinyl,
(j) NR$^4$R$^5$,
(k) NR$^4$COC$_1$-C$_6$-alkyl,
(l) CHO,
(m) CO$_2$H,
(n) COC$_1$-C$_6$-alkyl,
(o) CO$_2$C$_1$-C$_6$-alkyl,
(p) CONR$^4$R$^5$,
(q) aryl, wherein aryl is as defined above,
(r) heteroaryl, wherein heteroaryl is as defined above, and
(s) heterocyclyl, wherein heterocyclyl is as defined above; or
(5) cyano;
R$^4$ and R$^5$ are independently:
(1) hydrogen,
(2) $C_1-C_6$ alkyl, or
(3) aryl, wherein aryl is defined above,
R$^6$ is:
(1) hydrogen,
(2) oxo and a is a single bond,
(3) O[(C=O)O$_r$]$_s$R$^{11}$,
(4) O[(C=O)O$_r$]$_s$aryl, aryl as defined above,
(5) O[(C=O)O$_r$]$_s$heteroaryl, heteroaryl as defined above,
(6) OC(=O)NR$^{11}$R$^{12}$,
(7) NR$^{11}$R$^{12}$, or
(8) absent, when a is a double bond;
R$^7$, R$^8$ and R$^9$ are independently selected from the group consisting of:
(1) hydrogen,
(2) oxo,
(3) O[(C=O)O$_r$]$_s$R$^{11}$,
(4) O[(C=O)O$_r$]$_s$aryl, aryl as defined above,
(5) O[(C=O)O$_r$]$_s$heteroaryl, heteroaryl as defined above,
(6) OC(=O) NR$^{11}$R$^{12}$, and
(7) NR$^{11}$R$^{12}$;
R$^{10b}$ is:
(1) H,
(2) absent when R$^{10a}$ is oxo,
(3) an exo-methylene group, when R$^2$ is absent or R$^{10b}$ is absent respectively, or
(4) OH; and
R$^{11}$ and R$^{12}$ are independently chosen from the group consisting of:
(1) H, and
(2) $(C_1-C_6)$-alkyl, wherein alkyl is unsubstituted or substituted with one, two or three substituents selected from the group consisting of: Br, Cl, F, I, $(C_1-C_6)$-alkoxy, vinyl, cyano, oxo, nitro, hydroxy, CHO, CO$_2$H, COC$_1$-C$_6$-alkyl, CO$_2$C$_1$-C$_6$-alkyl, CONR$^4$R$^5$, NR$^4$R$^5$, NR$^4$COC$_1$-C$_6$-alkyl, aryl, wherein aryl is defined as phenyl or naphthyl, unsubstituted or substituted with one, two or three substituents selected from the group consisting of: Br, Cl, F, I, $(C_1-C_6)$-alkoxy, phenyl, phenoxy, cyano, oxo, nitro, hydroxy, CHO, CO$_2$H, COC$_1$-C$_6$-alkyl, CO$_2$C$_1$-C$_6$-alkyl, CONR$^4$R$^5$, NR$^4$R$^5$, NR$^4$COC$_1$-C$_6$-alkyl and any two of adjacent substituents can be joined to form a 5-, 6- or 7-membered fused ring said ring containing 1 or 2 oxygen atoms and the remainder carbon atoms, heteroaryl, wherein heteroaryl is defined as a 5 or 6-membered ring substituted with one and two heteroatoms selected from O, S, N, unsubstituted or substituted with one, two or three substituents selected from the group consisting of: Br, Cl, F, I, $(C_1-C_6)$-alkoxy, cyano, oxo, nitro, hydroxy, CHO, CO$_2$H, COC$_1$-C$_6$-alkyl, CO$_2$C$_1$-C$_6$-alkyl, CONR$^4$R$^5$, NR$^4$R$^5$, NR$^4$COC$_1$-C$_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring.

2. The compound of structural Formula I as recited in claim 1, wherein:
R$^{10a}$ is further defined as:
(1) H,
(2) =O, when R$^{10b}$ is absent,
(3) $(C_1-C_4)$-alkyl, wherein alkyl is unsubstituted or substituted with one or two substituents selected from the group consisting of:
(a) halo, wherein halo is fluoro, chloro, bromo, or iodo,
(b) hydroxy,
(c) oxo,
(d) $(C_1-C_3)$-alkyloxy,
(e) CHO,
(g) CO$(C_1-C_3)$-alkyl,
(i) aryl, wherein aryl is defined as phenyl or naphthyl, unsubstituted or substituted with one or two of the substituents selected from the group consisting of:
(a') halo, as defined above,
(b') hydroxy,
(c') $(C_1-C_6)$-alkyl,
(d') $(C_1-C_4)$-perfluoroalkyl,
(e') $(C_1-C_6)$-alkenyl,
(f') $(C_1-C_6)$-alkynyl,
(g') $(C_1-C_6)$-alkyloxy,
(h') $(C_1-C_6)$-alkyl-S(O)$_n$—,
(i') phenyl,
(j') phenoxy,
(k') cyano,
(l') nitro,
(m') CO$_2$H,
(n') COC$_1$-C$_6$-alkyl,
(o') CO$_2$C$_1$-C$_6$-alkyl,
(p') CONR$^4$R$^5$,
(q') NR$^4$R$^5$,
(r') NR$^4$COC$_1$-C$_6$-alkyl,
(s') $(C_1-C_6)$-alkenyloxy, and
(t') benzyloxy;
(j) heteroaryl, wherein heteroaryl is defined as pyridyl or thienyl,
(4) $(C_2-C_4)$-alkenyl, wherein alkenyl is unsubstituted or substituted with aryl, wherein aryl is as defined above;
(5) $(C_2-C_3)$-alkynyl, wherein alkynyl is unsubstituted or substituted with phenyl or Si(R$^4$)$_3$, or
(6) an exo-methylene group, when R$^{10b}$ is absent.

3. The compound of structural Formula I as recited in claim 2, wherein:
R$^3$ is further defined as:
(1) H, or (2) $(C_1-C_3)$-alkyl, wherein alkyl is unsubstituted or substituted with one or two substituents selected from the group consisting of:
  (a) halo, wherein halo is fluoro, chloro, bromo, iodo,
  (b) hydroxy,
  (c) oxo,
  (d) $(C_1-C_6)$-alkyloxy,
  (e) $(C_1-C_6)$-S(O)$_n$—,
  (f) aryl-$(C_1-C_6)$-alkyloxy,
  (g) cyano,
  (h) nitro,
  (i) vinyl,
  (t) $NR^4R^5$,
  (k) $NR^4COC_1-C_6$-alkyl,
  (l) CHO,
  (m) $CO_2H$,
  (n) $COC_1-C_6$-alkyl,
  (o) $CO_2C_1-C_6$-alkyl,
  (p) $CONR^4R^5$,
  (q) aryl, wherein aryl is defined as phenyl or naphthyl, unsubstituted or substituted with one, two or three of the substituents selected from the group consisting of:
    (a') halo, as defined above,
    (b') hydroxy,
    (c') $(C_1-C_6)$-alkyl,
    (d') $(C1-C4)$-perfluoroalkyl,
    (e') $(C_1-C_6)$-alkenyl,
    (f') $(C_1-C_6)$-alkynyl,
    (g') $(C_1-C_6)$-alkyloxy,
    (h') $(C_1-C_6)$-alkyl-S(O)$_n$—,
    (i') phenyl,
    (j') phenoxy,
    (k') cyano,
    (l') nitro,
    (m') $CO_2H$,
    (n') $COC_1-C_6$-alkyl,
    (o') $CO_2C_1-C_6$-alkyl,
    (p') $CONR^4R^5$,
    (g') $NR^4R^5$, and
    (r') $NR^4COC_1-C_6$-alkyl,
  (r) $Si(R^4)_3$,
(3) $(C_2-C_3)$-alkenyl, wherein alkenyl is unsubstituted or substituted with one or two substituents selected from the group consisting of:
  (a) halo, wherein halo is fluoro, chloro, bromo, or iodo,
  (b) hydroxy,
  (c) oxo,
  (d) $(C_1-C_6)$-alkyloxy,
  (e) $(C_1-C_6)$-S(O)$_n$—,
  (f) phenyl-$(C_1-C_6)$-alkyloxy,
  (g) cyano,
  (h) nitro,
  (i) vinyl,
  (j) $NR^4R^5$,
  (k) $NR^4COC_1-C_6$-alkyl,
  (l) CHO,
  (m) $CO_2H$,
  (n) $COC_1-C_6$-alkyl,
  (o) $CO_2C_1-C_6$-alkyl,
  (p) $CONR^4R^5$,
  (q) aryl, wherein aryl is as defined above,
  (r) heteroaryl, wherein heteroaryl is as defined above, and
  (s) heterocyclyl, wherein heterocyclyl is as defined above;

(4) $(C_2-C_3)$-alkynyl, wherein alkynyl is unsubstituted or substituted with one or two substituents selected from the group consisting of:
  (a) halo, wherein halo is fluoro, chloro, bromo, or iodo,
  (b) hydroxy,
  (c) oxo,
  (d) $(C_1-C_6)$-alkyloxy,
  (e) $(C_1-C_6)$-S(O)$_n$—,
  (f) phenyl-$(C_1-C_6)$-alkyloxy,
  (g) cyano,
  (h) nitro,
  (i) vinyl,
  (j) $NR^4R^5$,
  (k) $NR^4COC_1-C_6$-alkyl,
  (l) CHO,
  (m) $CO_2H$,
  (n) $COC_1-C_6$-alkyl,
  (o) $CO_2C_1-C_6$-alkyl,
  (p) $CONR^4R^5$,
  (q) aryl, wherein aryl is as defined above,
  (r) heteroaryl, wherein heteroaryl is as defined above, and
  (s) heterocyclyl, wherein heterocyclyl is as defined above; or
(5) cyano;

$R^4$ and $R^5$ are further defined independently as:
  (1) hydrogen,
  (2) $C_1-C_3$ alkyl, or
  (3) phenyl, $R^6$ is further defined as:
  (1) hydrogen,
  (2) oxo and a is a single bond,
  (3) $O(C=O)R^{11}$, or
  (4) absent when a is a double bond;

$R^7$, $R^8$ and $R^9$ are further defined as independently selected from the group consisting of:
  (1) hydrogen,
  (2) oxo,
  (3) $O(C=O)R^{11}$; and $R^{11}$ and $R^{12}$ are further defined as independently chosen from the group consisting of:
  (1) H, and
  (2) $(C_1-C_3)$-alkyl.

4. The compound of structural Formula I as recited in claim 2, wherein:

$R^1$ is further defined as:
  (1) H,
  (2) =O, when R is absent,
  (3) $(C_1-C_8)$-alkyl, wherein alkyl is unsubstituted or substituted with one or two substituents selected from the group consisting of:
    (a) halo, wherein halo is fluoro, chloro, bromo, or iodo,
    (b) hydroxy,
    (c) oxo,
    (d) $(C_1-C_3)$-alkyloxy,
    (e) CHO,
    (g) $CO(C_1-C_3)$-alkyl,
    (i) aryl, wherein aryl is defined as phenyl or naphthyl, unsubstituted or substituted with one, two or three of the substituents selected from the group consisting of:
      (a') halo, as defined above,
      (b') hydroxy,
      (c') $(C_1-C_6)$-alkyl, (d') $(C_1-C_4)$-perfluoroalkyl,
(e') $(C_1-C_6)$-alkenyl,
(f') $(C_1-C_6)$-alkynyl,
(g') $(C_1-C_6)$-alkyloxy,
(h') $(C_1-C_6)$-alkyl-$S(O)_n$—,
(i') phenyl,
(j') phenoxy,
(k') cyano,
(l') nitro,
(m') $CO_2H$,
(n') $COC_1-C_6$-alkyl,
(o') $CO_2C_1-C_6$-alkyl,
(p') $CONR^4R^5$,
(q') $NR^4R^5$,
(r') $NR^4COC_1-C_6$-alkyl,
(s') $(C_1-C_6)$-alkenyloxy, and
(t') benzyloxy;
(j) heteroaryl, wherein heteroaryl is defined as pyridyl or thienyl,
(4) $(C_2-C_6)$-alkenyl, wherein alkenyl is unsubstituted or substituted with aryl, wherein aryl is as defined above; and
(5) $(C_2-C_3)$-alkynyl, wherein alkynyl is unsubstituted or substituted with phenyl or $Si(R^4)_3$, or
(6) an exo-methylene group, when $R^2$ is absent;
$R^3$ is further defined as:
(1) H, or
(2) $(C_1-C_3)$-alkyl, wherein alkyl is unsubstituted or substituted with phenyl or $Si(R^4)_3$,
(3) $(C_2-C_3)$-alkenyl, wherein alkenyl is unsubstituted or substituted with aryl, wherein aryl is defined as phenyl or naphthyl, unsubstituted or substituted with one, two or three substituents selected from the group consisting of:
(a') halo, as defined above,
(b') hydroxy,
(c') $(C_1-C_6)$-alkyl,
(d') $(C_1-C_4)$-perfluoroalkyl,
(e') $(C_1-C_6)$-alkenyl,
(f') $(C_1-C_6)$-alkynyl,
(g') $(C_1-C_6)$-alkyloxy,
(h') $(C_1-C_6)$-alkyl-$S(O)_n$—,
(i') phenyl,
(j') phenoxy,
(k') cyano,
(l') nitro,
(m') $CO_2H$,
(n') $COC_1-C_6$-alkyl,
(o') $CO_2C_1-C_6$-alkyl,
(p') $CONR^4R^5$,
(q') $NR^4R^5$,
(r') $NR^4COC_1-C_6$-alkyl,
(s') $(C_1-C_6)$-alkenyloxy, and
(t') benzyloxy;
(4) cyano;
$R^4$ and $R^5$ are further defined independently as:
(1) hydrogen,
(2) $C_1-C_3$ alkyl or
(3) phenyl,
$R^6$ is further defined as:
(1) hydrogen,
(2) oxo and a is a single bond,
(3) $O(C=O)R^{11}$, or
(4) absent when a is a double bond;
$R^7$, $R^8$ and $R^9$ are further defined as independently selected from the group consisting of:
(1) hydrogen,
(2) oxo, and
(3) $O(C=O)R^{11}$; and $R^{11}$ and $R^{12}$ are further defined as independently chosen from the group consisting of:
(1) H, and
(2) $(C_1-C_3)$-alkyl.

5. The compound of structural Formula I as recited in claim 4, wherein $R^{10a}$ and $R^{10b}$ are further defined as H.

6. A compound selected from the group consisting of:

[3a-S-3aa,3bb,5aa,9b,9ab,10a,11a,11aa]-11a-(1-R-acetoxyethyl)-6-oxo-9,10,11-triacetoxy-3b,7,9a-trimethyl-1,3,3a,3b,4,5,5a,6,9,9a,9b,10,11,11a-tetradecahydrophenanthro[1,2-c]furan;

[3a-S-3aa,3bb,5aa,9b,9ab,10a,11a,11aa]-11a-(1-R-acetoxyethyl)-6-benzyl-6-hydroxy-9,10,11-triacetoxy-3b,7,9a-trimethyl-1,3,3a,3b,4,5,5a,6,9,9a,9b,10,11,11a-tetradecahydrophenanthro[1,2-c]furan;

[3a-S-3aa,3bb,5aa,9b,9ab,10a,11a,11aa]-11a-(1-R-acetoxyethyl)-6-n-butyl-6-hydroxy-9,10,11-triacetoxy-3b,7,9a-trimethyl-1,3,3a,3b,4,5,5a,6,9,9a,9b,10,11,11a-tetradecahydrophenanthro 1,2-c]furan;

[3a-S-3aa,3bb,5aa,9b,9ab,10a,11a,11aa]-11a-(1-R-acetoxyethyl)-6-(3-phenyl-n-propyl)-6-hydroxy-9,10,11-triacetoxy-3b,7,9a-trimethyl-1,3,3a,3b,4,5,5a,6,9,9a,9b,10,11,11a-tetradecahydrophenanthro[1,2-c]furan;

[3a-S-3aa,3bb,5aa,9b,9ab,10a,11a,11aa]-11a-(1-R-acetoxyethyl)-6-(2-phenethyl)-6-hydroxy-9,10,11-triacetoxy-3b,7,9a-trimethyl-1,3,3a,3b,4,5,5a,6,9,9a,9b,10,11,11a-tetradecahydrophenanthro[1,2-c]furan;

[3a-S-3aa,3bb,5aa,9b,9ab,10a,11a,11aa]-11a-(1-R-acetoxyethyl)-6-(2-phenethyl)-6-hydroxy-9,10,11-triacetoxy-3b,7,9a-trimethyl-1,3,3a, 3b,4,5,5a,6,7,8,9,9a,9b,10,11,11a-hexadecahydrophenanthro[1,2-c]furan;

[3a-S-3aa,3bb,5aa,9b,9ab,10a,11a,11aa]-11a-(1-R-acetoxyethyl)-6-(2-phenethyl)-9,10,11-triacetoxy-3b,7,9a-trimethyl-1,3,3a,3b,4,5,7,8,9,9a,9b,10,11,11a-tetradecahydrophenanthro[1,2-c]furan;

[3a-S-3aa,3bb,5aa,9b,9ab,10a,11a,11aa]-11a-(1-R-acetoxyethyl)-6-(2-(2-methoxyphenyl)ethyl)-6-hydroxy-9,10,11-triacetoxy-3b,7,9a-trimethyl-1,3,3a,3b,4,5,5a,6,9,9a,9b,10,11,11a-tetradecahydrophenanthro[1,2-c]furan;

[3a-S-3aa,3bb,5aa,9b,9ab,10a,11a,11aa]-11a-(1-R-acetoxyethyl)-6-(2-(2-ethoxyphenyl)ethyl))-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2-n-butyloxyphenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2-allyloxyphenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2-benzyloxyphenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(but-3-en-1-yl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(4-dimethyl-pent-3-en-1-yl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2-fluorophenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2,6-difluorophenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2-chlorophenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2-chlorophenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(4-chlorophenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(3,4-dichlorophenyl)ethyl)-6-hydroxy-9,10,11-triacetoxy-3b,7,9a-trimethyl- 1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2-methylphenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(3-methylphenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(4-methylphenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2-trifluoromethylphenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(3-trifluoromethylphenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-naphth-2-ylethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-naphth-1-ylethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(3-methoxyphenyl)ethyl))-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl) 6-(2-(4-methoxyphenyl)ethyl))-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2,3-dimethoxyphenyl)ethyl))-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(3,4-dimethoxyphenyl)ethyl))-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)6-(2-(2,5-dimethoxyphenyl)ethyl))-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(3,5-dimethoxyphenyl)ethyl)-6-hydroxy-9,10,11-triacetoxy-3b,7,9a-trimethyl- 1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(3,4-methylenedioxyphenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2,3-methylenedioxyphenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(4-dimethylaminophenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2,2-diphenylethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2-methoxy-5-methylphenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(thien-2-yl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2,6-dimethoxylphenyl)ethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-phenyl-propyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-phenyl-2-methylpropyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-hydroxyphenylethyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(S)-phenylpropyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-phenylprop-2-enyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(R)-phenylpropyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2-methoxyphenyl)prop-2-enyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2-ethylmercaptophenyl)prop-2-enyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2-ethylphenyl)prop-2-enyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2-methylmercaptophenyl)prop-2-enyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-n-butylmercaptophenyl)prop-2-enyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(2-vinylphenyl)prop-2-enyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan;

[3a-S-3aa,3bb,5aa,9b,9ab,10a,11a,11aa]-11a-(1-R-acetoxyethyl)-6-(2-(S)-(2-ethylphenyl)propyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan; and

[3a-S-3aa,3bb,5aa,9b,9ab,10a,11a,11aa]-11a-(1-R-acetoxyethyl)-6-(2-(S)-(−)-(2-methoxyphenyl)propyl)-6-hydroxy-9,10,11-triacetoxy-3b,7,9a-trimethyl-1,3,3a,3b,4,5,5a,6,9,9a,9b,10,11,11a-tetradecahydro phenanthro[1,2-c]furan.

7. A method of preventing or treating the resistance to transplantation or transplantation rejection of organs or tissues into a patient in need thereof, which comprises the administration of a therapeutically effective amount of a compound of claim 1.

8. A method of suppressing the immune system in a subject in need thereof, which comprises the administration to the subject of an immune suppressing amount of a compound of Formula I, as recited in claim 1.

9. A pharmaceutical formulation comprising a pharmaceutically acceptable carrier and a therapeutically effective amount of the compound of Formula I, as recited in claim 1 or a pharmaceutically acceptable crystal form or hydrate thereof.

10. The pharmaceutical formulation of claim 9, comprising in addition, a second immunosuppressive agent comprising azathioprine, brequinar sodium, deoxyspergualin, mizaribine, mycophenolic acid morpholino ester, cyclosporin, FK-506 and rapamycin.

11. The method of claim 8, comprising the coadministration of a second immunosuppressive agent.

* * * * *